(12) United States Patent
Gryko et al.

(10) Patent No.: US 6,324,091 B1
(45) Date of Patent: *Nov. 27, 2001

(54) TIGHTLY COUPLED PORPHYRIN MACROCYCLES FOR MOLECULAR MEMORY STORAGE

(75) Inventors: Daniel Tomasz Gryko, Raleigh, NC (US); Peter Christian Clausen, Hunzenschwil (CH); David F. Bocian, Riverside; Werner G. Kuhr, Oak Hills, both of CA (US); Jonathan S. Lindsey, Raleigh, NC (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/484,394

(22) Filed: Jan. 14, 2000

(51) Int. Cl.[7] .................................................. G11C 7/00
(52) U.S. Cl. .......................... 365/151; 429/104; 429/42; 429/102; 429/103; 528/210
(58) Field of Search .............................. 365/151; 429/42, 429/102, 103, 104; 528/210

(56) References Cited

U.S. PATENT DOCUMENTS

| | | |
|---|---|---|
| 3,833,894 | 9/1974 | Aviram et al. . |
| 4,663,270 | 5/1987 | Potember et al. . |
| 4,670,860 | 6/1987 | Wilson . |
| 4,781,443 | 11/1988 | Giles . |
| 5,010,451 | 4/1991 | Ueyama et al. . |
| 5,016,063 | 5/1991 | Beratan et al. . |
| 5,035,835 | 7/1991 | Asakawa et al. . |
| 5,063,417 | 11/1991 | Hopfield . |
| 5,075,738 | 12/1991 | Matsuda et al. . |
| 5,135,637 | 8/1992 | Eida et al. . |
| 5,222,060 | 6/1993 | Kuroda et al. . |
| 5,252,698 | 10/1993 | Bhardwaj et al. . |
| 5,264,876 | 11/1993 | Kawade et al. . |
| 5,312,896 | 5/1994 | Bhardwaj et al. . |
| 5,432,379 | 7/1995 | Eguchi et al. . |
| 5,434,842 | 7/1995 | Weiss et al. . |
| 5,463,014 | * 10/1995 | Epstein et al. ................... 528/210 |
| 5,475,075 | * 12/1995 | Brant et al. ...................... 526/348.3 |
| 5,506,420 | 4/1996 | Kossovsky et al. . |
| 5,525,811 | 6/1996 | Sakurai et al. . |
| 5,539,100 | 7/1996 | Wasielewski et al. . |
| 5,707,845 | 1/1998 | Ueyama et al. . |
| 5,744,598 | 4/1998 | Shalkos et al. . |
| 5,804,850 | 9/1998 | Evans, Jr. et al. . |
| 5,814,420 | * 9/1998 | Chu ...................................... 429/104 |
| 5,840,443 | 11/1998 | Gregg et al. . |
| 5,844,055 | * 12/1998 | Brandt et al. ...................... 526/127 |
| 5,858,666 | 1/1999 | Weiss . |
| 6,013,170 | * 1/2000 | Meade ................................ 205/777.5 |

* cited by examiner

*Primary Examiner*—Viet Q. Nguyen
(74) *Attorney, Agent, or Firm*—The Law Offices of Jonathan Alan Quine; Tom Hunter

(57) ABSTRACT

This invention provides novel high density memory devices that are electrically addressable permitting effective reading and writing, that provide a high memory density (e.g., $10^{15}$ bits/cm$^3$), that provide a high degree of fault tolerance, and that are amenable to efficient chemical synthesis and chip fabrication. The devices are intrinsically latchable, defect tolerant, and support destructive or non-destructive read cycles. In a preferred embodiment, the device comprises a fixed electrode electrically coupled to a storage medium comprising a storage molecule comprising a first subunit and a second subunit wherein the first and second subunits are tightly coupled such that oxidation of the first subunit alters the oxidation potential(s) of the second subunit rendering the oxidation potential(s) of the second unit different and distinguishable from the oxidation potentials of the first subunit.

72 Claims, 19 Drawing Sheets

101  X-axis Logic
(Two Levels
of Working
Electrodes)

Y-axis Logic
(Common
Reference
Electrode)

103

Scheme 1

Equation 1

Equation 2

Scheme 4

Scheme 5

Scheme 6

TIGHTLY COUPLED PORPHYRIN MACROCYCLES FOR MOLECULAR MEMORY STORAGE

STATEMENT AS TO RIGHTS TO INVENTIONS MADE UNDER FEDERALLY SPONSORED RESEARCH AND DEVELOPMENT

This invention was made with Government support under Grant No. GM26738, awarded by the National Institute of Health. The Government of the United States of America may have certain rights in this invention.

CROSS-REFERENCE TO RELATED APPLICATIONS

[Not Applicable]

FIELD OF THE INVENTION

This invention relates to memory devices. In particular this invention provides a nonvolatile electronic memory device capable of storing information in extremely high density.

BACKGROUND OF THE INVENTION

Basic functions of a computer include information processing and storage. In typical computer systems, these arithmetic, logic, and memory operations are performed by devices that are capable of reversibly switching between two states often referred to as "0" and "1." In most cases, such switching devices are fabricated from semiconducting devices that perform these various functions and are capable of switching between two states at a very high speed using minimum amounts of electrical energy. Thus, for example, transistors and transistor variants perform the basic switching and storage functions in computers.

Because of the huge data storage requirements of modem computers, a new, compact, low-cost, very high capacity, high speed memory configuration is needed. To reach this objective, molecular electronic switches, wires, microsensors for chemical analysis, and opto-electronic components for use in optical computing have been pursued. The principal advantages of using molecules in these applications are high component density (upwards of $10^{18}$ bits per square centimeter), increased response speeds, and high energy efficiency.

A variety of approaches have been proposed for molecular-based memory devices. While these approaches generally employ molecular architectures that can be switched between two different states, all of the approaches described to date have intrinsic limitations making their uses in computational devices difficult or impractical.

For example, such approaches to the production of molecular memories have involved photochromic dyes, electrochromic dyes, redox dyes, and molecular machines. Each of these approaches, however, has intrinsic limitations that ultimately render it unsuitable for use in molecular memories. For example, photochromic dyes change conformation in response to the absorption of light (e.g. cis-trans interconversion of an alkene, ring opening of a spiropyran, interconversion between excited-states in bacteriorhodopsin, etc.). Typically, the molecular structure of the dye is interconverted between two states that have distinct spectral properties.

Reading and writing data with such photochromic dyes requires use of light, often in the visible region (400–700 nm). Light-mediated data storage has intrinsic diffraction-limited size constraints. Moreover, most photochromic schemes are limited to scanning and interrogating dyes deposited on a surface and are not amenable to 3-D data storage. Even with near-field optical approaches, which might allow reliable encoding/reading of data elements of 100×100 nm dimensions (Nieto-Vesperinas and Garcia, N., eds. (1996) *Optics at the Nanometer Scale*, NATO ASI Series E, Vol. 319, Kluwer Academic Publishers: Dordrecht) the inherent restricted dimensionality (2-D) limits data density to $10^{10}$ bits/cm$^2$. Strategies for 3-dimensional reading and writing of photochromic systems have been proposed that rely on two-photon excitation of dyes to encode data, and one-photon excitation to read the data (Birge et al. (1994) *Amer. Sci.* 82: 349–355, Parthenopoulos and Rentzepis (1989) *Science*, 245: 843–845), but it is believed that no high-density memory cubes have reached prototype stage in spite of the passage of at least a decade since their initial proposition. In addition, it is noted that these dyes often exhibit relatively slow switching times ranging from microsecond to millisecond durations.

Electrochromic dyes have been developed that undergo a slight change in absorption spectrum upon application of an applied electric field (Liptay (1969) *Angew. Chem., Int. Ed. Engl.* 8: 177–188). The dyes must be oriented in a fixed direction with respect to the applied field. Quite high fields (>$10^7$ V/cm) must be applied to observe an altered absorption spectrum which can result in heat/power dissipation problems. In addition, the change in the absorption spectrum is typically quite small, which can present detection difficulties. The dyes revert to the initial state when the applied field is turned off.

Redox dyes have been developed that undergo a change in absorption spectrum upon chemical or electrochemical reduction (typically a 2-electron, 2-proton reduction) (Otsuki et al. (1996) *Chem. Lett.* 847–848). Such systems afford bistable states (e.g., quinone/hydroquinone, azo/hydrazo). Redox dyes have only been examined in solution studies, where they have been proposed for applications as switches and sensors (de Silva et al (1997) *Chem. Rev.* 97: 1515–1566). On a solid substrate, electrochemical reduction would need to be accompanied by a source of protons. The latter requirement may be difficult to achieve on a solid substrate. Furthermore, any optical reading scheme would pose the same 2-D limitations as described for photochromic dyes.

Yet another approach involves the design of molecular machines (Anell et al. (1992) *J. Am. Chem. Soc.* 114: 193–218). These elegant molecular architectures have moving parts that can be switched from one position to another by chemical or photochemical means. The chemically induced systems have applications as sensors but are not practical for memory storage, while the photochemically induced systems have the same fundamental limitations as photochromic dyes. Moreover, methods have not yet been developed for delineating the conformation/structure of the molecular machine that are practical in any device applications. $^1$H NMR spectroscopy, for example, is clearly the method of choice for elucidating structure/conformation for molecules in solution, but is totally impractical for interrogating a molecular memory element. None of the current architectures for molecular machines has been designed for assembly on a solid substrate, an essential requirement in a viable device.

In summary, photochromic dyes, electrochromic dyes, redox-sensitive dyes, and molecular machines all have fundamental limitations that have precluded their application as viable memory elements. These molecular architectures are typically limited by reading/writing constraints. Furthermore, even in cases where the effective molecular bistability is obtained, the requirement for photochemical reading restricts the device architecture to a 2-dimensional thin film. The achievable memory density of such a film is unlikely to exceed $10^{10}$ bits/cm$^2$. Such limitations greatly diminish the appeal of these devices as viable molecular memory elements.

SUMMARY OF THE INVENTION

This invention provides novel high density memory devices that are electrically addressable permitting effective reading and writing, that provide a high memory density (e.g., $10^{15}$ bits/cm$^3$), that provide a high degree of fault tolerance, and that are amenable to efficient chemical synthesis and chip fabrication. The devices are intrinsically latchable (e.g. have persistent states with a duration of up 10 to 15 minutes without a refresh cycle), defect tolerant, and support destructive or non-destructive read cycles.

In a preferred embodiment, this invention provides an apparatus for storing data (e.g., a "storage cell"). The storage cell includes a fixed electrode electrically coupled to a "storage medium" having a multiplicity of different and distinguishable oxidation states where data is stored in the (preferably non-neutral) oxidation states by the addition or withdrawal of one or more electrons from said storage medium via the electrically coupled electrode.

In previous embodiments, (see, e.g., copending U.S. Ser. Nos. 09/346,228 and 09/346,221, both filed on Jul. 1, 1999) the storage medium preferably utilized molecules employing weakly coupled arrays of porphyrins and/or porphyrinic macrocycles. The electrochemical potentials were tuned through the use of various substituents and central metals. The molecules retained their distinctive oxidation potentials when they were incorporated into arrays. Accordingly this approach typically involved the synthesis of a family of differently substituted porphyrins (or other molecules) for incorporation into a molecular array.

In order to simplify construction of the arrays for molecular based information storage, this invention describes the use of polymeric molecules having multiple oxidation states where the monomeric subunits comprising the polymers are tightly coupled (e.g. directly linked as opposed to linking through a linker). The "tight coupling" is manifested as a splitting in redox potentials of the structurally identical subunits. Thus, for example, combination of two identical subunits each having two identical non-zero oxidation states can result in a dimer having four different and distinguishable non-zero oxidation states. This greatly simplifies fabrication of a storage molecule as, in this instance, only a single type of subunit need be synthesized.

Thus, in one embodiment, this invention provides an apparatus for storing data. The apparatus comprises a fixed electrode electrically coupled to a storage medium comprising a storage molecule having a first subunit and a second subunit (i.e. at least two subunits) wherein the first and second subunits are tightly coupled such that oxidation of the first subunit alters the oxidation potential of the second subunit. In preferred embodiments, the subunits are a porphyrinic macrocycle, a metallocene, a linear polyene, a cyclic polyene, a heteroatom-substituted linear polyene, a heteroatom-substituted cyclic polyene, a tetrathiafulvalene, a tetraselenafulvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, or a peri-bridged naphthalene dichalcogenide. In particularly preferred embodiments, the subunits are both porphyrinic macrocycles (e.g. both porphyrins) or metallocenes (e.g. both ferrocenes) and most preferably essentially identical (optionally differing only in the presence or absence of a linker).

In one embodiment, a pair of the tightly coupled subunits has the following structure:

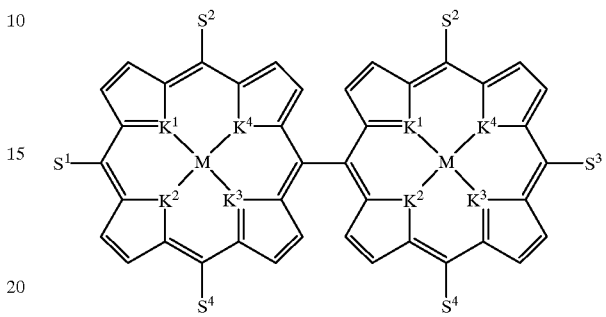

wherein $S^1$, $S^2$, S3, and $S^4$ are substituents independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts; or one or more of $S^1$, $S^2$, $S^3$, $S^4$ are optionally another subunit or optionally -L-X where -L-X, when present, is optionally present on one or both subunits and L, when present, is a linker; and X, whein present, is selected from the group consisting of a substrate, a reactive site that can covalently couple to a substrate (e.g., $SCOR^1$, and $SCON(R^2)(R^3)$, wherein $R^1$, $R^2$, and $R^3$ are independently selected groups, more preferably SCN, SCONH(Et), $SCOCH_3$, or SH, and a reactive site that can ionically couple to a substrate; M is a metal (e.g., Zn, Mg, Cd, Hg, Cu, Ag, Au, Ni, Pd, Pt, Co, Rh, Ir, Mn, B, Al, Pb, Ga, Fe, or Sn, more preferably Zn, Mg, or (H,H)); $K^1$, $K^2$, $K^3$, and $K^4$ are independently selected from the group consisting of N, O, S, Se, Te, and CH. In a preferred embodiment, $S^1$, $S^2$, and $S^3$ are independently selected from the group consisting of mesityl, $C_6F_5$, 2,4,6-trimethoxyphenyl, phenyl, p-tolyl, p-(tert-butyl)phenyl, 3,5-dimethylphenyl, 3,5-di(tert-butyl)phenyl, 3,5-dimethoxyphenyl, 3,5-dialkoxyphenyl, and n-pentyl.

In one preferred embodiment, second subunit can be oxidized by a voltage difference no greater than about 2 volts. In certain embodiments, -L-X is 4-(2-(4-mercaptophenyl)ethynyl)phenyl, 4-mercaptomethylphenyl, 4-hydroselenophenyl, 4-(2-(4-hydroselenophenyl)ethynyl) phenyl, 4-hydrotellurophenyl, 2-(4-mercaptophenyl) ethynyl, 2-(4-hydroselenophenyl)ethynyl, 2-(4-hydrotellurophenyl)ethynyl, or 4-(2-(4-hydrotellurophenyl) ethynyl)phenyl.

In some embodiments, $S^1$ and $S^3$ are both the same; and $K^1$, $K^2$, $K^3$, and $K^4$ are all the same. In one such embodiment, M is Zn; and $K^1$, $K^2$, $K^3$, and $K^4$ are all N. Particular preferred species are illustrated by Formulas III, IV, V, and VI herein.

In various embodiments, the storage medium has at least four, more preferably at least 6 and most preferably at least 8 different and distinguishable non-neutral oxidation states.

The storage molecule can be directly covalently linked to the electrode or covalently linked through a linker (e.g., a thiol linker). In another embodiment, the storage medium is juxtaposed in the proximity of said electrode such that electrons can pass from said storage medium to said electrode. The storage medium can be juxtaposed to (or embedded in) a dielectric material imbedded with counterions. In some embodiments, the storage medium and said electrode are fully encapsulated in an integrated circuit. The storage medium can be electronically coupled to a second fixed electrode that is a reference electrode. In one architecture, the storage medium is present on a single plane in said device, while in another architecture, the storage medium is present at a multiplicity of storage locations. The apparatus may comprise multiple planes and the storage locations may be present on multiple planes of the device. In preferred devices, the storage locations range from about 1024 to about 4096 different locations. Each location can be addressed by a single electrode or each location can be addressed by two (or more) electrodes. Typically at least one electrode is connected to a voltage source (e.g. the output of an integrated circuit).

Typically at least one electrode is connected to a device (e.g. a voltammetric device, an amperometric device, or a potentiometric device) to read the oxidation state of the storage medium. Preferred devices include, but are not limited to an impedance spectrometer or a sinusoidal voltammeter. The device can optionally provides a Fourier transform of the output signal from the electrode. The device can also optionally refresh the oxidation state of said storage medium after reading the oxidation state.

Particularly preferred methods and/or devices of this invention utilize a "fixed" electrode. Thus, in one embodiment, methods and/or devices in which the electrode(s) are moveable (e.g. one or ore electrodes is a "recording head", the tip of a scanning tunneling microscope (STM), the tip of an atomic force microscope (AFM), or other forms in which the electrode is movable with respect to the storage medium are excluded. In certain embodiments, methods and/or devices and/or storage media, and/or storage molecules in which the storage molecule is an alkanethiolferrocene are excluded. Similarly in certain embodiments, methods and/or devices and/or storage media, in which the storage molecules are responsive to light and/or in which the oxidation state of a storage molecule is set by exposure to light are excluded.

In another embodiment, this invention provides an information storage medium. The information storage medium can be used to assemble storage cells and/or the various memory devices described herein. In a preferred embodiment the storage medium comprises one or more different storage molecules. The storage medium has at least two (preferably at least four, more preferably at least 8 or 16) different and distinguishable non-neutral oxidation states. The storage molecule(s) in the storage medium comprise a first subunit and a second subunit where the first and second subunits are tightly coupled such that oxidation of the first subunit alters the oxidation potential of the second subunit, where the subunits are selected from the group consisting of a porphyrinic macrocycle and a metallocene and the molecule has at least two different non-zero oxidation states and the oxidation states are within a redox potential range of less than about 2 volts. The subunits are preferably both metallocenes (e.g. ferrocenes) or both porphyrinic macrocycles (e.g. porphyrins). Particularly preferred molecules comprise a pair of tightly coupled subunits having the structures described herein.

This invention also provides particularly preferred molecules for the storage of information (storage molecules) as described herein.

This invention also provides methods of storing data. The methods involve i) providing an apparatus, e.g., comprising one or more storage cells as described herein; and ii) applying a voltage to the electrode at sufficient current to set an oxidation state of said storage medium (the storage medium comprising one or more storage cells). In preferred embodiments, the voltage ranges is less than about 5 volts, more preferably less than about 2 volts, and most preferably less than about 1 or less than about 0.5 volts. The voltage can be the output of any convenient voltage source (e.g. output of an integrated circuit, power supply, logic gate, potentiostat, microprocessor (CPU), etc.) that can provide a voltage/signal for writing, reading, or refreshing the storage cell(s).

The method can further involve detecting the oxidation state of the storage medium and thereby reading out the data stored therein. The detection (read) can optionally involve refreshing the oxidation state of the storage medium. The read (detecting) can involve analyzing a readout signal in the time or frequency domain and can thus involve performing a Fourier transform on the readout signal. The detection can be by any of a variety of methods including, but not limited to, a voltammetric method. In preferred embodiments, the storage cells used in the methods of this invention have storage media comprising one or more of the storage molecules described herein This invention additionally provides the memory devices of this invention (e.g. memory cells) in a computer system. Preferred computer systems include a central processing unit, optionally a display, optionally a selector device, and a memory device (e.g., the storage devices (e.g. storage cells) of this invention).

DEFINITIONS

The term "oxidation" refers to the loss of one or more electrons in an element, compound, or chemical substituent/subunit. In an oxidation reaction, electrons are lost by atoms of the element(s) involved in the reaction. The charge on these atoms must then become more positive. The electrons are lost from the species undergoing oxidation and so electrons appear as products in an oxidation reaction. An oxidation is taking place in the reaction $Fe^{2+}(aq) \rightarrow Fe^{3+}(aq)+e^-$ because electrons are lost from the species being oxidized, $Fe^{2+}(aq)$, despite the apparent production of electrons as "free" entities in oxidation reactions. Conversely the term reduction refers to the gain of one or more electrons by an element, compound, or chemical substituent/subunit.

An "oxidation state" refers to the electrically neutral state or to the state produced by the gain or loss of electrons to an element, compound, or chemical substituent/subunit. In a preferred embodiment, the term "oxidation state" refers to states including the neutral state and any state other than a neutral state caused by the gain or loss of electrons (reduction or oxidation).

The term "multiple oxidation states" means more than one oxidation state. In preferred embodiments, the oxidation states may reflect the gain of electrons (reduction) or the loss of electrons (oxidation).

The terms "different and distinguishable" when referring to two or more oxidation states mean that the net charge on the entity (atom, molecule, aggregate, subunit, etc.) can exist in two different states. The states are said to be "distinguishable" when the difference between the states is greater than thermal energy at room temperature (e.g. 0° C. to about 40° C.).

The term "tightly coupled" when used in reference to a subunit of a multi-subunit (e.g., polymeric) storage molecule of this invention refers to positioning of the subunits relative to each other such that oxidation of one subunit alters the oxidation potential(s) of the other subunit. In a preferred embodiment the alteration is sufficient such that the (non-neutral) oxidation state(s) of the second subunit are different and distinguishable from the non-neutral oxidation states of the first subunit. In a preferred embodiment the tight coupling is achieved by a covalent bond (e.g. single, double, triple, etc.). However, in certain embodiments, the tight coupling can be through a linker, via an ionic interaction, via a hydrophobic interaction, through coordination of a metal, or by simple mechanical juxtaposition. It is understood that the subunits could be so tightly coupled that the redox processes are those of a single supermolecule.

The term "electrode" refers to any medium capable of transporting charge (e.g. electrons) to and/or from a storage molecule. Preferred electrodes are metals or conductive organic molecules. The electrodes can be manufactured to virtually any 2-dimensional or 3-dimensional shape (e.g. discrete lines, pads, planes, spheres, cylinders, etc.).

The term "fixed electrode" is intended to reflect the fact that the electrode is essentially stable and unmovable with respect to the storage medium. That is, the electrode and storage medium are arranged in an essentially fixed geometric relationship with each other. It is of course recognized that the relationship alters somewhat due to expansion and contraction of the medium with thermal changes or due to changes in conformation of the molecules comprising the electrode and/or the storage medium. Nevertheless, the overall spatial arrangement remains essentially invariant. In a preferred embodiment this term is intended to exclude systems in which the electrode is a movable "probe" (e.g. a writing or recording "head", an atomic force microscope (AFM) tip, a scanning tunneling microscope (STM) tip, etc.).

The term "working electrode" is used to refer to one or more electrodes that are used to set or read the state of a storage medium and/or storage molecule.

The term "reference electrode" is used to refer to one or more electrodes that provide a reference (e.g. a particular reference voltage) for measurements recorded from the working electrode. In preferred embodiments, the reference electrodes in a memory device of this invention are at the same potential although in some embodiments this need not be the case.

The term "electrically coupled" when used with reference to a storage molecule and/or storage medium and electrode refers to an association between that storage medium or molecule and the electrode such that electrons move from the storage medium/molecule to the electrode or from the electrode to the storage medium/molecule and thereby alter the oxidation state of the storage medium/molecule. Electrical coupling can include direct covalent linkage between the storage medium/molecule and the electrode, indirect covalent coupling (e.g. via a linker), direct or indirect ionic bonding between the storage medium/molecule and the electrode, or other bonding (e.g. hydrophobic bonding). In addition, no actual bonding may be required and the storage medium/molecule may simply be contacted with the electrode surface. There also need not necessarily be any contact between the electrode and the storage medium/molecule where the electrode is sufficiently close to the storage medium/molecule to permit electron tunneling between the medium/molecule and the electrode.

The term "redox-active unit" or "redox-active subunit" refers to a molecule or component of a molecule that is capable of being oxidized or reduced by the application of a suitable voltage.

The term "subunit", as used herein, refers to a redox-active component of a molecule.

The terms "storage molecule" or "memory molecule" refer to a molecule having one or more oxidation states that can be used for the storage of information (e.g. a molecule comprising one or more redox-active subunits). Preferred storage molecules have two or more different and distinguishable non-neutral oxidation states.

The term "storage medium" refers to a composition comprising two or more storage molecules. The storage medium can contain only one species of storage molecule or it can contain two or more different species of storage molecule.

The term "storage medium" as used herein refers to a collection of storage molecules. Preferred storage media comprise a multiplicity (at least 2) of different and distinguishable (preferably non-neutral) oxidation states. The multiplicity of different and distinguishable oxidation states can be produced by the combination of different species of storage molecules, each species contributing to said multiplicity of different oxidation states and each species having a single non-neutral oxidation state. Alternatively or in addition, the storage medium can comprise one or more species of storage molecule having a multiplicity of non-neutral oxidation states. The storage medium can contain predominantly one species of storage molecule or it can contain a number of different storage molecules. The storage media can also include molecules other than storage molecules (e.g. to provide chemical stability, suitable mechanical properties, to prevent charge leakage, etc.).

The term "electrochemical cell" consists minimally of a reference electrode, a working electrode, a redox-active medium (e.g. a storage medium), and, if necessary, some means (e.g., a dielectric) for providing electrical conductivity between the electrodes and/or between the electrodes and the medium. In some embodiments, the dielectric is a component of the storage medium.

The terms "memory element", "memory cell", or "storage cell" refer to an electrochemical cell that can be used for the storage of information. Preferred "storage cells" are discrete regions of storage medium addressed by at least one and preferably by two electrodes (e.g. a working electrode and a reference electrode). The storage cells can be individually addressed (e.g. a unique electrode is associated with each memory element) or, particularly where the oxidation states of different memory elements are distinguishable, multiple memory elements can be addressed by a single electrode. The memory element can optionally include a dielectric (e.g. a dielectric impregnated with counterions).

The term "storage location" refers to a discrete domain or area in which a storage medium is disposed. When addressed with one or more electrodes, the storage location may form a storage cell. However if two storage locations contain the same storage media so that they have essentially the same oxidation states, and both storage locations are commonly addressed, they may form one functional storage cell.

Addressing a particular element refers to associating (e.g., electrically coupling) that memory element with an electrode such that the electrode can be used to specifically determine the oxidation state(s) of that memory element.

The term "storage density" refers to the number of bits per volume and/or bits per molecule that can be stored. When the storage medium is said to have a storage density greater than one bit per molecule, this refers to the fact that a storage medium preferably comprises molecules wherein a single molecule is capable of storing at least one bit of information.

The terms "read" or "interrogate" refer to the determination of the oxidation state(s) of one or more molecules (e.g. molecules comprising a storage medium).

The term "refresh" when used in reference to a storage molecule or to a storage medium refers to the application of a voltage to the storage molecule or storage medium to re-set the oxidation state of that storage molecule or storage medium to a predetermined state (e.g. an oxidation state the storage molecule or storage medium was in immediately prior to a read).

The term "$E_{1/2}$" refers to the practical definition of the formal potential ($E^{\circ}$) of a redox process as defined by $E=E^{\circ}+(RT/nF)\ln(D_{ox}/D_{red})$ where R is the gas constant, T is temperature in K (Kelvin), n is the number of electrons involved in the process, F is the Faraday constant (96,485 Coulomb/mole), $D_{ox}$ is the diffusion coefficient of the oxidized species and $D_{red}$ is the diffusion coefficient of the reduced species.

A voltage source is any source (e.g. molecule, device, circuit, etc.) capable of applying a voltage to a target (e.g. an electrode).

The term "present on a single plane", when used in reference to a memory device of this invention refers to the fact that the component(s) (e.g. storage medium, electrode (s), etc.) in question are present on the same physical plane in the device (e.g. are present on a single lamina). Components that are on the same plane can typically be fabricated at the same time, e.g., in a single operation. Thus, for example, all of the electrodes on a single plane can typically be applied in a single (e.g., sputtering) step (assuming they are all of the same material).

The phrase "output of an integrated circuit" refers to a voltage or signal produced by a one or more integrated circuit(s) and/or one or more components of an integrated circuit.

A "voltammetric device" is a device capable of measuring the current produced in an electrochemical cell as a result of the application of a voltage or change in voltage.

An "amperometric device" is a device capable of measuring the current produced in an electrochemical cell as a result of the application of a specific potential field potential ("voltage").

A potentiometric device is a device capable of measuring potential across an interface that results from a difference in the equilibrium concentrations of redox molecules in an electrochemical cell.

A "coulometric device" is a device capable of the net charge produced during the application of a potential field ("voltage") to an electrochemical cell.

An impedance spectrometer is a device capable of determining the overall impedance of an electrochemical cell.

A "sinusoidal voltammeter" is a voltammetric device capable of determining the frequency domain properties of an electrochemical cell.

The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-, β) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g. phthalocyanines, sub-phthalocyanines, and porphyrin isomers). Preferred porphyrinic macrocycles comprise at least one 5-membered ring.

The term porphyrin refers to a cyclic structure typically composed of four pyrrole rings together with four nitrogen atoms and two replaceable hydrogens for which various metal atoms can readily be substituted. A typical porphyrin is hemin.

The term "multiporphyrin array" refers to a discrete number of two or more covalently-linked porphyrinic macrocycles. The multiporphyrin arrays can be linear, cyclic, or branched.

A linker is a molecule used to couple two different molecules, two subunits of a molecule, or a molecule to a substrate.

A substrate is a, preferably solid, material suitable for the attachment of one or more molecules. Substrates can be formed of materials including, but not limited to glass, plastic, silicon, minerals (e.g. quartz), semiconducting materials, ceramics, metals, etc.

The term "odd hole oxidation state", refers to the case where the number of electron equivalents added or removed from a molecule or molecules is not an integer multiple of the number of redox-active (e.g. oxidizable or reducable) subunits in the molecule or molecules.

The phrase "hole hopping" refers to the exchange of oxidation states between subunits of thermodynamically similar potentials.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl ($C_6H_5$) or naphthyl ($C_{10}H_7$). It is recognized that the aryl group, while acting as substituent can itself have additional substituents (e.g. the substituents provided for $S''$ in the various Formulas herein).

The term "alkyl" refers to a paraffinic hydrocarbon group which may be derived from an alkane by dropping one hydrogen from the formula. Examples are methyl ($CH_3$—), ethyl ($C_2H_5$—), propyl ($CH_3CH_2CH_2$—), isopropyl (($CH_3$)$_2$CH).

The term "halogen" refers to one of the electronegative elements of group VIIA of the periodic table (fluorine, chlorine, bromine, iodine, astatine).

The term "nitro" refers to the —$NO_2$ group.

The term "amino" refers to the —$NH_2$ group.

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CH unit is replaced with a nitrogen atom.

The term "cyano" refers to the —CN group.

The term "thiocyanato" refers to the —SCN group.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not limited to methylsulfonyl, phenylsulfonyl, p-toluenesulfonyl, etc.

The term "carbamoyl" refers to the group of composition $R^1(R^2)NC(O)$— where $R^1$ and $R^2$ are H or some alkyl, aryl, cycloalkyl, perfluoroalkyl, or perfluoroaryl group. Examples include, but are not limited to N-ethylcarbamoyl, N,N-dimethylcarbamoyl, etc.

The term "amido" refers to the group of composition $R^1CON(R^2)$— where $R^1$ and $R^2$ are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the OH of the carboxyl group is replaced by some other substituent (RCO—). Examples include, but are not limited to acetyl, benzoyl, etc In preferred embodiments, when a metal is designated by "M" or "$M^n$", where n is an integer, it is recognized that the metal may be associated with a counterion.

The term "substituent" as used in the formulas herein, particularly designated by S or $S^n$ where n is an integer, in a preferred embodiment refers to redox-active groups (subunits) that can be used to adjust the redox potential(s) of the subject compound. Preferred substituents include, but are not limited to, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In preferred embodiments, a substituted aryl group is attached to a porphyrin or a porphyrinic macrocycle, and the substituents on the aryl group are selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl.

Particularly preferred substituents include, but are not limited to, 4-chlorophenyl, 3-acetamidophenyl, 2,4-dichloro-4-trifluoromethyl). Preferred substituents provide a redox potential range of less than about 5 volts, preferably less than about 2 volts, more preferably less than about 1 volt.

The phrase "provide a redox potential range of less than about X volts" refers to the fact that when a substituent providing such a redox potential range is incorporated into a compound, the compound into which it is incorporated has an oxidation potential less than or equal to X volts, where X is a numeric value.

The terms "SHSU", "SHMU" and "DHMU", refer to "static-hole single unit", static-hole multi-unit" and dynamic hole multi-unit", respectively, as described in copending applications U.S. Ser. Nos. 09/346,228 and 09/346,221, both filed on Jul. 1, 1999.

DETAILED DESCRIPTION

Figure 1:
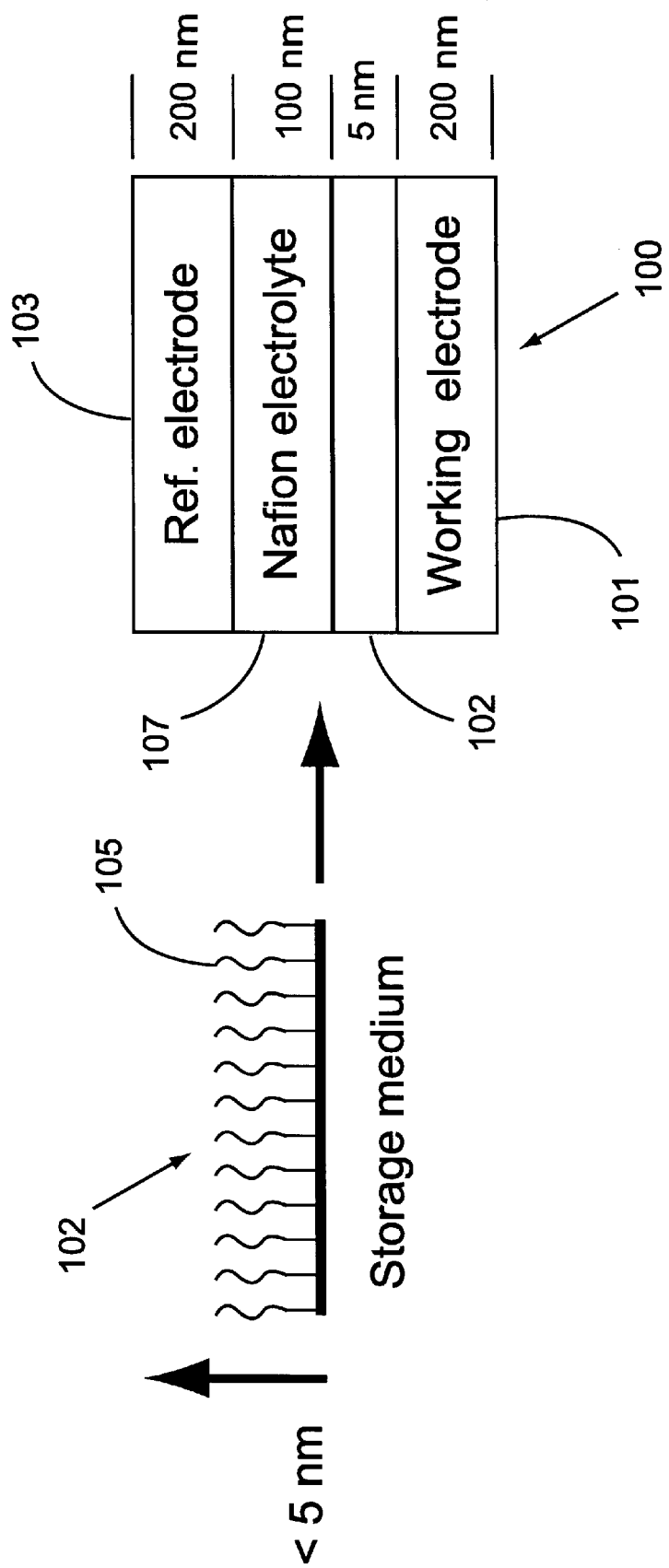
FIG. 1 illustrates a basic molecular memory unit "storage cell" of this invention. The basic memory device, a "storage cell" 100 comprises a working electrode 101 electrically coupled to a storage medium 102 comprising a multiplicity of storage molecules 105. The storage cell optionally includes an electrolyte 107 and a reference electrode 103. The storage medium has a multiplicity of different and distinguishable oxidation states, preferably a multiplicity of different and distinguishable non-neutral oxidation states, and can change oxidation (charge) state when a voltage or signal is applied thereby adding or removing one or more electrons.

This invention provides novel high density memory devices that are electrically addressable permitting effective reading and writing, that provide a high memory density (e.g., $10^{15}$ bits/cm$^3$), that provide a high degree of fault tolerance, and that are amenable to efficient chemical synthesis and chip fabrication. The devices are intrinsically latchable, defect tolerant, and support destructive or non-destructive read cycles.

In a preferred embodiment, this invention provides an apparatus for storing data (e.g., a "storage cell"). The storage cell includes a fixed electrode electrically coupled to a "storage medium" having a multiplicity of different and distinguishable oxidation states where data is stored in the (preferably non-neutral) oxidation states by the addition or withdrawal of one or more electrons from said storage medium via the electrically coupled electrode.

In previous embodiments, (see, e.g., U.S. Ser. Nos. 09/346,228 and 09/346,221, both filed on Jul. 1, 1999) the storage medium preferably utilized molecules employing weakly coupled arrays of porphyrins and/or porphyrinic macrocycles. The electrochemical potential was tuned through the use of various substituents and central metals. The molecules retained their distinctive oxidation potentials when they were incorporated into arrays. Accordingly this approach typically involved the synthesis of a family of differently substituted porphyrins (or other molecules) for incorporation into a molecular array.

In order to simplify construction of the arrays for molecular based information storage, this invention describes the use of polymeric molecules having multiple oxidation states where the monomeric subunits comprising the polymers are tightly coupled (e.g. directly linked as opposed to linking through a linker). The "tight coupling" is manifested as a splitting in redox potentials of the structurally identical subunits. Thus, for example, combination of two identical subunits each having two identical non-zero oxidation states can result in dimer having four different and distinguishable non-zero oxidation states. This greatly simplifies fabrication of a storage molecule as, in this instance, only a single type of subunit need be synthesized.

I. Use of Tightly Coupled Subunits to Form a Storage Molecule

As indicated above, the use of tightly coupled subunits permits the creation of a storage molecule/storage medium having multiple different and distinguishable non-neutral oxidation states. In particular, the juxtaposition of the subunits at a spacing that permits strong (tight) coupling between the two subunits results in a splitting of the redox potentials of the structurally identical units. In this manner, identical porphyrins can be used in the construction of a storage molecule capable of storing many bits of information thereby resulting in substantial efficiencies in the construction of storage media.

This is illustrated with respect to a porphyrin. A monomeric porphyrin has three accessible oxidation states (neutral, mono-cation, dication), the precise level of which can be tuned through synthetic variation of peripheral substituents, central metal, and use of skeletal atoms other than nitrogen.

One example of a tightly coupled dimeric porphyrin array that we have investigated is shown below in Formula I (porphyrin dimer 1). This molecule has two zinc porphyrins linked to each other at the porphyrin meso-positions.

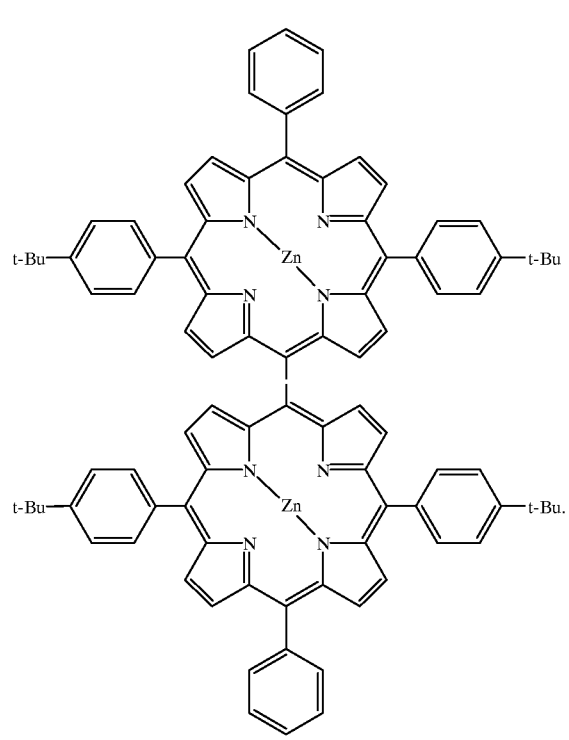

I

The synthesis of this porphyrin dimer was accomplished using methods for preparing building block porphyrins (Cho et al. (1999) *J. Org. Chem.* 64: 7890–7901).

Electrochemical examination of porphyrin dimer I revealed oxidation waves at +0.49 and +0.66 V for the formation of the monocation of the two porphyrins comprising the porphyrin dimer. This is in contrast to the single oxidation wave for the corresponding porphyrin monomer which is expected at +0.58 V. The appearance of two waves in porphyrin dimer I indicates that the oxidation of the first porphyrin forming the monocation shifts the potential of the second porphyrin to higher potential. This shift in potential provides the opportunity to access distinct and different oxidation potentials in a multiporphyrin array where each porphyrin is identical. In this example, the porphyrin dimer I has four non-zero oxidation states as illustrated in Table 1.

TABLE 1

Oxidation potentials observed in porphyrin dimer I.

| Oxidation potential (V) | Redox-active unit |
| --- | --- |
| 0.49 | dimer oxidation potential 1 |
| 0.66 | dimer oxidation potential 2 |
| 0.95 | dimer oxidation potential 3 |
| 1.03 | dimer oxidation potential 4 |

In this example, four different and distinguishable non-zero oxidation states are available in the resulting dimer, but construction of the storage molecule required synthesis of only a single subunit (porphyrin monomer). This dramatically reduces the complexity and cost of the creation of suitable storage molecules for use in the storage devices of this invention.

The principle is generalizable. One is not limited to the construction of tightly coupled dimers. It is also possible to construct tightly coupled trimers and longer oligomers having more different and distinguishable oxidation states.

In addition, the constituent subunits need not be limited to porphyrins.

Essentially any molecule that has multiple different and distinguishable oxidation states and that can be tightly coupled to produce molecules having even more different and distinguishable oxidation states can be used as a subunit. Such molecules include, but are not limited to a porphyrinic macrocycle, a metallocene (e.g. a ferrocene), a linear polyene, a cyclic polyene, a heteroatom-substituted linear polyene, a heteroatom-substituted cyclic polyene, a tetrathiafulvalene, a tetraselenafulvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, a peri-bridged naphthalene dichalcogenide, and the like.

A pair of subunits is said to be strongly coupled when coupling of the subunits (e.g. porphyrins) increases the number of distinct and distinguishable oxidation states above the number of oxidation states available in the separate pair of subunits. In the case of the dimer of Formula I, the two separate subunits each have one non-zero oxidation state, but the dimer has four non-zero oxidation states and is thus essentially strongly coupled for the purposes of this invention.

Tight coupling is typically achieved by directly covalently linking the two subunits. In certain, instances, however, the subunits may be joined by a linker and/or joined by coordination to a metal, as long as the subunits are positioned closely enough together that they are functionally "tightly coupled." One example of subunits tightly coupled by coordination to a metal is provided by the lanthanide porphyrinic "sandwich" molecules. These include, but are not limited to, a variety of double-decker and triple-decker sandwich molecules comprised of porphyrinic molecules and metals (e.g. metals of the lanthanide series such as La, Ce, Pr, Nd, Pm, Sm, Eu, Gd, Tb, Dy, Ho, Er, Tm, Yb, Lu and Y which has properties similar to lanthanides) (see, e.g., Jiang et al. (1997) *Inorg. Chim. Acta*, 255: 59–64; Ng and Jiang (1997) *J. Chem. Soc. Rev.*, 26: 433–442; Chabach et al. (1996) *Angew. Chem. Int. Ed. Engl.*, 35: 898–899). Sandwich structures have also been made using Zr, Hf, Th, and U.

Methods of determining when molecules are tightly coupled are well known to those of skill in the art. Using optical spectrographic methods, tightly coupled molecules will be revealed as perturbations in the optical spectra of the tightly coupled molecule. Thus, typically when an electron is removed from the system it will typically be accompanied an electronic transition (mixed valence transition).

Similarly when examining the vibrational spectrum of the system (e.g. via infrared or raman spectroscopy) a weakly coupled system shows a neutral and a cation signature. As the system becomes more tightly coupled, the neutral and cation signature diminish and the system shows a characteristic signature at a frequency between the neutral and the cation frequency (Donohoe et al. (1988) *J. Am. Chem. Soc.*, 110: 6119–6124). It is understood that the subunits could be so tightly coupled that the redox processes are those of a single supermolecule.

In a preferred embodiment, the system is designed to provide multiple distinct and distinguishable oxidation states in a redox potential range of less than about 5 volts, preferably less than about 2 volts, more preferably less than about 1 volt. While the oxidation states are different and distinguishable at a difference of at least 1 mV, preferably at least 5 mV, and more preferably at least 10 mV, in particularly preferred embodiments, the oxidation states are separated from each other by at least about 25 mV, preferably by at least 50 mV, more preferably by at least about 100 mV, and most preferably by at least about 130–150 mV.

II. Architecture of the Storage Medium and Tightly Coupled Storage Molecules

The storage medium used in the devices of this invention comprises one or more species of storage molecule. A preferred storage medium is characterized by having a multiplicity of oxidation states. Those oxidation states are provided by one or more redox-active units. A redox-active unit refers to a molecule or to a subunit of a molecule that has one or more discrete oxidation states that can be set by application of an appropriate voltage. Thus, for example, in one embodiment, the storage medium can comprise one species of redox-active molecule where that molecule has two or more (e.g. 8) different and distinguishable oxidation states. Typically, but not necessarily, such multi-state molecules will be composed of several redox-active units (e.g. porphyrins or ferrocenes). In another exemplary embodiment, the storage medium can comprise two or more different species of storage molecule. Each storage molecule comprises at least one redox-active unit, but can easily contain two or more redox-active units. Where each species of storage molecule has a single, non-neutral, oxidation state, the storage medium achieves multiple bit storage by having a plurality of such molecules where each molecule has a different and distinguishable oxidation state (e.g. each species of molecule oxidizes at a different and distinguishable potential). Of course, each species of molecule can have a multiplicity of different and distinguishable oxidation states. Thus, a storage medium comprising eight different species of storage molecule where each of the eight species has eight different and distinguishable oxidation states, will be able to store 64 (8×8) bits of information.

As indicated below, in the devices of this invention, the storage medium can be broken down into individual, e.g., spatially segregated, storage locations. Each storage element can have a storage medium that is the same or different from the other storage elements in the chip and/or system. Where the storage elements are of identical composition, in preferred embodiments, they are separately addressed so that information in one element can be distinguished from information in another element. Where the storage elements are of different composition they can be commonly addressed (where the oxidation states of the commonly addressed storage elements are distinguishable) or they can be individually addressed.

In certain preferred embodiments the storage medium is juxtaposed to a dielectric medium to insure electrical connectivity to a reference voltage (e.g. a reference electrode, a reference backplane, etc.). In particularly preferred embodiments, a layer of dielectric material imbedded with counterions to ensure electrical connectivity to the reference electrode and stability of the cationic species in the absence of applied potential (latching), is disposed between the reference working electrode(s).

Dielectric materials suitable for the devices of this invention are well known to those of skill in the art. Such materials include, but are not limited to Nafion™, cellulose acetate, polystyrene sulfonate, poly(vinylpyridine), electronically conducting polymers such as polypyrrole and polyaniline, etc.

In preferred embodiments, the storage molecules of this invention, are polymeric molecules comprising two or more monomeric subunits. In preferred embodiments the subunits are identical or perhaps differ only in the presence or absence of a linker for attachment to the electrode. Use of essentially identical subunits substantially reduces the synthetic chemistry required to produce a storage device resulting in substantially more efficient and less error-prone device assembly and substantial savings of labor and cost.

In a preferred embodiment, the subunits (monomers comprising the multimeric (array) molecule are porphyrinic macrocycles or metallocenes with porphyrinic macrocycles being most preferred. The porphyrinic macrocycles identified herein are ideally suited for molecular based memory storage. The porphyrinic macrocycles, and especially the porphyrins, have unique electroactive properties, a well-developed modular synthetic chemistry, and in conjunction with thiols, and other linkers described herein, undergo directed self-assembly on electroactive surfaces.

In particularly preferred embodiments, a pair of the tightly coupled subunits has the following structure shown in Formula II:

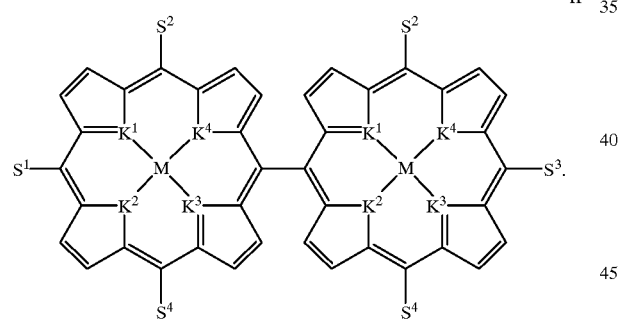

II where $S^1$, $S^2$, $S^3$, and $S^4$ are substituents independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl and the substituents provide a redox potential range of less than about 2 volts. Alternatively, one or more of $S^1$, $S^2$, $S^3$, and $S^4$ are -L-X where -L-X, when present is optionally present on one or both subunits and L, when present, is a linker; X is selected from the group consisting of a substrate, a reactive site that can covalently couple to a substrate, and a reactive site that can ionically couple to a substrate; M is a metal; and $K^1$, $H^2$, $H^3$, and $K^4$ are independently selected from the group consisting of N, O, S, Se, Te, and CH. In certain preferred embodiments, $S^1$, $S^2$, and $S^3$ are independently selected from the group consisting of mesityl, $C_6F_5$, 2,4,6-trimethoxyphenyl, phenyl, p-tolyl, p-(tert-butyl)phenyl, 3,5-dimethylphenyl, 3,5-di(tert-butyl)phenyl, 3,5-dimethoxyphenyl, 3,5-dialkoxyphenyl, and n-pentyl. In certain preferred embodiments, -L-X is selected from the group consisting 4-(2-(4-mercaptophenyl)ethynyl)phenyl, 4-mercaptomethylphenyl, 4-hydroselenophenyl, 4-(2-(4-hydroselenophenyl)ethynyl)phenyl, 4-hydrotellurophenyl, 2-(4-mercaptophenyl)ethynyl, 2-(4-hydroselenophenyl)ethynyl, 2-(4-hydrotellurophenyl)ethynyl, and 4-(2-(4-hydrotellurophenyl)ethynyl)phenyl. Of course, the molecule need not be a dimmer, in which case one or more of $S^1$, $S^2$, $S^3$, or $S^4$ can independently be another subunit.

In a particularly preferred embodiment, $S^1$ and $S^3$ are both the same; and $K^1$, $K^2$, $K^3$, and $K^4$ are all the same (e.g. N). Various preferred embodiments are listed above in Formula I and below in Formulas III, IV, V, and VI.

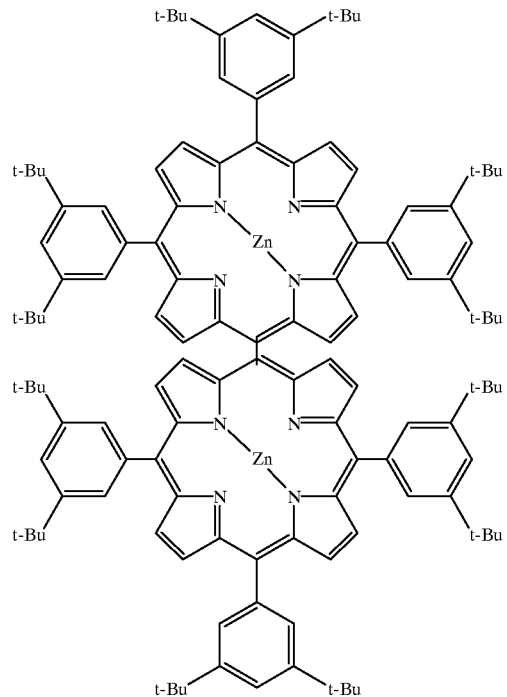

III

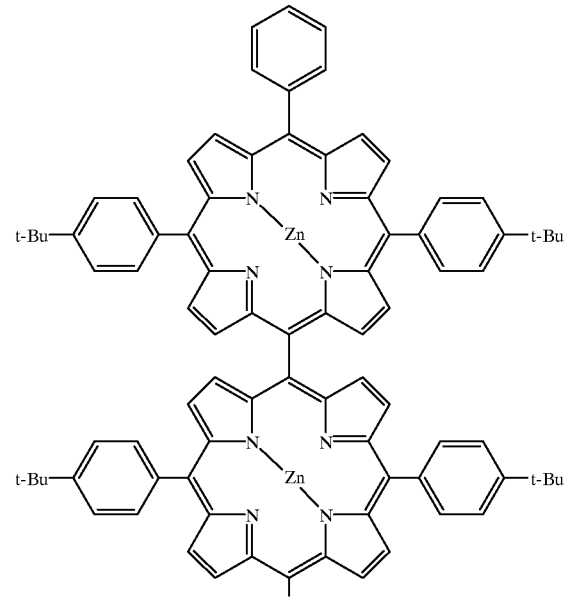

IV

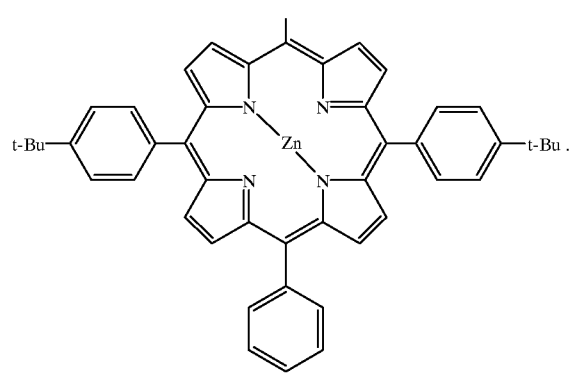
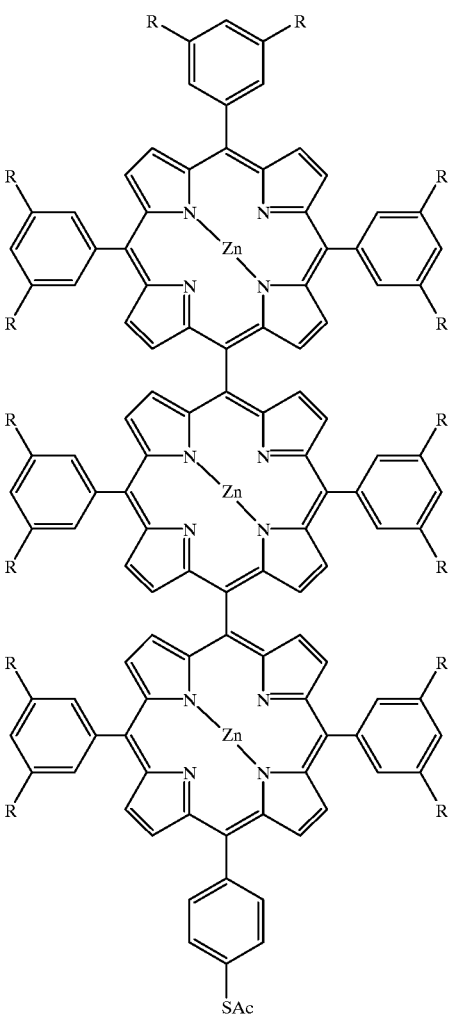
Information is stored in the storage molecule by removing electrons from the porphyrin constituents (leaving a hole and forming a π-cation radical (Strachan et al. (1997) *J. Am. Chem. Soc.*, 119: 11191–11201; Li et al. (1997) *J. Mater.*

Chem. 7: 1245–1262, and Seth et al. (1996) *J. Am. Chem. Soc.* 118: 11194–11207; Seth et al. (1994) *J. Am. Chem. Soc.* 116: 10578–10592). The redox characteristics of the subunits are adjusted by selection of the metal (M) and the substituents (e.g. $S^1$, $S^2$, $S^3$).

The synthetic methodologies already established permit the extension of the linear architecture, thus increasing the dynamic range of this basic memory element well beyond the four bits indicated in Table I. In addition, subunits can be engineered that have more than two oxidation states and more complex subunits can be utilized (e.g. subunits each comprising a porphyrinic macrocycle coupled to a metallocene). Thus for example, molecules and/or subunits can be engineered that have virtually any number (e.g., 2, 4, 8, 16, 32, 64, 128, etc.) of different and distinguishable oxidation states.

III. Synthesis and Characterization of Storage Medium Molecule(s)

A) Designing Oxidation States into the Storage Medium Molecule(s).

Control over the hole-storage and hole-hopping properties of the redox-active units of the storage molecules used in the memory devices of this invention allows fine control over the architecture of the memory device.

Such control is exercised through synthetic design. The hole-storage properties depend on the oxidation potential of the redox-active units or subunits that are themselves or that are used to assemble the storage media used in the devices of this invention. The hole-storage properties and redox potential can be tuned with precision by choice of base molecule(s), associated metals and peripheral substituents (Yang et al. (1999) *J. Porphyrins Phthalocyanines*, 3: 117–147).

For example, in the case of porphyrins, Mg porphyrins are more easily oxidized than Zn porphyrins, and electron withdrawing or electron releasing aryl groups can modulate the oxidation properties in predictable ways. Hole-hopping occurs among isoenergetic porphyrins in a nanostructure and is mediated via the covalent linker joining the porphyrins (Seth et al. (1994) *J. Am. Chem. Soc.*, 116: 10578–10592, Seth et al (1996) *J. Am. Chem. Soc.*, 118: 11194–11207, Strachan et al. (1997) *J. Am. Chem. Soc.*, 119: 11191–11201; Li et al (1997) *J. Mater. Chem.*, 7: 1245–1262, Strachan et al. (1998) *Inorg. Chem.*, 37: 1191–1201, Yang et al. (1999) *J. Am. Chem. Soc.*, 121: 4008–4018).

The design of compounds with predicted redox potentials is well known to those of ordinary skill in the art. In general, the oxidation potentials of redox-active units or subunits are well known to those of skill in the art and can be looked up (see, e.g., *Handbook of Electrochemistry of the Elements*). Moreover, in general, the effects of various substituents on the redox potentials of a molecule (e.g. a subunit) are generally additive. Thus, a theoretical oxidation potential can be readily predicted for any potential data storage molecule. The actual oxidation potential, particularly the oxidation potential of the information storage molecule(s) or the information storage medium can be measured according to standard methods. Typically the oxidation potential is predicted by comparison of the experimentally determined oxidation potential of a base molecule and that of a base molecule bearing one substituent in order to determine the shift in potential due to that particular substituent. The sum of such substituent-dependent potential shifts for the respective substituents then gives the predicted oxidation potential.

In addition, the oxidation potential shift produced by tightly coupling the molecules can be predicted by methods well known to those of skill in the art (see, e.g., Citation). The actual oxidation states can be empirically determined as described herein.

B) Synthesis of Storage Medium Molecules.

The basic synthetic methodologies used to construct the storage medium molecules of this invention are described in Prathapan et al. (1993) *J. Am. Chem. Soc.*, 115: 7519–7520, Wagner et al. (1995) *J. Org. Chem.*, 60: 5266–5273, Nishino et al. (1996) *J. Org. Chem.*, 61: 7534–7544, Wagner et al. (1996) *J. Am. Chem. Soc.*, 118: 11166–11180, Strachan et al. (1997) *J. Am. Chem. Soc.*, 119: 11191–11201, and Li et al. (1997) *J. Mater. Chem.*, 7: 1245–1262. These papers describe various strategies for the synthesis of a number of multiporphyrin (porphyrinic macrocycle) compounds. More particularly, these papers which focus on light capture, energy funneling, and optical gating, has led to the preparation of nanostructures containing up to 21 covalently linked porphyrins (Fenyo et al. (1997) *J. Porphyrins Phthalocyanines*, 1: 93–99, Mongin et al. (1998) *J. Org. Chem.* 63: 5568–5580, Burrell and Officer (1998) *Synlett* 1297–1307, Mak et al. (1998) *Angew. Chem. Int. Ed.* 37: 3020–3023, Nakano et al. (1998) *Angew. Chem. Int. Ed.* 37: 3023–3027, Mak et al. (1999) *Chem. Commun.* 1085–1086). Two-dimensional architectures, such as molecular squares (Wagner etal. (1998) *J. Org. Chem.*, 63: 5042–5049), T-shapes (Johnson, T. E. (1995), Ph.D. Thesis, Carnegie Mellon University), and starbursts (Li et al. (1997) *J. Mater. Chem.*, 7: 1245–1262.) all comprised of different covalently linked porphyrin constituents, have also been prepared.

The general synthetic strategy preferably involves the following approaches: (1) a synthesis of the subunit(s) comprising the polymeric storage molecules of this invention; (2) coupling of the subunits to form the polymeric storage molecules; and (3) the directed self-assembly of the resulting structures on electrode (e.g. gold electrode) surfaces. The synthesis of meso,meso coupled porphyrins is described in detail in Example 1.

The following synthetic methods form the foundation for the synthesis of porphyrin building blocks:

(1) A room temperature one-flask synthesis of meso-substituted porphyrins (Lindsey et al. (1987) *J. Org. Chem.* 52: 827–836, Lindsey et al. (1994) *J. Org. Chem.* 59: 579–587, Li et al. (1997) *Tetrahedron*, 53: 12339–12360.).

(2) Incorporation of bulky groups around the porphyrin to achieve enhanced solubility in organic solvents (Lindsey and Wagner (1989) *J. Org. Chem.*, 54: 828–836).

(3) A one-flask synthesis of dipyrromethanes, key building blocks in the synthesis of porphyrins bearing 2–4 different meso-substituents (Lee and Lindsey (1994) *Tetrahedron*, 50: 11427–11440, Littler et al. (1999) *J. Org. Chem.* 64: 1391–1396).

(4) A synthesis of trans-substituted porphyrins without acidolytic scrambling (Littler et al. (1999) *J. Org. Chem.* 64: 2864–2872).

(5) A rational synthesis of porphyrins bearing up to 4 different meso-substituents (Lee et al. (1995) *Tetrahedron*, 51: 11645–11672, Cho et al. (1999) *J. Org. Chem.* 64: 7890–7901).

(6) Mild methods for inserting magnesium (Lindsey and Woodford (1995) *Inorg. Chem.* 34: 1063–1069, O'Shea et al. (1996) *Inorg. Chem.*, 35: 7325–7338) or other metals (Buehler, J. W. In *The Porphyrins*; Dolphin, D. Ed.; Academic Press: New York. 1978; Vol.1, pp. 389–483) into porphyrins.

(7) A general approach for preparing thiol-derivatized porphyrin building blocks including various protecting groups for the thiol moiety (Gryko et al. (1999) *J. Org. Chem.* 64: 8634–8647).

The general methods for joining porphyrin monomers to form linked porphyrin arrays (e.g. meso-meso linked porphyrins) are described by Osuka and Shimidzu (1997) *Angew. Chem. Int. Ed. Engl.* 36: 135–137, Yoshida et al. (1998) *Chem. Lett.* 55–56, Nakano et al. (1998) *Angew. Chem. Int. Ed.* 37: 3023–3027, Ogawa et al. (1998) *Chem. Commun.* 337–338, Ogawa et al. (1999) *Angew. Chem. Int. Ed.* 38: 176–179, and Senge and Feng (1999) *Tetrahedron Lett.* 40: 4165–4168. Using the synthesis strategies exemplified here and in the Examples, one of ordinary skill in the art can routinely produce relatively complex data storage molecules for use in the devices of this invention.

C) Characterization of the Storage Media.

The storage media molecule(s), once prepared, can be characterized according to standard methods well known to those of skill in the art. The characterization of multiporphyrin nanostructures has been described (see, e.g., Strachan et al (1997) *J. Am. Chem. Soc.*, 119: 11191–11201; Wagner et al. (1996) *J. Am. Chem. Soc.*, 118: 3996–3997; Li et al. (1997) *J. Mater. Chem.*, 7: 1245–1262; Seth et al. (1996) *J. Am. Chem. Soc.*, 118: 11194–11207; Seth et al. (1994) *J. Am. Chem. Soc.*, 116: 10578–10592). In a preferred embodiment, the electrochemical studies include cyclic and square-wave voltammetry to establish the redox potentials of the monomeric and multi-unit constituents of the storage media. Bulk electrochemical oxidations are performed on each of the storage materials to assess the hole-storage capabilities and the stability. Absorption and vibrational spectroscopic methods are used to assess the structural and electronic properties of both the neutral and oxidized materials. Electron paramagnetic resonance techniques are used to probe the hole-storage and hole-mobility characteristics of the oxidized storage molecules. Using the above-identified techniques, benchmarks for the expected performance characteristics of a storage molecule (e.g., oxidation potentials, redox reversibility, dynamic hole-mobility characteristics, etc.) can be ascertained.

D) Self-assembly of the Storage Medium Molecules on Target Substrates.

In preferred embodiments, the storage molecules comprising the storage medium are designed to self-assemble on a substrate (e.g. a metal such as gold). The disk-like structure of the porphyrin macrocycles engenders self-assembly. Self-assembled monolayers of porphyrins on solid substrates are well known and have been extensively studied (see, e.g., Schick et al. (1989) *J. Am. Chem. Soc.*, 111: 1344–1350, Mohwald et al. (1986) *Thin Solid Films*, 141: 261–275). To exert control over the pattern of self-assembly, reactive sites (e.g. thiols) or linkers bearing active sites are incorporated into the storage molecules (nanostructures). The reactive sites bind to the target (e.g. gold electrode) surface giving an organized self-assembled structure. In the case of porphyrins with thiol linkers (e.g., thiol-derivatized linkers) attached to the meso-positions, the porphyrins arrange in upright orientations. Non-covalent interactions between storage molecules are typically weak, particularly when bulky aryl groups are attached to each of the porphyrins.

IV. Architecture of the Storage Device

One preferred embodiment of this invention is illustrated in FIG. 1. The basic memory device, a "storage cell" 100 comprises a working electrode 101 electrically coupled to a storage medium 102 comprising a multiplicity of storage molecules 105. The storage cell optionally includes an electrolyte 107 and a reference electrode 103. The storage medium has a multiplicity of different and distinguishable oxidation states, preferably a multiplicity of different and distinguishable non-neutral oxidation states, and can change oxidation (charge) state when a voltage or signal is applied thereby adding or removing one or more electrons. Each oxidation state represents a particular bit, however, where the oxidation states are not fully independently addressable, it may take as many as eight oxidation states to independently write three bits.

The storage medium remains in the set oxidation state until another voltage is applied to alter that oxidation state. The oxidation state of the storage medium can be readily determined using a wide variety of electronic (e.g. amperometric, coulometric, voltammetric) methods thereby providing rapid readout.

The storage medium comprises molecules having a single oxidation state and/or molecules having multiple different and distinguishable non-neutral oxidation states. Thus, for example, in one embodiment, the storage medium can comprise eight different species of storage molecules each having one non-neutral oxidation state and thereby store one byte. In another embodiment, the storage medium can comprise one species of molecule that has eight different and distinguishable oxidation states and store one byte in that manner as well. As explained herein, a large number of different molecules having different numbers of oxidation states can be used for the storage medium.

Because molecular dimensions are so small (on the order of angstroms) and individual molecules in the devices of this invention can store multiple bits, the storage devices of this invention therefore offer remarkably high storage densities (e.g. $>10^{15}$ bits/cm$^3$).

Moreover, unlike prior art, the devices of this invention are capable of a degree of self-assembly and hence easily fabricated. Because the devices are electrically (rather than optically) addressed, and because the devices utilize relatively simple and highly stable storage elements, they are readily fabricated utilizing existing technologies and easily incorporated into electronic devices. Thus, the molecular memory devices of this invention have a number of highly desirable features:

Because the storage medium of the devices described herein is electrically-addressed, the devices are amenable to the construction of a multilayered chip architecture. An architecture compatible with such a three-dimensional structure is essential to achieve the objective of $10^{15}$ bits/cm$^3$. In addition, because writing and reading is accomplished electrically, many of the fundamental problems inherent with photonics are avoided. Moreover, electrical reading and writing is compatible with existing computer technology for memory storage.

In addition, the devices of this invention achieve a high level of defect tolerance. Defect tolerance is accomplished through the use of clusters of molecules (up to several million in a memory cell). Thus, the failure of one or a few molecules will not alter the ability to read or write to a given memory cell that constitutes a particular bit of memory. In preferred embodiments, the basis for memory storage relies on the oxidation state(s) of porphyrins or other porphyrinic macrocycles of defined energy levels. Porphyrins and porphyrinic macrocycles are well known to form stable radical cations. Indeed, the oxidation and reduction of porphyrins provide the foundation for the biological processes of photosynthesis and respiration. Porphyrin radical cations can be formed chemically on the benchtop exposed to air. We know of no other class of molecules with such robust electroactive properties.

Preferred storage molecules of this invention molecule (e.g., SHMU or DHMU) can hold multiple holes, corresponding to multiple bits, although in certain embodiments, there may not be a one-to-one correspondence between the number of holes and bits stored. In contrast, the dyes (photochromic, electrochromic, redox) and molecular machines are invariably bistable elements. Bistable elements exist either in a high/low state and hence can only store a single bit. The SHMU and DHMU are unique molecular nanostructures providing resilient storage of multiple bits.

Reading can be accomplished non-destructively or destructively as required in different chip applications. The speed of reading is conservatively estimated to lie in the MHz to GHz regime. Memory storage is inherently latchable due to the stability of the porphyrin or other porphyrinic macrocycle radical cations. It is noted in this context that latchable memory need not permanently reside in a particular state, but rather that the memory reside in a particular state for a period of time longer that a refresh cycle. In the instant case, porphyrin monomers of this invention show persistence times on the order of tens of minutes; far longer than a typical refresh cycle. Oxidation of the porphyrins or other porphyrinic macrocycles can be achieved at relatively low potential (and at predesignated potentials through synthetic design), enabling memory storage to be achieved at very low power. Porphyrins and porphyrin radical cations are stable across a broad range of temperatures, enabling chip applications at low temperature, room temperature, or at elevated temperatures.

Fabrication of the devices of this invention relies on known technology. The synthesis of the storage media takes advantage of established building block approaches in porphyrin and other porphyrinic macrocycle chemistry. Synthetic routes have been developed to make the porphyrin and porphyrinic macrocycle building blocks, to join them in covalent nanostructures, and to purify them to a high level (>99%).

In preferred embodiments, the storage medium nanostructures are designed for directed self-assembly on gold surfaces. Such self-assembly processes are robust, result in the culling out of defective molecules, and yield long-range order in the surface-assembled cluster.

Porphyrin-thiols have been assembled on electroactive surfaces. The arrays that define the addressable bits of memory can be achieved through conventional microfabrication techniques. The storage molecules are self-assembled onto these electrode arrays and attached to the gold surface using conventional dipping methods.

Figure 2:
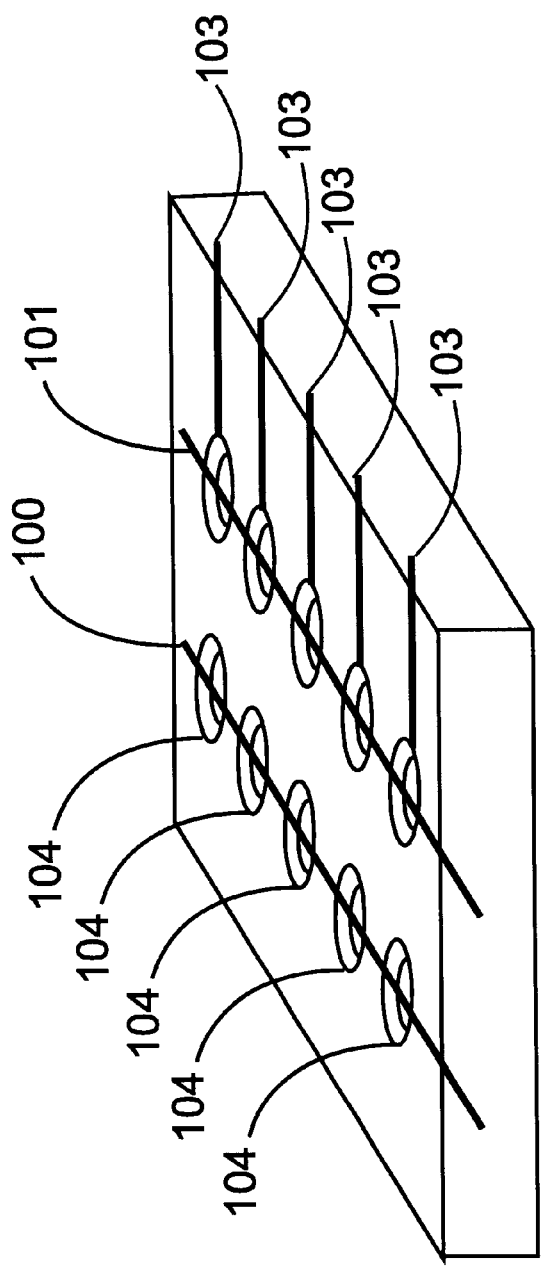
FIG. 2 illustrates the disposition of the storage cell(s) of this invention on a chip.

The basic storage cell (electrode(s) and storage medium) of this invention can be incorporated into a functional device in a wide variety of configurations. One chip-based embodiment of this invention is illustrated in FIG. 2. As illustrated in FIG. 2 the storage medium 102 is disposed in a number of storage locations 104. Each storage location is addressed by a working electrode 101 and a reference electrode 103 so that the storage medium 102 combined with the electrodes forms a storage cell 100 at each storage location.

Figure 3:
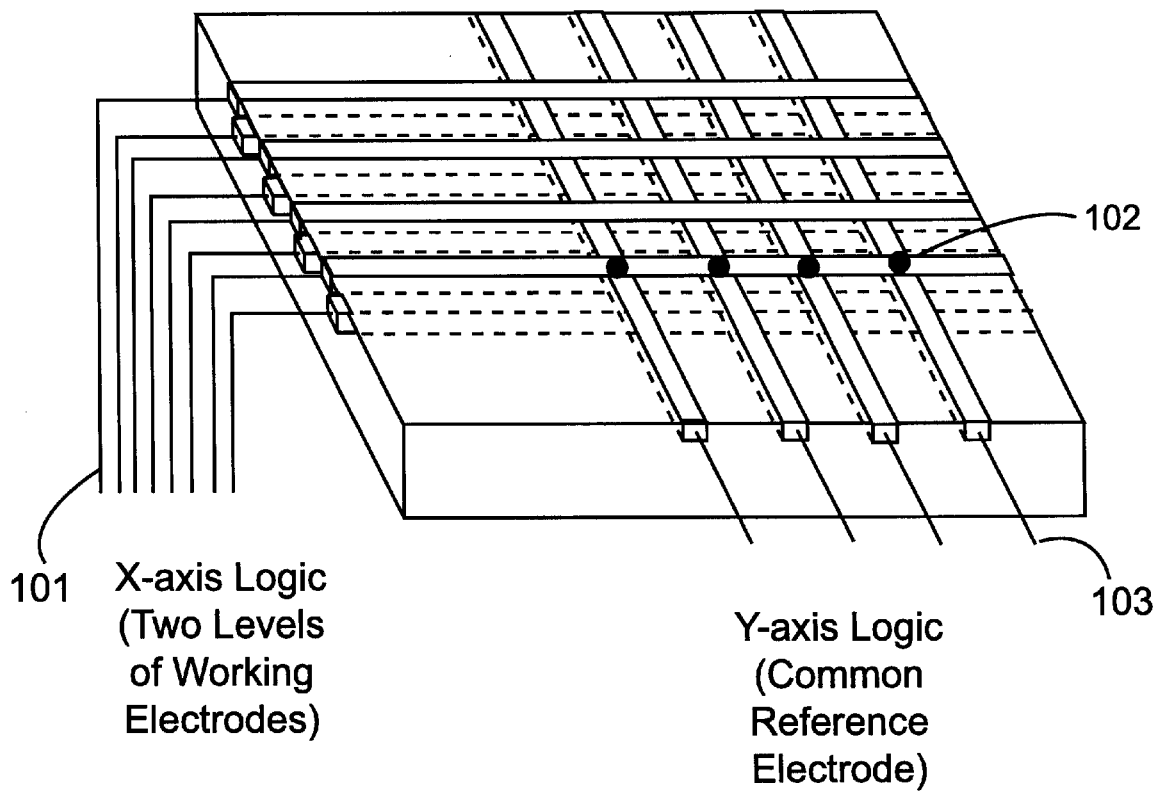
FIG. 3 illustrates a preferred chip-based embodiment of this invention. A two-level chip is illustrated showing working electrodes 101, orthogonal reference electrodes 103, and storage elements 104.

One particularly preferred chip-based embodiment is illustrated in FIG. 3. In the illustrated embodiment, a plurality of working electrodes 101 and reference electrodes 103 are illustrated each addressing storage media 102 localized at discrete storage locations thereby forming a plurality of storage cells 100. Multiple storage cells can be associated with a single addressing electrode as long as oxidation states of the storage cells are distinguishable from each other. It should be noted that this forms a functional definition of a storage cell. Where two discrete areas of storage medium are addressed by the same electrode(s) if the storage media comprise the same species of storage molecule the two discrete areas will functionally perform as a single storage cell, i.e. the oxidation states of both locations will be commonly set, and/or read, and/or reset. The added storage location, however, will increase the fault tolerance of the storage cell as the functional storage cell will contain more storage molecules. In another embodiment, each individual storage cell is associated with a single addressing electrode.

In preferred embodiments, the storage cells of a memory device are all electrically coupled to one or more reference electrodes. The reference electrode(s) can be provided as discrete electrodes or as a common backplane.

The chip illustrated in FIG. 3 has two levels of working electrodes and hence two levels of storage cells 100 (with numerous storage cells on each level). Of course, the chip can be fabricated with a single level of electrodes and memory element or literally hundreds or thousands of different levels of storage cell(s), the thickness of the chip being limited essentially by practical packaging and reliability constraints.

In particularly preferred embodiments, a layer of dielectric material optionally imbedded with counterions to ensure electrical connectivity between the working and reference electrode(s) and stability of the cationic species in the absence of applied potential (latching) is disposed in the storage cell. In some embodiments, the dielectric material can be incorporated into the storage medium itself.

While, in some preferred embodiments, feature sizes are rather large (e.g. memory elements approximately 10×10× 10 $\mu$m and electrode thickness ~200 nm), feature size can be reduced at will so that feature sizes are comparable to those in conventional silicon-based devices (e.g., 50 nm–100 nm on each axis).

Figure 4:
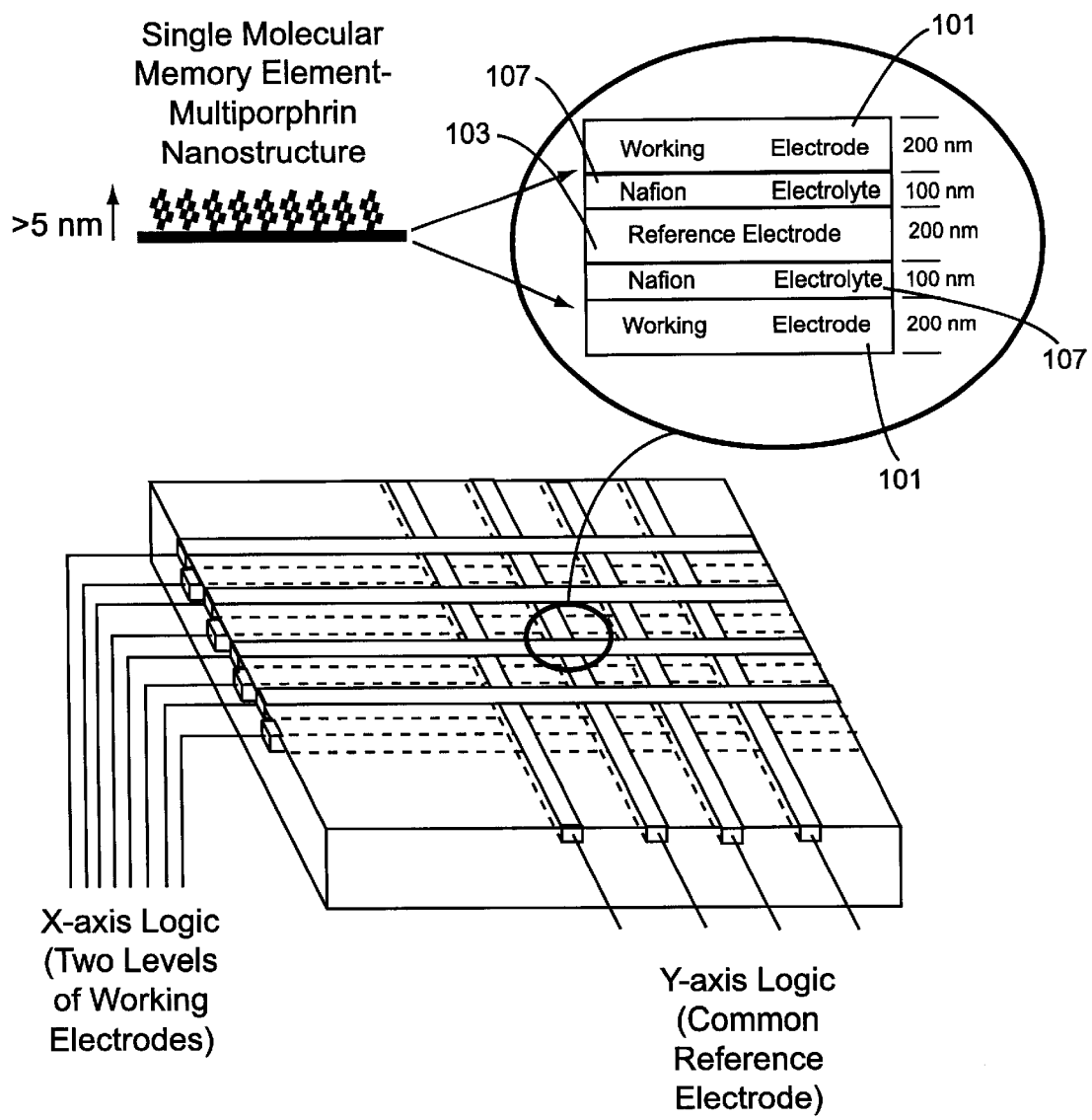
FIG. 4. The three-dimensional architecture of a single memory storage cell (memory element) on the chip.
Figure 5:
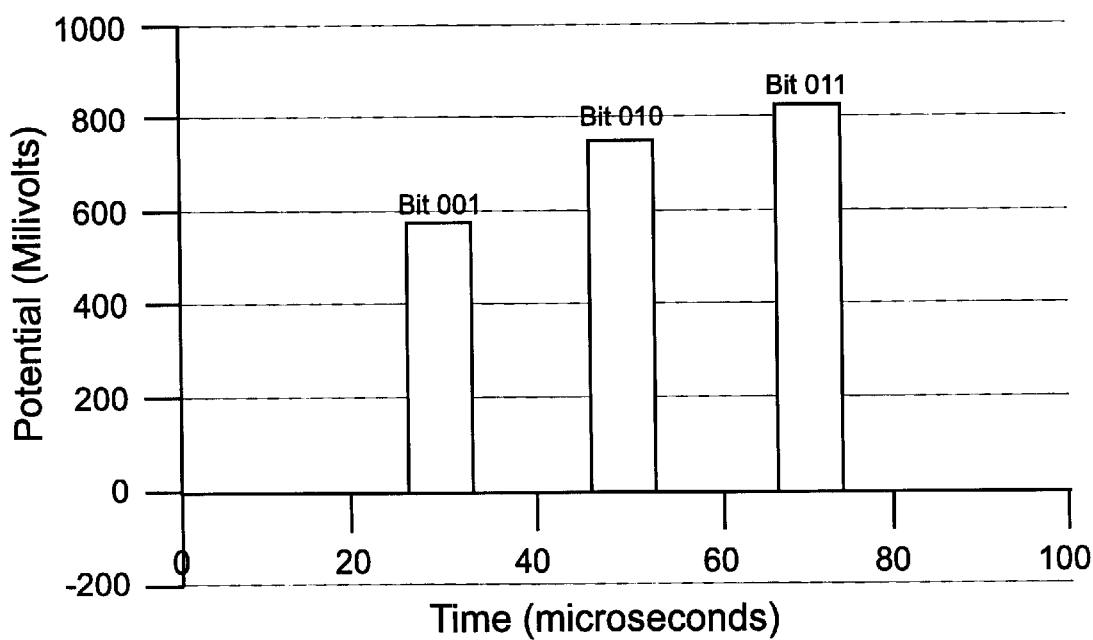
FIG. 5 illustrates writing to a molecular memory of this invention. In preferred embodiments, this is accomplished through the application of very short (e.g., microsecond) pulses applied at a voltage sufficient to oxidize a storage medium (e.g., a porphyrin) to the appropriate redox state as summarized in this figure. Thus, each redox state of the composite multiunit nanostructure (e.g. porphyrinic array) can be independently accessed to provide one bit of resolution. This can be accomplished via the electrochemical oxidation of the molecule in stepwise increments.

In a preferred embodiment, the storage device includes: (1) A gold working electrode (e.g., 200 nm thick), deposited on a nonconducting base, and line-etched to achieve electrode widths of 10's to 100's of nm. (2) A monolayer of self-assembled porphyrinic nanostructures (storage molecules 105) attached to the gold surface via the sulfur atom of the thiophenol group. (3) A 100-nm thick layer of dielectric material 107 embedded with counterions to ensure electrical connectivity to the reference electrode and stability of the cationic species in the absence of applied potential (latching). (4) A 200-nm thick nonpolarizable reference electrode 103 line etched in the same fashion as those of the working electrode 101, but assembled with lines orthogonal to the latter electrode. (5) A mirror image construct that utilizes the same reference electrode. Thus, in one embodiment, the three-dimensional architecture of a single memory storage location (memory element) on the chip will look as indicated in FIG. 4.

While the discussion herein of electrodes is with respect to gold electrodes, it will be recognized that numerous other materials will be suitable. Thus, electrode materials include, but are not limited to gold, silver, copper, other metals, metal alloys, organic conductors (e.g. doped polyacetylene, doped polythiophene, etc.), nanostructures, crystals, etc.

Similarly, the substrates used in the fabrication of devices of this invention include, but are not limited to glasses, silicon, minerals (e.g. quartz), plastics, ceramics, membranes, gels, aerogels, and the like.

V. Fabrication and Characterization of the Storage Device

A) Fabrication.

The memory devices of this invention can be fabricated using standard methods well known to those of skill in the art. In a preferred embodiment, the electrode layer(s) are applied to a suitable substrate (e.g. silica, glass, plastic, ceramic, etc.) according to standard well known methods (see, e.g., Choudhury (1997) *The Handbook of Microlithography, Micromachining, and Microfabrication,* Soc. Photo-Optical Instru. Engineer, Bard & Faulkner (1997) *Fundamentals of Microfabrication*). In addition, examples of the use of micromachining techniques on silicon or borosilicate glass chips can be found in U.S. Pat. Nos. 5,194,133, 5,132,012, 4,908,112, and 4,891,120.

In one preferred embodiment a metal layer is beam sputtered onto the substrate (e.g,. a 10 nm thick chromium adhesion layer is sputtered down followed by a 200 nm thick layer of gold). Then maskless laser ablation lithography (see below), performed (e.g., with a Nd:YAG laser, is used to create features with micron dimensions, or with an excimer laser to create features of nanometer dimensions) will create an array of parallel lines of conductor (e.g., gold), used as the working electrodes with dimensions ranging between a few microns to tens of nanometers;

Once the electrode array is formed, the entire array, or portions of the array, or individual electrodes are wetted (e.g. immersed or spotted) with one or more solutions of the appropriate derivatized storage media (e.g. thiol-substituted porphyrin nanostructures), and the constituents of the memory medium (e.g., porphyrin subunits) self-assemble on the micro-sized gold arrays to form the memory elements. It will be appreciated that different solutions can be applied to different regions of the electrode array to produce storage cells comprising different storage medium. Methods of spotting different reagents on surfaces (e.g. on glass surfaces) at densities up to tens of thousands of different species/spots per $cm^2$ are known (see, e.g., U.S. Pat. No: 5,807,522).

Then a suitable electrolyte layer (e.g. a thin layer of Nafion™ polymer) approximately 1 nm to 1000 nm, preferably about 100 nm to about 500 nm, more preferably about 10 nm to about 100 nm and most preferably about one hundred nanometers thick) will be cast over the entire surface of the chip. This polymer serves to hold the electrolyte for electrochemical reaction. Finally, the entire chip is coated with a layer (e.g., 10 nm to about 1000 nm, more preferably 100 nm to about 300 nm and most preferably about 200 nm) of conducting material (e.g. silver) which acts as a reference electrode 103.

The chip is then turned 90 degrees, and maskless laser ablation lithography will be performed again to create a second array of parallel lines that are perpendicular to the original set. This forms a three dimensional array of individual memory elements, where each element is formed by the intersection of these two perpendicular linear arrays (see FIG. 4).

Each individual element can be addressed by selecting the appropriate X and Y logic elements, corresponding to one gold working electrode and one reference electrode separated by the Nafion polymer/electrolyte layer. Since this structure is inherently three dimensional, it should be possible to extend the array into the Z-direction, creating a 3-D array of memory elements as large as it is feasible to connect to.

These structures are initially created on the micron scale. It is possible to decrease the size of these structures to sub-micron dimensions. It is possible to create these structures on a scale similar to silicon microstructures created with conventional nanolithographic techniques (i.e. 100–200 nm). This would allow the interfacing of the memory elements with conventional silicon-based semiconductor electronics.

In the laser-ablation lithography discussed above, coherent light is sent through a beam splitter (50% transmittance) and reflected by a mirror to make two nearly parallel identical beams (Rosenwald et al. (1998) *Anal. Chem.,* 70: 1133–1140). These beams are sent through e.g., a 50 cm focal length lens for ease in focusing to a common point. The placement of the beams is fine-tuned to allow complete overlap of the mode structure of the laser spot. Higher order interference patterns are minimized through the use of high quality optics ($\frac{1}{10}$ wave surface flatness). This ensures that the variation between intensity maxima and minima in the first order will be several orders of magnitude larger than those formed with second and higher orders. This produces a well-defined pattern of lines across the electrode surface, where the spacing between points of positive interference (D) can be approximated by the Bragg Equation: $n\lambda=2D\sin(\theta/2)$, where $\lambda$=wavelength, $\theta$=angle between the beams, and n is order. For example, when a Nd:YAG is used at 1064 nm, the recombination of the two beams in this manner generates an interference pattern with ~2 micron spacing when the angle between the 2 beams is 15°. The interference pattern spacing can easily be changed by modifying the angle between the beams. Attenuation of the beam was accomplished by inserting one or more neutral density filters before the beam splitter. In this way, the exposure of the gold layer to the Nd-YAG interference pattern can be performed at different beam attenuations to produce power densities between 1 and 100 $MW/cm^2$.

B) Electrically Coupling Storage Medium to Electrode.

In the storage devices of this invention, the storage medium is electrically coupled to one or more electrodes. The term "electrical coupling" is used to refer to coupling schemes that permit the storage medium to gain or lose electrons to the electrode. The coupling can be a direct attachment of the storage medium to the electrode, or an indirect attachment (e.g. via a linker). The attachment can be a covalent linkage, an ionic linkage, a linkage driven by hydrogen bonding or can involve no actual chemical attachment, but simply a juxtaposition of the electrode to the storage medium. In some embodiments, the electrode can be some distance (e.g, about 5 Å to about 50 Å) from the storage medium and electrical coupling can be via electron tunneling.

In some preferred embodiments, a "linker" is used to attach the molecule(s) of the storage medium to the electrode. The linker can be electrically conductive or it can be short enough that electrons can pass directly or indirectly between the electrode and a molecule of the storage medium.

The manner of linking a wide variety of compounds to various surfaces is well known and is amply illustrated in the literature. Means of coupling the molecules comprising the storage medium will be recognized by those of skill in the art. The linkage of the storage medium to a surface can be covalent, or by ionic or other non-covalent interactions. The surface and/or the molecule(s) may be specifically derivatized to provide convenient linking groups (e.g. sulfur, hydroxyl, amino, etc.).

The linker can be provided as a component of the storage medium molecule(s) or separately. Linkers, when not joined to the molecules to be linked are often either hetero- or homo-bifunctional molecules that contain two or more reactive sites that may each form a covalent bond with the respective binding partner (i.e. surface or storage medium molecule). When provided as a component of a storage molecule, or attached to a substrate surface, the linkers are preferably spacers having one or more reactive sites suitable for bonding to the respective surface or molecule.

Linkers suitable for joining molecules are well known to those of skill in the art and include, but are not limited to any of a variety of, a straight or branched chain carbon linker, or a heterocyclic linker, amino acid or peptide linkers, and the like. Particularly preferred linkers include, but are not limited to 4,4'-diphenylethyne, 4,4'-diphenylbutadiyne, 4,4'-biphenyl, 1,4-phenylene, 4,4'-stilbene, 1,4-bicyclooctane, 4,4'-azobenzene, 4,4'-benzylideneaniline, and 4,4"-terphenyl. Linkers include molecules that join one or more molecules of the storage medium to the electrode(s).

C) Addressing the Memory Cells.

Addressing of the storage cell(s) in the devices of this invention is relatively straightforward. In a simple approach a discrete pair of electrodes (one working and one reference electrode) can be connected to every storage cell. Individual reference electrodes, however are not required and can be replaced with one or more common reference electrodes connected to all or to a subset of all of the storage elements in a particular device. Alternatively, the common reference electrodes can be replaced with one or more conductive "backplanes" each communicating to all, or to a subset, of the storage cells in a particular device.

Where the storage cells contain identical storage media, each storage cell is preferably addressed with a separate working electrode so that the storage (oxidation) states of the storage cells can be distinguished from each other. Where the storage cells contain different storage media such that the oxidation states of one storage cell are different and distinguishable from the oxidation states of another storage cell, the storage cells are preferably addressed by a common working electrode thereby reducing the number of electrodes in a device.

In one preferred embodiment, the storage devices of this invention contain (64, 128, 256, 512, 1024 or more storage locations per layer (64, 128, 256, 512, 1024 or more locations in the mirror image architecture) with each location capable of holding a multiple-bit SHMU or DHMU word. Accordingly, a preferred 1024-bit SHMU or a preferred 512-bit DHMU chip will contain 8 wiring interconnects on each of the three electrode grids in the 3-dimensional architecture illustrated in FIG. 4.

D) Characterization of the Memory Device.

The performance (e.g. operating characteristics) of the memory devices of this invention is characterized by any of a wide variety of methods, most preferably by electrochemical methods (amperometry, sinusoidal voltammetry and impedance spectroscopy, see, e.g., Howell et al. (1986) *Electroanal. Chem.*, 209: 77–90; Singhal et al. (1997) *Anal. Chem.*, 69: 1662–1668; Schick et al. (1989) *Am. Chem. Soc.* 111: 1344–1350), atomic force microscopy, electron microscopy and imaging spectroscopic methods. Surface-enhanced resonance and Raman spectroscopy are also used to examine the storage medium on the electrodes.

Among other parameters, characterization of the memory devices (e.g., memory cells) involves determining the number of storage medium molecules (e.g., porphyrin arrays) required for defect-tolerant operation. Defect tolerance includes factors such as reliably depositing the required number of holes to write the desired digit and accurately detecting the numbers/hopping rates of the holes.

The long-term resistance of electron holes to charge-recombination in the solid-phase medium of the device package is also determined. Using these parameters, the device architecture can be optimized for commercial fabrication.

VI. Writing to the Storage Device

In preferred embodiments of the data storage devices of this invention, information is written to a particular memory location via application of a potential of the requisite value and temporal duration at the appropriate working and reference electrode(s) to achieve the desired digital value. The information can be erased via application of a potential of the opposite sign.

The writing process is illustrated with respect to storage of data in porphyrin dimer I (Formula I). While each porphyrin subunit individually has a single non-neutral oxidation state, as shown in Table 2, the dimmer has four non-zero oxidation states.

TABLE 2

Mapping of bits onto oxidation potential in the porphyrin dimmer of Formula I.

| Bit | Oxidation potential (V) | Redox-active unit |
| --- | --- | --- |
| parity | 0 | dimer neutral |
| 00 | 0.49 | dimer oxidation potential 1 |
| 01 | 0.66 | dimer oxidation potential 2 |
| 10 | 0.95 | dimer oxidation potential 3 |
| 00 | 1.03 | dimer oxidation potential 4 | processes, each of which is separated by at least about 50 mV. To activate bit 001, a potential greater than 0.49 V (but less than 0.66 V) would be applied to the memory element to oxidize porphyrin 1 to its first oxidation state. A voltage greater than 0.66 V and less than 0.95 V would oxidize porphyrin 1 to its second oxidation state. A voltage greater than 0.95 V and less than 1.03 V would oxidize porphyrin 2 of the dimer to its first oxidation state and a voltage greater than 1.03 would oxidize porphyrin 2 of the dimer to its second oxidation state.

There is a great advantage to the small size of each memory element, which is essentially a modified electrode surface. When each memory element is reduced to submicron dimensions, the area of the surface allows the presence of only a few hundred data storage (e.g., porphyrin) molecules. Using Faraday's law, Q=nFN (where Q equals the total charge, n equals the number of electrons per molecule, F is 96,485 Coulombs/mole and N is the number of moles of electroactive species present), it can be determined that only a small charge ($1.6 \times 10^{-16}$ C; if passed in 1 $\mu$s, would result in a current of roughly 160 pA) must pass in order to change the electrochemical charge corresponding to each bit.

Additionally, the intrinsic limitation to the speed of most electrochemical experiments lies in the time required to charge the electrode to the appropriate potential (the charging current, which has a time dependence of $\exp(-t/RC)$). Since the capacitance of the electrode is directly proportional to its area, miniaturization of each element of the system to submicron dimensions will greatly increase its speed. For example, a square gold electrode with 0.1 $\mu$m dimensions would have a capacitance of approximately $2 \times 10^{-19}$ F, leading to an RC time constant of only 2 picoseconds. For this reason, electrode charging currents should be insignificant in determining the ultimate performance of these devices.

The voltage used to write the data can be derived from any of a wide variety of sources. In a simple embodiment, the voltage can simply be the output from a power supply. However, in preferred embodiments, the voltage will be the output from some element of an electronic circuit. The voltage can be a signal, the representation of a logic state, the output from a gate, from an optical transducer, from a central processing unit, and the like. In short, virtually any voltage source that can be electrically coupled to the devices of this invention can be used to write data to the storage media therein.

VII. Reading from the Storage Device

The storage device(s) of this invention can be read according to any of a wide variety of methods well known to those of ordinary skill in the art. Essentially any method of detecting the oxidation state of a compound can be utilized in the methods of this invention. However, where the readout is destructive of the state of the memory cell(s) (e.g. in certain SHSU or SHMU memories), the read will preferably be followed by a refresh to reset the oxidation state of the storage cell.

In particularly preferred embodiments, the storage medium 102 of a storage cell 100 is set to neutral (e.g., 0 potential for the system, but which might not be at true zero voltage with respect to ground) using the working electrode. The oxidation state of the memory cell is then set by changing the potential at the reference electrode 103 (e.g. by setting the reference electrode negative to the desired voltage). The oxidation state of the storage cell is then measured (e.g. using sinusoidal voltammetry) via the working electrode 101. In this preferred format, the oxidation state is assayed by measuring current. By measuring current at the working electrode 101 and setting the state with the reference electrode 103, the measurement is not made at the place the potential is applied. This makes it far simpler to discriminate the oxidation state. If the potential were applied to the electrode through which the current was measured unnecessary noise would be introduced into the system.

A) Reading from the Storage Molecule(s).

Reading of information from a particular memory location is achieved extremely rapidly by sweeping a potential over the full range used to establish the dynamic range of the storage element. The fidelity of the measurement is dependent on how well the oxidation state of the individual storage element can be determined. Traditionally, electrochemical methods could only improve the signal to noise ratio by discriminating the faradaic signal from the background components in the time domain through application of pulse waveforms (i.e., differential pulse polarography, square wave voltammetry). These methods discriminate the faradaic current from the charging current in the time domain, since charging currents decay much more rapidly than the faradaic current ($\exp(-t/RC)$ vs $t^{-\frac{1}{2}}$, respectively). However, the analytical faradaic current is not totally discriminated from the charging current, and most of the signal is discarded because sampling is done late in the pulse cycle.

Figure 6:
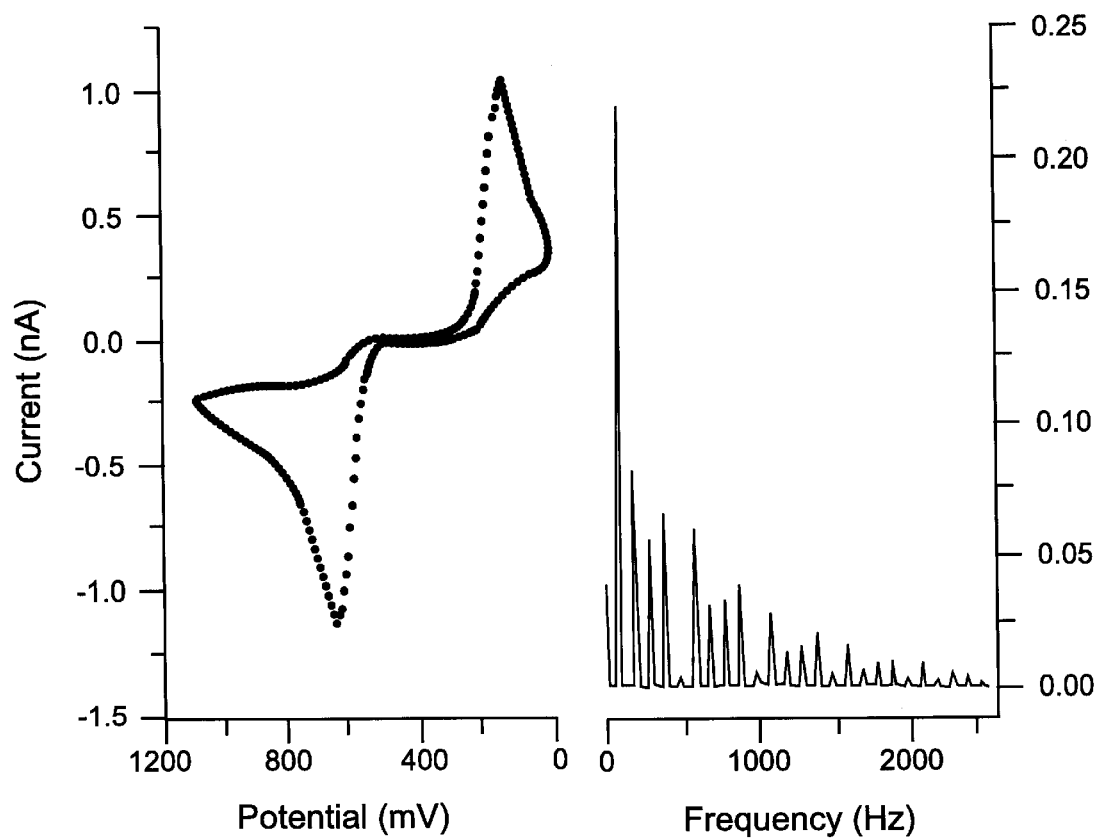
FIG. 6 illustrates a frequency domain spectrum of the faradaic SV response. Note that the numerous harmonic frequency components depend on many of the same voltammetric parameters (e.g., $E^°$, $E_{switch}$, scan rate, number of electrons, etc.) that govern the response observed in cyclic voltammetry, and can be easily isolated in the frequency domain.

More recently, sinusoidal voltammetry (SV) has been shown to have significant advantages over traditional waveforms in an electrochemical experiment (Singhal et al. (1997) *Anal. Chem.*, 69: 1662–1668. For example, the background current resulting from cyclic voltammetry (consisting primarily of charging current) resembles a square wave, which contains significant intensity at both fundamental and odd harmonic frequencies. In contrast, the charging current resulting from sine wave excitation has only one frequency component centered at the fundamental, while the faradaic current is distributed over many frequencies as is illustrated in FIG. 6. This characteristic of sine wave excitation simplifies the electroanalytical measurement, since the signal from each oxidation state can be fine-tuned by "locking-in" on one of the higher frequency harmonics. Ultimately, the speed at which this can be performed is only limited by the kinetics of the redox reaction, which may ultimately lead to megahertz frequency operation.

Since most electrochemical methods rely on differences between the $E_{1/2}$'s ($E_{1/2}$ is the potential at which half of the subject molecules are oxidized or reduced to a particular oxidation state) to differentiate compounds present in a sample and thereby to generate the selectivity for the measurement, this has severely limited the utility of electrochemical methods for the analysis of many complex matrices. In contrast, sinusoidal voltammetry can exploit the vast diversity in electron transfer rates observable at solid electrodes ($k^0$, the rate of electron transfer) can vary over ten orders of magnitude at the same electrode surface) to obtain additional selectivity in the electrochemical measurement.

The composition of the frequency spectrum is extremely dependent on the rate of electron transfer. By adjusting the frequency of the sinusoidal (or other time-varying) excitation waveform, it becomes possible to use this kinetic information as well as the phase information to discriminate between two molecules which have very similar electrochemical properties. For example, this technique has been used for the detection of the direct oxidation of double-stranded DNA at copper electrodes (Singhal and Kuhr (1997) *Anal. Chem.*, 69: 1662–1668). Where this is usually undetectable at conventional electrodes with standard voltammetric techniques, the use of sinusoidal voltammetry allowed the measurement of 1.0 nM double-stranded DNA. The concentration detection limit (S/N=3) for this size of dsDNA at the 6th harmonic is 3.2 pM. When coupled with a low-volume system, such as a monolayer of the adsorbed material, this allows detection of sub-zeptomole ($10^{-21}$ mole) quantities of the storage medium molecule(s) on the surface.

This procedure may ultimately degrade the memory in the absence of a refresh mechanism. The level of degradation will depend on the total number of molecules ultimately used to ensure acceptable fault tolerance. To avoid degradation problems, however, a refresh cycle (a write cycle resetting the memory to the read value) can be inserted immediately after each read cycle is complete.

B) Instrumentation for Reading/writing Molecular Memories.

As indicated above, the molecular memory devices can be read by any of a wide variety of electrochemical technologies including amperometric methods (e.g. chronoamperometry), coulometric methods (e.g. chronocoulometry), voltammetric methods (e.g., linear sweep voltammetry, cyclic voltammetry, pulse voltammetries, sinusoidal voltammetry, etc.), any of a variety of impedance and/or capacitance measurements, and the like. Such readouts can be performed in the time and/or frequency domain.

1) Fast potentiostat/voltammetry System.

In one preferred embodiment, readout is accomplished using a fast potentiostat/voltammetry system. Such a system is capable of reading and writing the memory elements, on a microsecond time scale. Such a system can be modified from a prototypical system described in U.S. Pat. No. 5,650,061.

Figure 7:
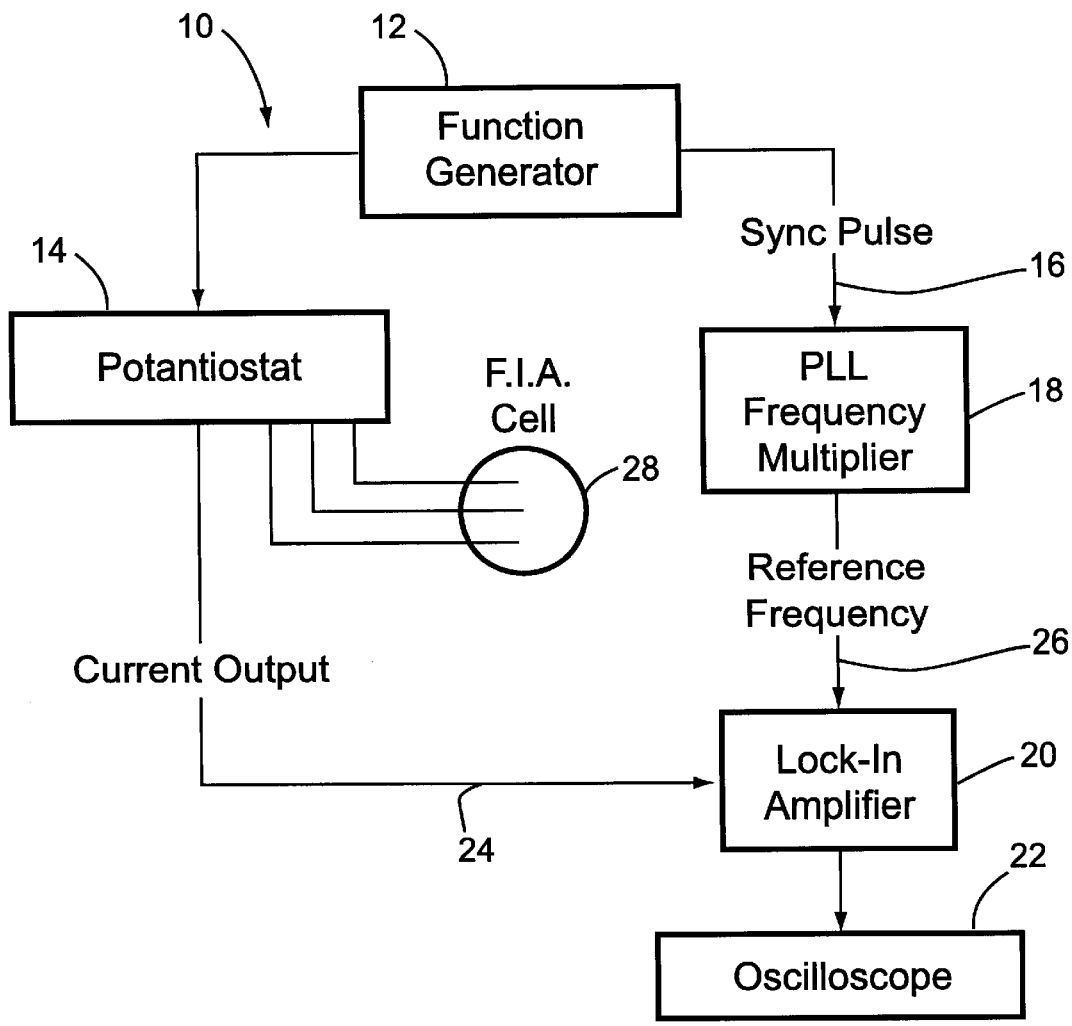
FIG. 7 illustrates a sinusoidal voltammetry system suitable for readout of the memory devices of this invention.

As illustrated in FIG. 7, a potentiostat with an RC time constant less than one microsecond is provided by using a fast voltage driver (e.g., video buffer amplifier). A preferred video buffer amplifier retains a usable bandwidth beyond 20 MHz and is used to rephase the voltage and current in the excitation signal to zero phase shift between voltage and current. This rephasing of the excitation signal immediately before the working electrode cancels out any phase shift which might be introduced by capacitance in the cable leading from the Arbitrary Waveform Synthesizer (AWS) function generator. An important part of the current monitor is a wide band op-amp. By using an op-amp with a very wide gain-bandwidth product, the amplifier gain can be set to 10,000 and still retain a bandwidth usable from DC to above 1 MHz. This allows the collection of impedance data from electrodes as small as a 1 $\mu$m disk over a frequency range from 15 kHz to 5 MHz.

2) A Megahertz Impedance Analysis System.

An ultrafast impedance analysis system capable of characterizing the SHMU storage medium on a microsecond time scale can be constructed using an Arbitrary Waveform Synthesizer (e.g., HP 8770A, AWS) and a 1-GHz Digitizing Oscilloscope (e.g., HP 54111D) controlled by a computer system (e.g. HP 9000 series 300 computer system, Hewlett-Packard, Palo Alto, Calif.). The impedance data sets can be collected with the digital scope with 8192 time domain points at 25 MHz. Thus, a full 8192 point data set can be acquired in a total of 328 $\mu$s. Both the excitation and the response waveforms are measured; the excitation waveform is measured prior to the start of the experiment so that the response acquisitions can be done during the course of the experiment without interruption. One preferred excitation signal consists of a waveform with an amplitude of 60 $mV_{(p-p)}$ which covers a frequency band from approximately 30 KHz to over 1 MHz. If five complete replicates of each excitation or response waveform are contained within the 8192 data points set captured by the capture device (e.g. oscilloscope), because no further ensemble averaging is needed, each full impedance spectra can be acquired in 328 $\mu$s. Therefore, the whole frequency band under study can be excited and monitored in a single acquisition. The FFT of the time domain data provides frequency-amplitude and frequency-phase characterization of the data equivalent to the data given by a lock-in based system.

VIII. Uses of the Storage Device

One of ordinary skill in the art will appreciate that the memory devices of this invention have wide applicability in specialized and general-purpose computer systems. Of course commercial realization of the device(s) will be facilitated by the adoption of computer architecture standards compatible with this technology. In addition, commercial adoption of this technology will be facilitated by the use of other molecular electronic components that will serve as on-chip buffers and decoders (that is, molecular logic gates), and the like. In addition, commercialization will be facilitated by the development of a full manufacturing infrastructure.

Regardless, prior to the development of a fully integrated design and manufacturing platform for molecular electronic information storage and transfer, even early generation prototype molecular memory devices described herein have utility in specialized military storage applications. For example, a prototype 1024/512-bit molecular memory device has sufficient capacity to hold a substantial base of personal and/or other proprietary information (e.g. in a "smart-card"). The memory device is easily erased simply by applying a low potential reverse bias current across all memory cells and can be re-written on demand.

The memory devices of this invention have sufficient capacity to hold personal identification, and/or medical, and/or financial information. Even a memory device that degrades upon multiple read cycles is extremely useful if the number of read cycles is highly limited (perhaps only one, for example, providing one time access to funds and/or medical information). A memory device that degrades upon multiple read cycles or simply with time is also useful in applications where long-term data persistence is not needed or is strategically unwise. Thus, numerous important applications for early generation memory devices present themselves. Successes of the memory devices in these applications will foster even more rapid full-scale commercialization of the technology.

Figure 8:
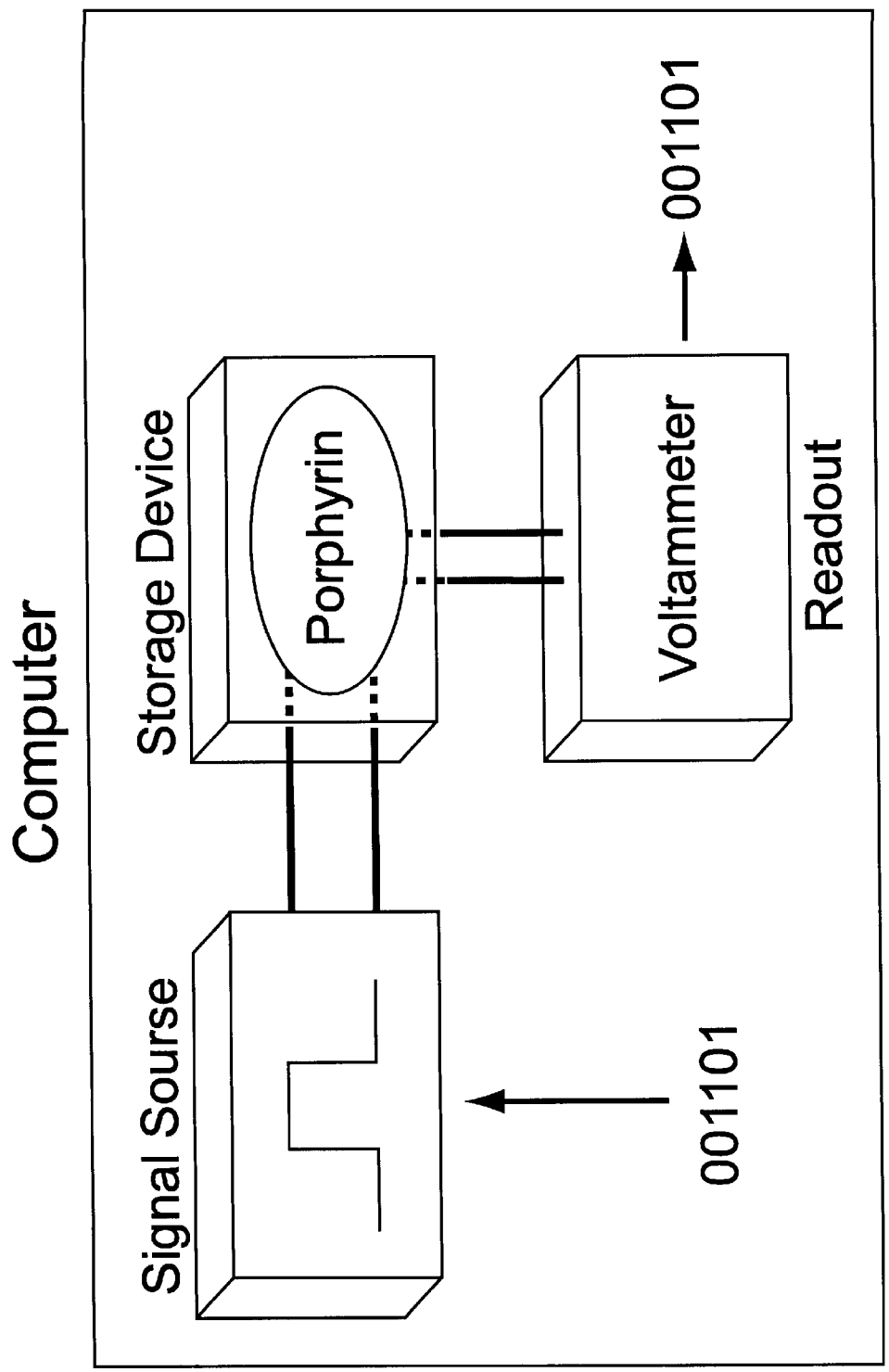
FIG. 8 illustrates a computer system embodying the memory devices described herein. Typically the memory device will be fabricated as a sealed "chip". Ancillary circuitry on the chip and/or in the computer permits writing bits into the memory and retrieving the written information as desired.
Figure 9:
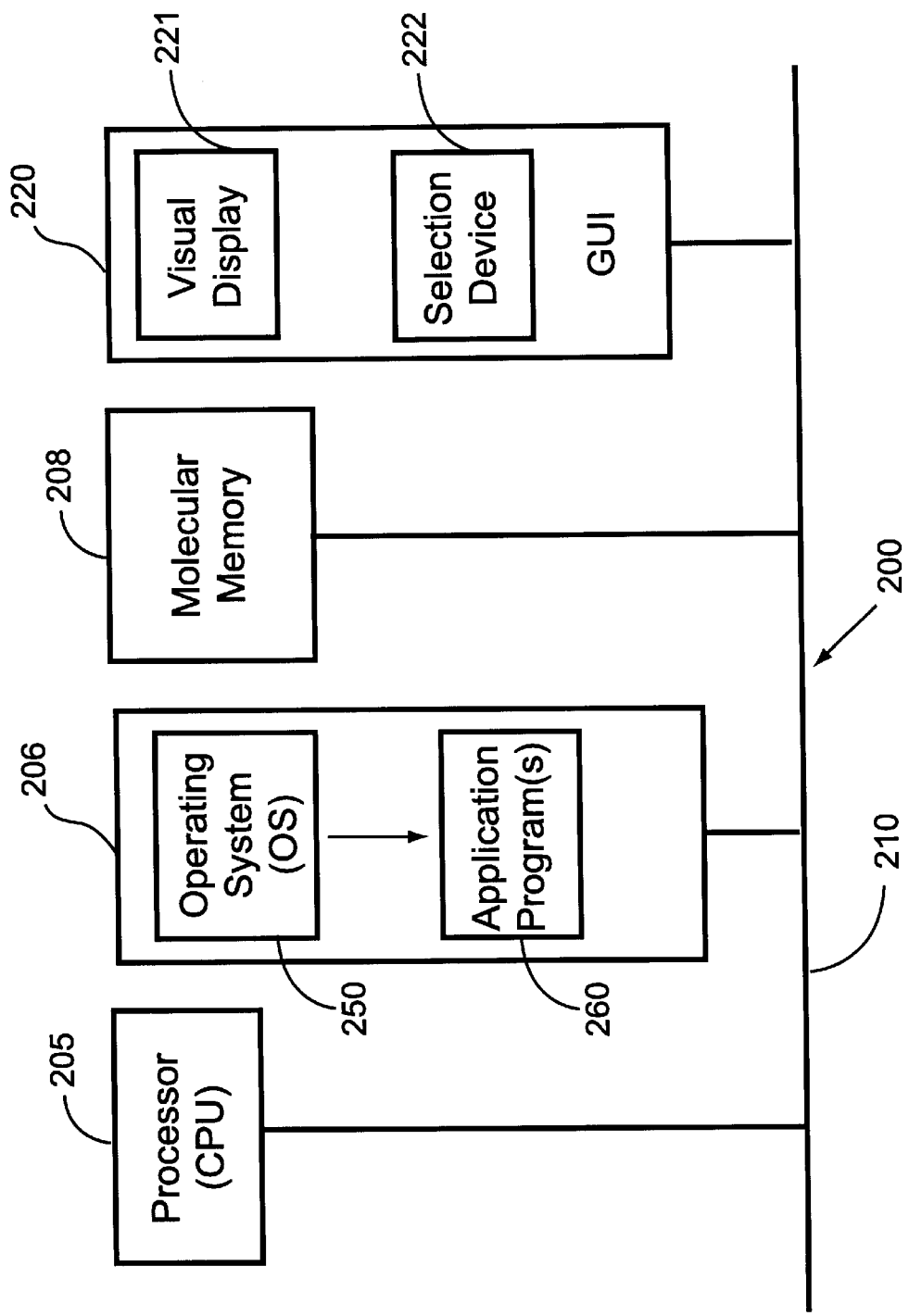
FIG. 9 illustrates the memory devices of this invention integrated into a standard computer architecture or computer system 200.
Figure 10:
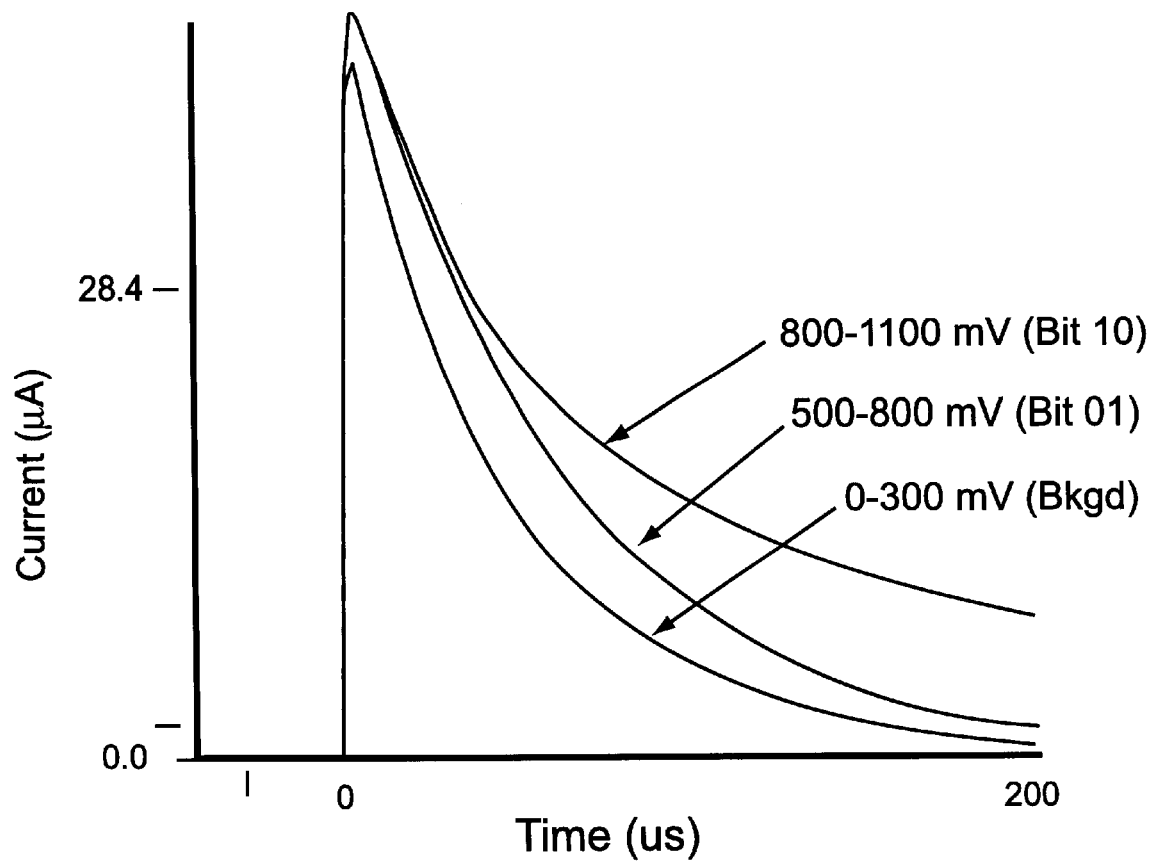
FIG. 10 illustrates the writing of bits on a porphyrin monolayer having two non-neutral oxidation states. A plot of current versus time at 3 applied voltages is illustrated. At 0–300 mV, no bit is set and the plot provides a background signal. At 500–800 mV and at 800–1100 mV the first and second bits are written, respectively.

The use of the storage devices of this invention in computer systems is contemplated. One such computer system is illustrated in FIG. 8. In one embodiment, the computer comprises a signal source (e.g. I/O device or CPU) a storage device of this invention and appropriate circuitry (e.g. voltammetry circuitry) to read the state(s) of the storage device. In operation, voltages representing the bits to be stored are applied to the working electrodes of the storage device thereby setting the memory. When retrieval is necessary (e.g. for output, or further processing) the state(s) of the storage device is read by the I/O circuitry and the information is passed off to other elements (e.g. CPU) in the computer.

Figure 11:
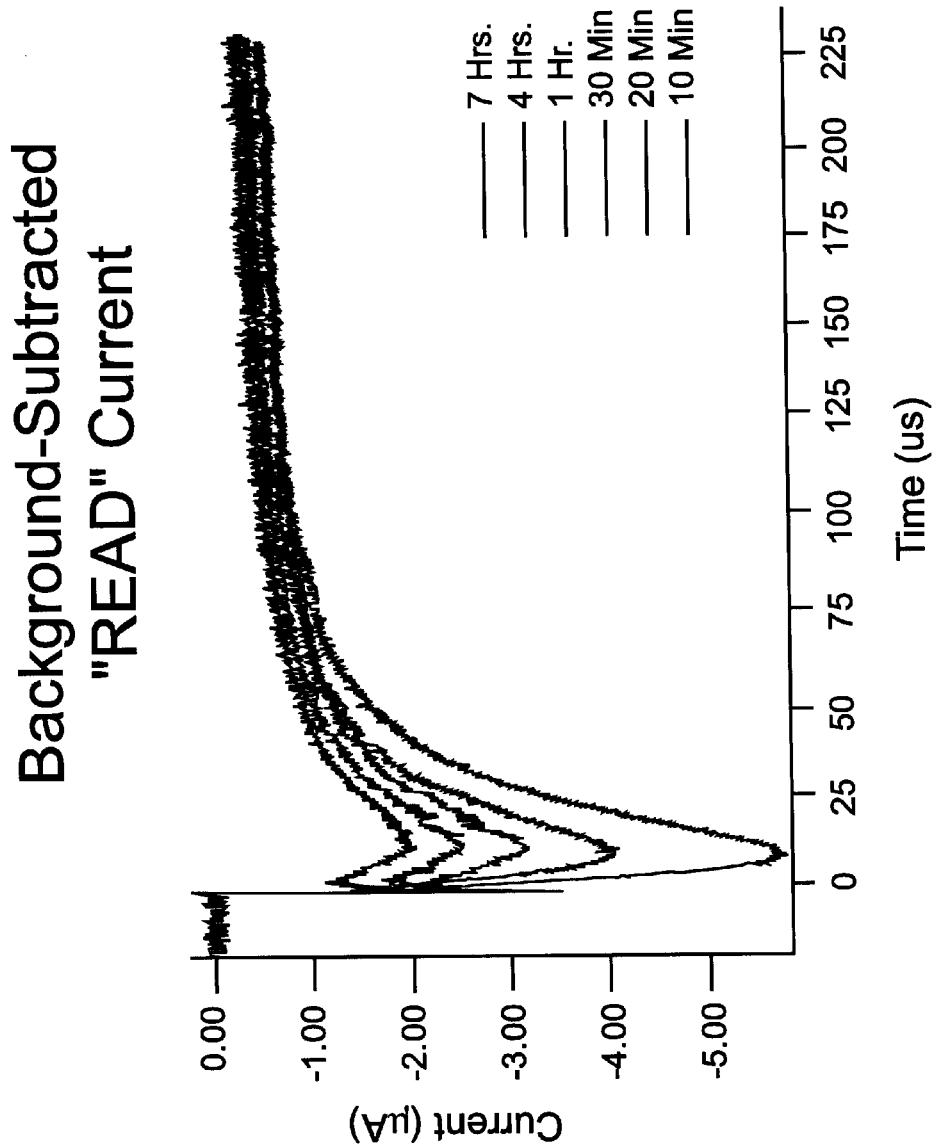
FIG. 11 illustrates the read/write of a monomeric porphyrin. Current is plotted as a function of potential.
Figure 12:
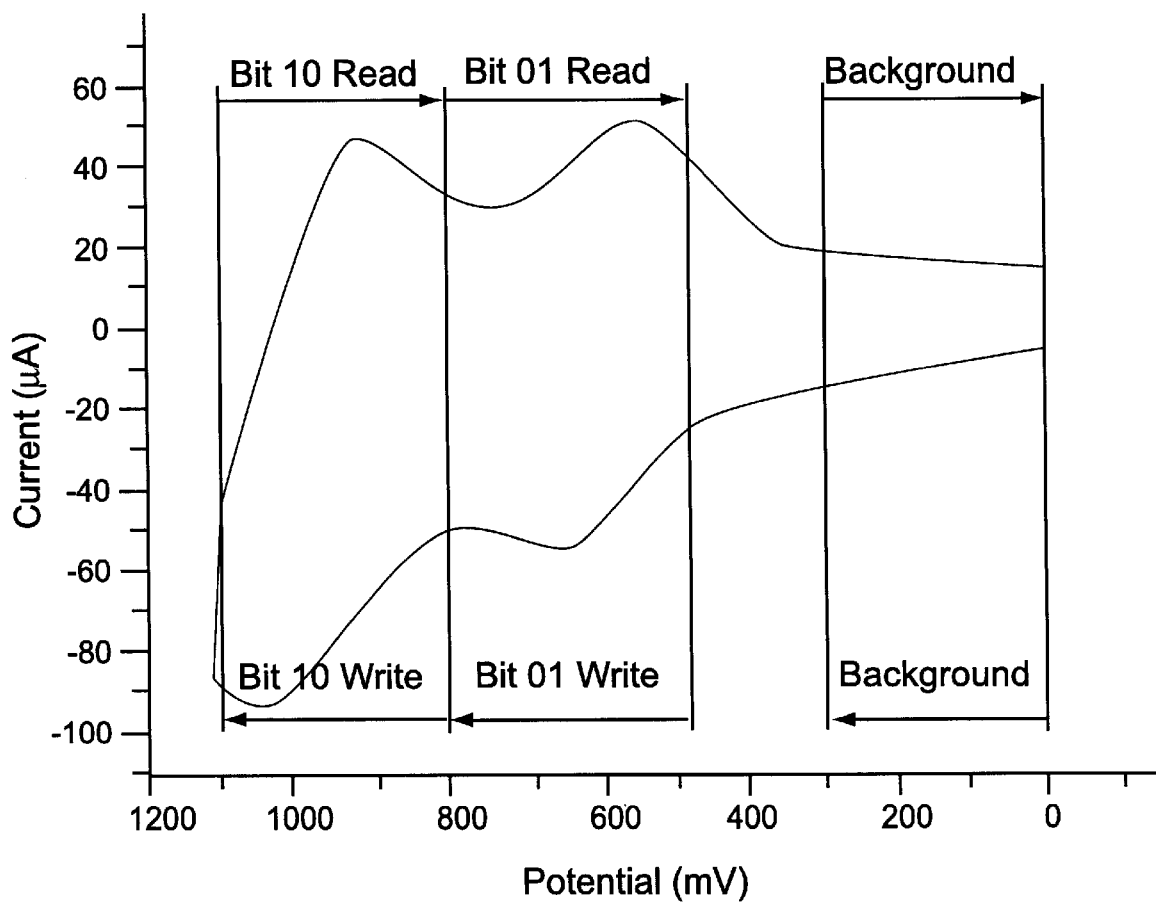
FIG. 12 illustrates background-subtracted faradaic read current.

FIG. 12 illustrates the memory devices of this invention integrated into a standard computer architecture or computer system 200. The hardware of system 200 includes a processor (CPU) 205, a memory 206 (which can comprise molecular memory devices), a persistent storage 208 which does comprise molecular memory devices of this invention, and, optionally, hardware for a graphical user interface (GUI) 220, coupled by a local bus or interface 210. The persistent memory 208 can include the elements shown in FIG. 11. System 200 can further include additional hardware components (not shown).

System 200 can be, for example, a personal computer or workstation. Processor 205 can be, for example, a microprocessor, such as the 80386, 80486 or Pentium(tm) microprocessor, made by Intel Corp. (Santa Clara, Calif.). Memory 206 can include, for example, random-access memory (RAM), read-only memory (ROM), virtual memory, molecular memory (FIG. 11) or any other working storage medium or media accessible by processor 205. Persistent storage 208 can include a hard disk, a floppy disk, an optical or magneto-optical disk, a molecular memory or any other persistent storage medium. GUI 220 facilitates communications between a user and system 200. Its hardware includes a visual display 221 and a selector device (mouse, keyboard, etc.) 222. Through visual display 221, system 200 can deliver graphical and textual output to the user. From selector device 222, system 200 can receive inputs indicating the user's selection of particular windows, menus, and menu items. Visual display 221 can include, for example, a cathode-ray tube (CRT) or flat-panel display screen, or a head-mounted display such as a virtual reality display. Selector device 222 can be, for example, a two-dimensional pointing device such as a mouse, a trackball, a track pad, a stylus, a joystick, or the like. Alternatively or additionally, selector device 222 can include a keyboard, such as an alphanumeric keyboard with function and cursor-control keys.

The software of system 200 includes an operating system 250 and an application program 260. The software of system 200 can further include additional application programs (not shown). Operating system 250 can be, for example, the Microsoft(r) Windows(tm) 95 operating system for IBM PC and compatible computers having or emulating Intel 80386, 80486, or Pentium(tm) processors. Alternatively, the operating system can be specialized for operation utilizing molecular memory elements. Application program 260 is any application compatible with the operating system and system 200 architecture. Persons of skill in the art will appreciate that a wide range of hardware and software configurations can support the system and method of the present invention in various specific embodiments.

EXAMPLES

The following examples are offered to illustrate, but not to limit the claimed invention.

Example 1

Tightly Coupled Porphyrin Arrays for Molecular Memory Storage

We have been developing approaches for molecular-based information storage where information is stored in the different oxidation states of molecular porphyrin arrays. To explore a simple design for suitable storage molecules, we report here the synthesis of porphyrin arrays where porphyrins, having identical oxidation potentials, are directly linked to one another instead of joined via a molecular linker. Oxidative coupling with $AgPF_6$ of zinc(II)-5,15-bis(4-tert-butylphenyl)-10-phenylporphyrin, obtained by a rational synthesis, afforded the expected meso,meso-linked dimer and an unexpected meso,meso,meso-linked trimer. For attachment to an electroactive surface we synthesized a meso,meso-linked porphyrin dimer with a thiol-linker in one of the meso-positions. The thiol-group was protected as thioacetyl moiety to avoid handling of free thiol groups. Coupling of zinc(II)-5,10,15-tris(3,5-di-tert-butylphenyl) porphyrin ("upper half") and zinc(II)-10,20-bis(3,5-di-tert-butylphenyl)-5-[4-(S-acetylthio)phenyl]porphyrin ("bottom half") afforded a set of three different meso,meso-linked dimers with the desired one as the main product. Electrochemical examination of the meso,meso-linked dimer in solution showed that the charge introduced upon oxidation of one of the porphyrin units shifts the oxidation potential of the adjacent porphyrin. Thereby two bits of information can be stored in such a structure. No significant shift of the oxidation potentials was observed in the trimer in this instance.

Introduction.

In order to simplify the construction of the arrays for molecular based information storage, we decided to synthesize porphyrin arrays where the porphyrins are directly linked to one another (Osuka and Shimidzu (1997) *Angew. Chem. Int. Ed. Engl.*, 36: 135–137; Yoshida et al. (1998) *Chem. Lett.* 55–56; Nakano et al. (1998) *Angew. Chem. Int. Ed.* 37: 3023–3027; Senge and Feng (1999) *Tetrahedron Lett.* 40: 4165–4168). We expected that the juxtaposition of the porphyrins in the arrays would result in strong ("tightly") coupling between the two constituents. This means that the charge introduced upon oxidation of one of the porphyrin units shifts the oxidation potential of the adjacent porphyrin. In this manner, identical porphyrins can be used in the construction of the multiporphyrin array while still maintaining the ability to access multiple oxidation states.

Storing and retrieving information in redox-active molecules requires a means of electrical communication from the macroscopic world to the molecular assemblies. One means of electrical communication involves the attachment of redox-active molecules via a thiol linker to an electroactive surface such as gold (Zak et al. (1993) *Langmuir* 9: 2772–2774; Postlethwaite et al. (1995) *Langmuir* 11: 4109–4116; Kondo et al. (1996) *Thin Solid Films* 284–285: 652–655; Simpson et al. (1996) *Analyst* 121: 1501–1505; Simpson et al. (1997) *Langmuir* 13: 460–464; Ishida et al. (1998) *Chem. Lett.* 267–268; Ishida et al. (1998) *Chem. Commun.* 57–58; Imahori et al. (1998) *Langmuir* 14: 5335–5338; Yanagida et al. (1998) *Bull. Chem. Soc. Jpn.* 71: 2555–2559). To overcome the problem of handling free thiol groups we decided to use protected thiol groups, especially after the report of Tour et al. that an S-acetylthio-substituted phenylethynyl oligomer underwent deprotection in situ upon exposure to the gold surface (Tour et al. (1995) *J. Am. Chem. Soc.* 117: 9529–9534). Recently we have synthesized a number of porphyrin monomers bearing one, two, or four protected thiol units and have investigated the utility of a variety of different thiol protecting groups (Gryko et al. (1999) *J. Org. Chem.* 64: 8634–8647).

In this example, we report the synthesis of five different meso,meso-linked porphyrin dimers and trimers. The electrochemical properties of the dimers and trimers have been investigated in solution. Two dimers bear acetyl protected thiol groups for attachment to gold surfaces.

Results and Discussion.

Our first target molecule was a meso,meso-linked porphyrin dimer of two identical porphyrin monomers. With this molecule we wanted to test if the juxtaposition affords strong coupling between the two porphyrin units, so that the redox potentials of the structurally identical porphyrin units are shifted by a reasonable amount.

Figure 13:
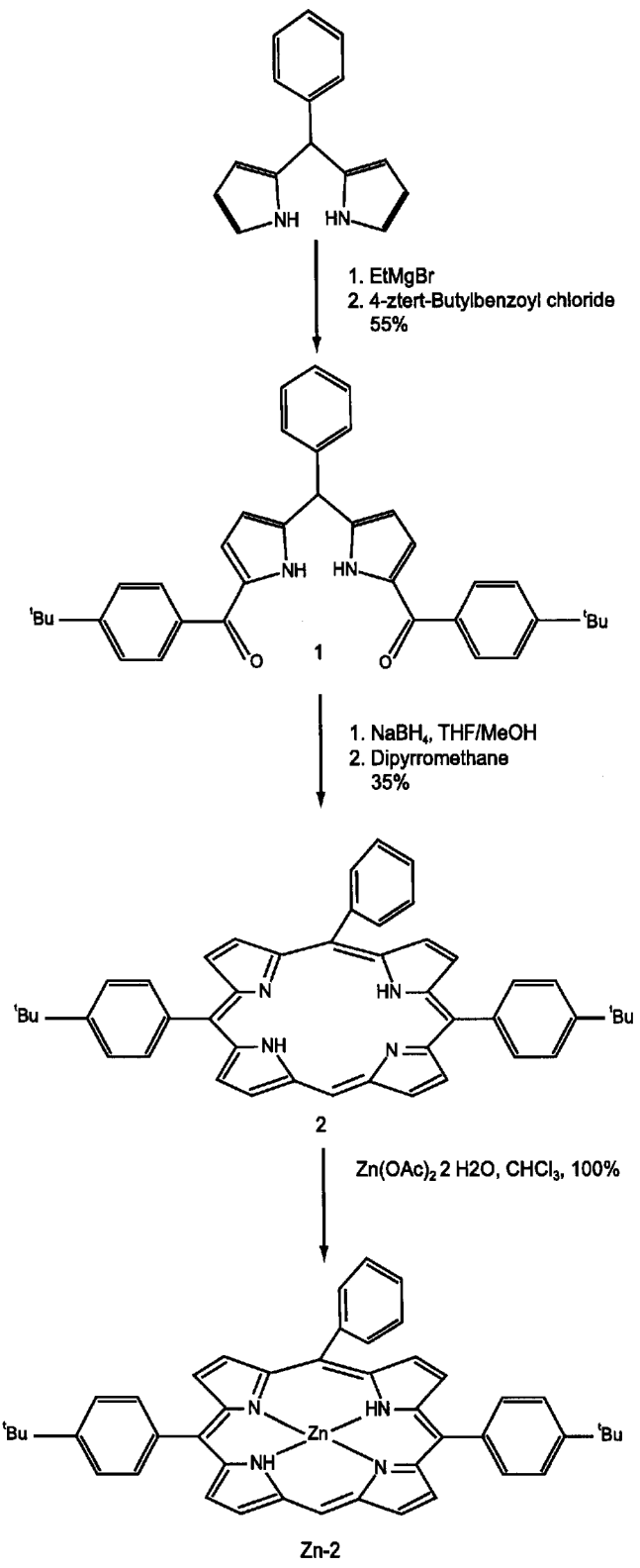
FIG. 13 shows synthesis scheme 1 for the synthesis of Zn-2 from 5-phenyldipyrromethane.

The preparation of the monomer utilized a new rational synthesis of meso-susbstituted porphyrins (Cho et al. (1999) *J. Org. Chem.* 64: 7890–7901). Treatment of 5-phenyldipyrromethane (Littler et al. (1999) *J. Org. Chem.* 64: 1391–1396) with ethyl magnesium bromide followed by acylation with 4-tert-butylbenzoyl chloride led to the diacylated dipyrromethane 1 (Scheme 1, FIG. 13). Reduction with excess $NaBH_4$ in THF/methanol afforded the corresponding diol, which was condensed with dipyrromethane (Lee and Lindsey (1994) *Tetrahedron* 50: 11427–11440; Littler et al. (1999) *J. Org. Chem.* 64: 1391–1396) under TFA catalysis. The desired porphyrin 2 was obtained in 35% yield as a purple solid. This synthesis route afforded the desired porphyrin with one free meso-position without acidolytic scrambling. Porphyrin 2 is almost insoluble in common solvents. Metalation with $Zn(OAc)_2 \cdot 2H_2O$ in refluxing $CHCl_3$ afforded Zn-2 in quantitative yield, which also has low solubility.

Figure 14:
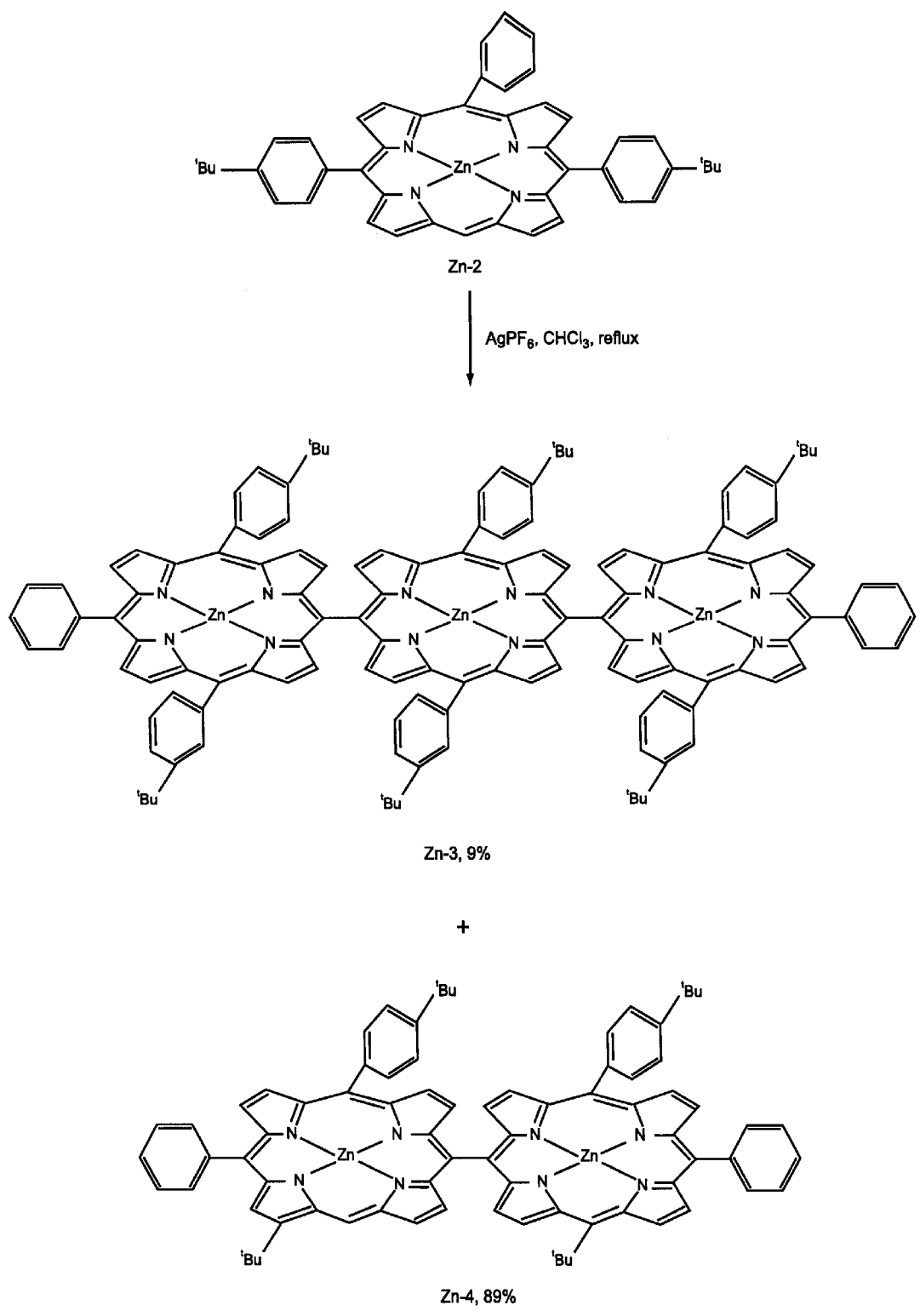
FIG. 14 shows synthesis scheme 2 for the synthesis of Zn-3 and Zn-4 from Zn-2.

For the meso,meso-linked coupling of Zn-2 we used the method reported by Osuka et al. (Osuka and Shimidzu (1997) *Angew. Chem. Int. Ed. Engl.*, 36: 135–137) which employed $AgPF_6$ in a mixture of $CHCl_3$ and acetonitrile as the oxidizing agent. Due to the low solubility of Zn-2 the reaction was run under reflux instead of room temperature. Using 0.5 mol equiv of $AgPF_6$ as reported by Osuka et al., supra., led only to a small amount of dimerization (~10%, checked by analytical SEC). After addition of another 0.5 mol equiv of $AgPF_6$, quantitative conversion occurred within 15 h. Because slight demetalation occurred under the coupling conditions, the crude mixture was again treated with $Zn(OAc)_2 \cdot 2H_2O$. We obtained two different oligomers, the expected dimer Zn-4 in 89% yield and, surprisingly, also the trimer Zn-3 in 9% yield (Scheme 2, FIG. 14). Both are brown-purple solids and exhibit good solubility in common solvents. The substitution pattern of Zn-3 was confirmed by its $^1H$ NMR spectrum, which is almost identical with that of Zn-4 with addition of a peak due to the tert-butyl groups and the presence of the AA'BB' pattern from the protons of the central aryl groups. Such a spectrum arises from a symmetrical molecule and the suggested structure is the only possibility for Zn-3.

Electrochemical examination of porphyrin dimer Zn-4 revealed oxidation waves at +0.49 and +0.66 V for the formation of the monocation of the two porphyrin units comprising porphyrin dimer Zn-4. This is to be compared with the single oxidation wave for the corresponding porphyrin monomer, which is expected at 0.58 V. The appearance of two waves in porphyrin dimer Zn-4 indicates that the oxidation of the first porphyrin unit, forming the monocation, shifts the oxidation potential of the second porphyrin unit to higher potential. A similar potential shift occurred for the second oxidation of each porphyrin unit (Table 1). The electrochemical examination of porphyrin trimer Zn-3 showed that only the oxidation potentials of the central porphyrin unit are shifted by the neighboring units. The two terminal porphyrin units do not significantly influence the oxidation potentials of each other and overlapping of the waves was observed.

Driven by the positive results for the porphyrin dimer Zn-4 we decided to synthesize a meso,meso-linked porphyrin dimer bearing a thiol linker for attachment to a gold surface. To improve the solubility of the monomers we chose 3,5-di-tert-butylphenyl groups as substituents for the non-linking meso-positions.

Figure 15:
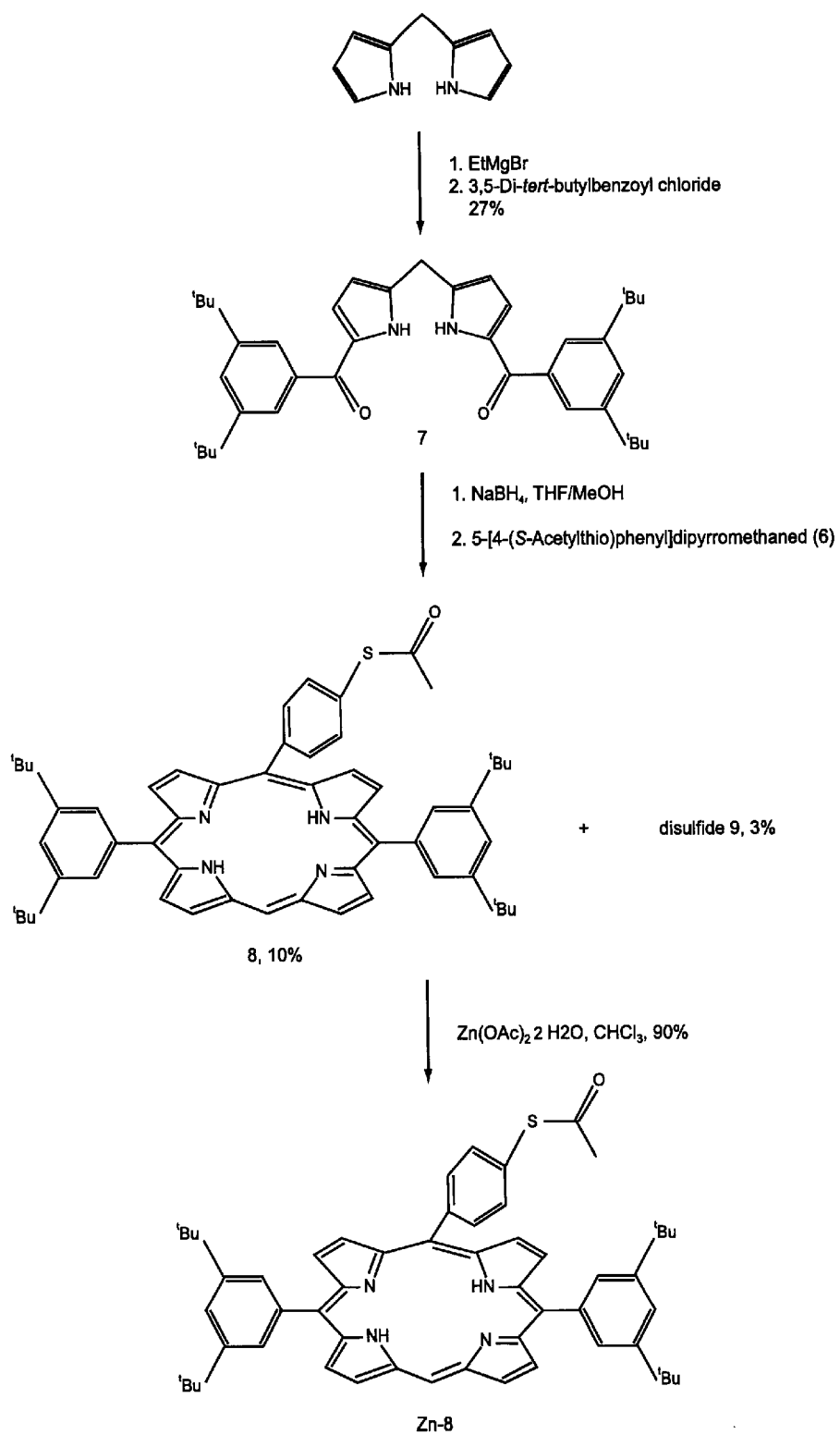
FIG. 15 shows synthesis scheme 3 for the synthesis of Zn-8.
Figure 16:
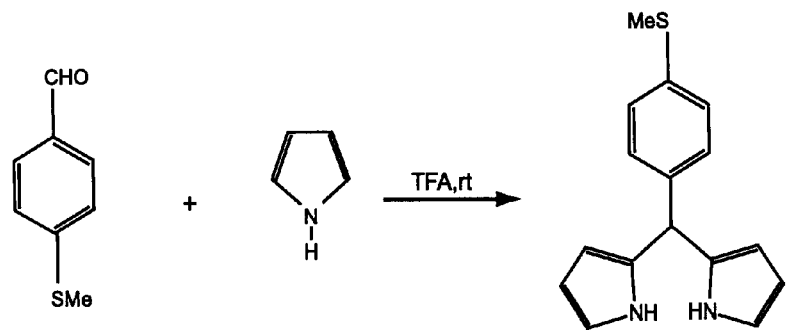
FIG. 16 shows equation 1 illustrating a first attempt to synthesize a dipyrromethane by reacting commercially available 4-methylthiobenzaldehyde with pyrrole to give the corresponding dipyrromethane (Gryko et al. (1999) *J. Org. Chem.* 64: 8634–8647). However, subsequent treatment with sodium tert-butoxide (Pinchart et al. (1999) *Tetrahedron Lett.* 40: 5479–5482), followed by quenching of the anion with acetyl chloride did not afford the desired product.
Figure 17:
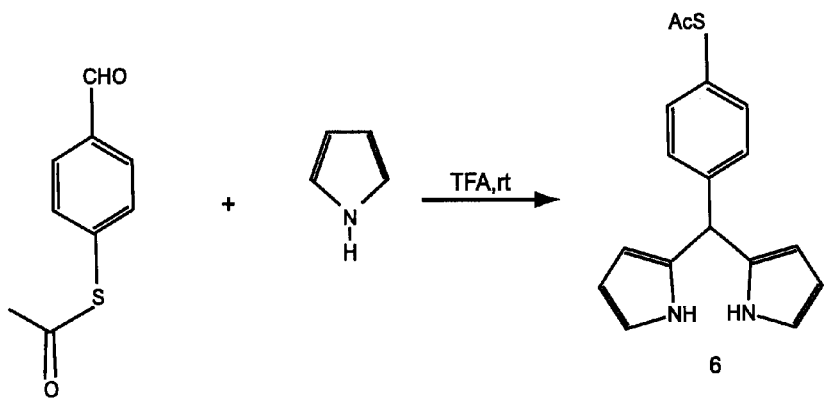
FIG. 17 shows Equation 2 illustrating the reaction of 4-S-acetylthiobenzaldehyde (Gryko et al. (1999) *J. Org. Chem.* 64: 8634–8647) with pyrrole to yield dipyrromethane 6.
Figure 18:
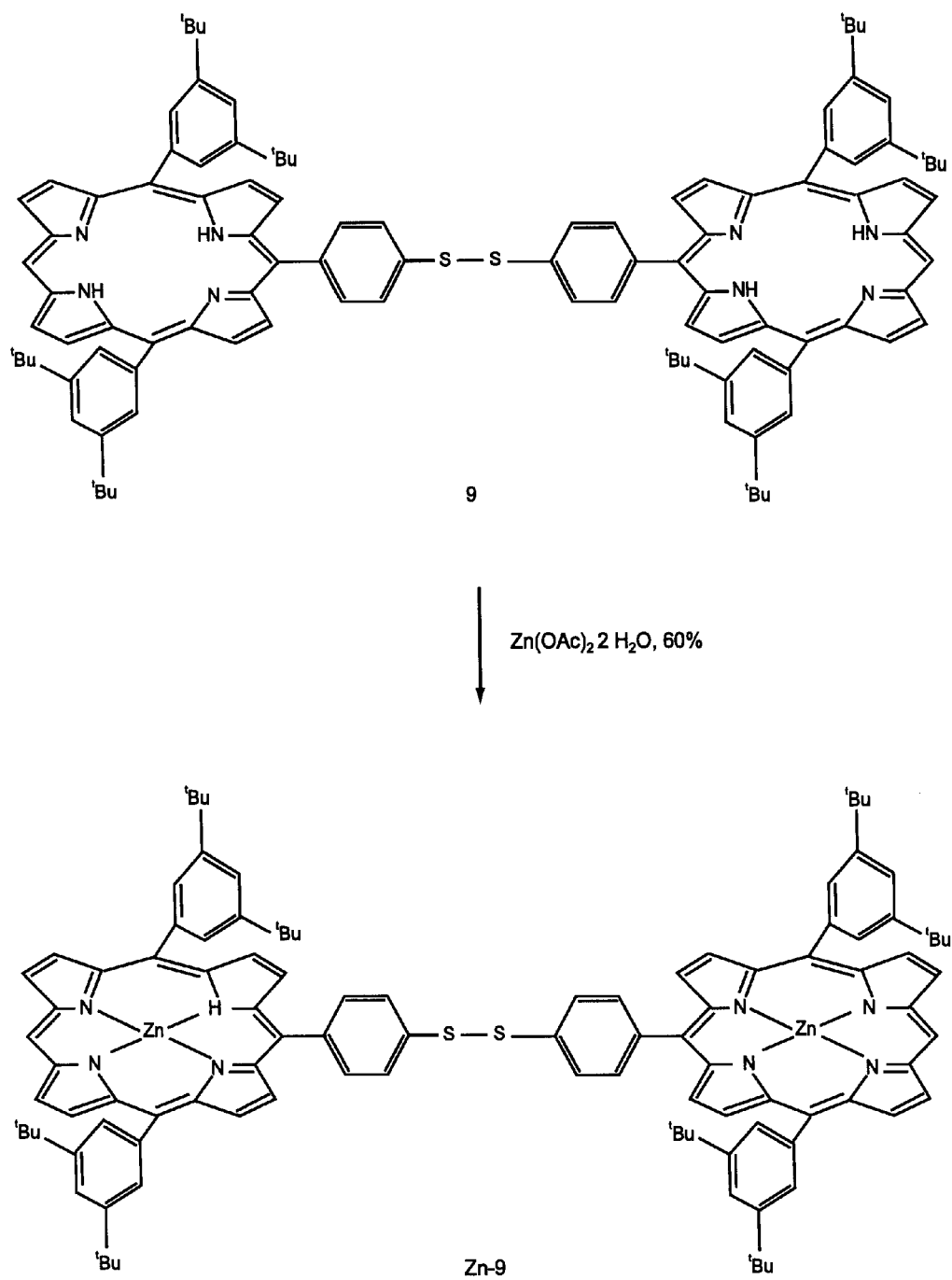
FIG. 18 shows synthesis scheme 4 for the synthesis of Zn-9.

The "bottom" porphyrin Zn-8 with the S-acetyl protected thiol group was synthesized in a similar way as for monomer Zn-2. Diacylation of dipyrromethane (Littler et al. (1999) *J. Org. Chem.* 64: 1391–1396) with 3,5-di-tert-butylbenzoyl chloride afforded dipyrromethane 7 as a white powder after crystallization (Scheme 3, FIG. 15). For the synthesis of dipyrromethane 6 there are at least two conceivable pathways. The first attempt to synthesize this molecule involved reaction of commercially available 4-methylthiobenzaldehyde with pyrrole to give the corresponding dipyrromethane (Gryko et al. (1999) *J. Org. Chem.* 64: 8634–8647). However, subsequent treatment with sodium tert-butoxide (Pinchart et al. (1999) *Tetrahedron Lett.* 40: 5479–5482), followed by quenching of the anion with acetyl chloride did not afford the desired product (equation 1, FIG. 16). In this situation we decided to change our strategy. Thus reaction of 4-S-acetylthiobenzaldehyde (Gryko et al. (1999) *J. Org. Chem.* 64: 8634–8647) with pyrrole afforded dipyrromethane 6 in 62% yield (equation 2, FIG. 17). Reduction of 7 to the corresponding diol and condensation with 6 under TFA catalysis yielded porphyrin 8 in 10% yield, accompanied by disulfide 9 in 3% yield. Metalation of 8 with $Zn(OAc)_2 \cdot 2H_2O$ gave Zn-8 as a purple solid in 90% yield. Disulfide 9 was metalated likewise, affording Zn-9 in 60% yield as an orange-purple solid (Scheme 4, FIG. 18).

Figure 19:
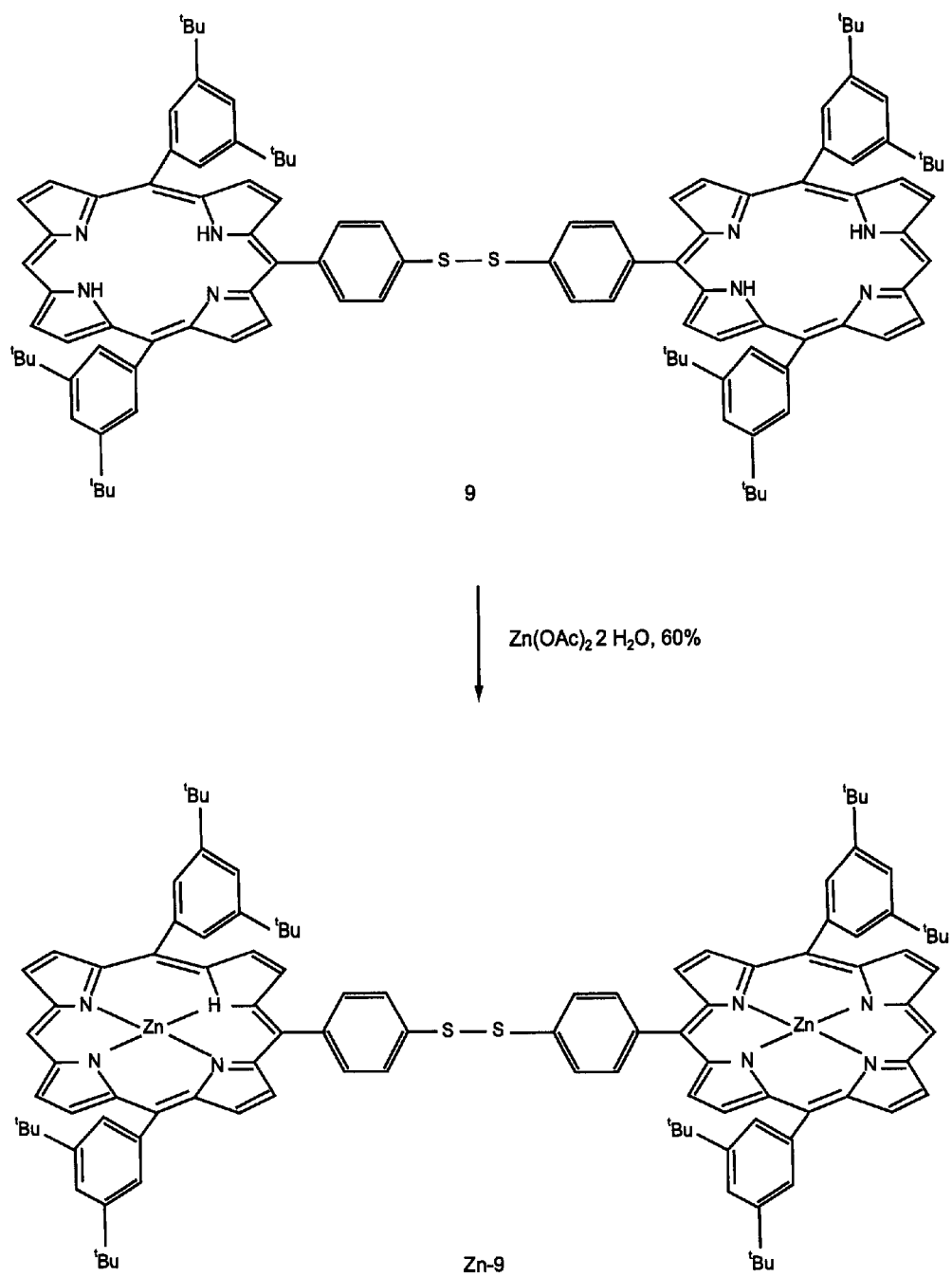
FIG. 19 shows synthesis scheme 5 for the synthesis of Zn-10.

The synthesis of the "top" porphyrin Zn-10 was done using the same method as before but in much better yield. Reduction of the diacylated dipyrromethane 7 with $NaBH_4$ and condensation of the resulting diol with 5-(3,5-di-tert-butylphenyl)dipyrromethane (Imahori et al. (1999) *Bull. Chem. Soc. Jpn*, 72: 485–502) under TFA catalysis afforded porphyrin 10 as a purple solid in 21% yield (Scheme 5, FIG. 19). Metalation with $Zn(OAc)_2 \cdot 2H_2O$ led to Zn-10 as a red-purple solid in quantitative yield. Zn-10, like all the other porphyrin monomers (8, Zn-8 and 10) and disulfides (9 and Zn-9) bearing 3,5-di-tert-butylphenyl groups in the meso-positions, exhibits good solubility in common solvents.

Figure 20:
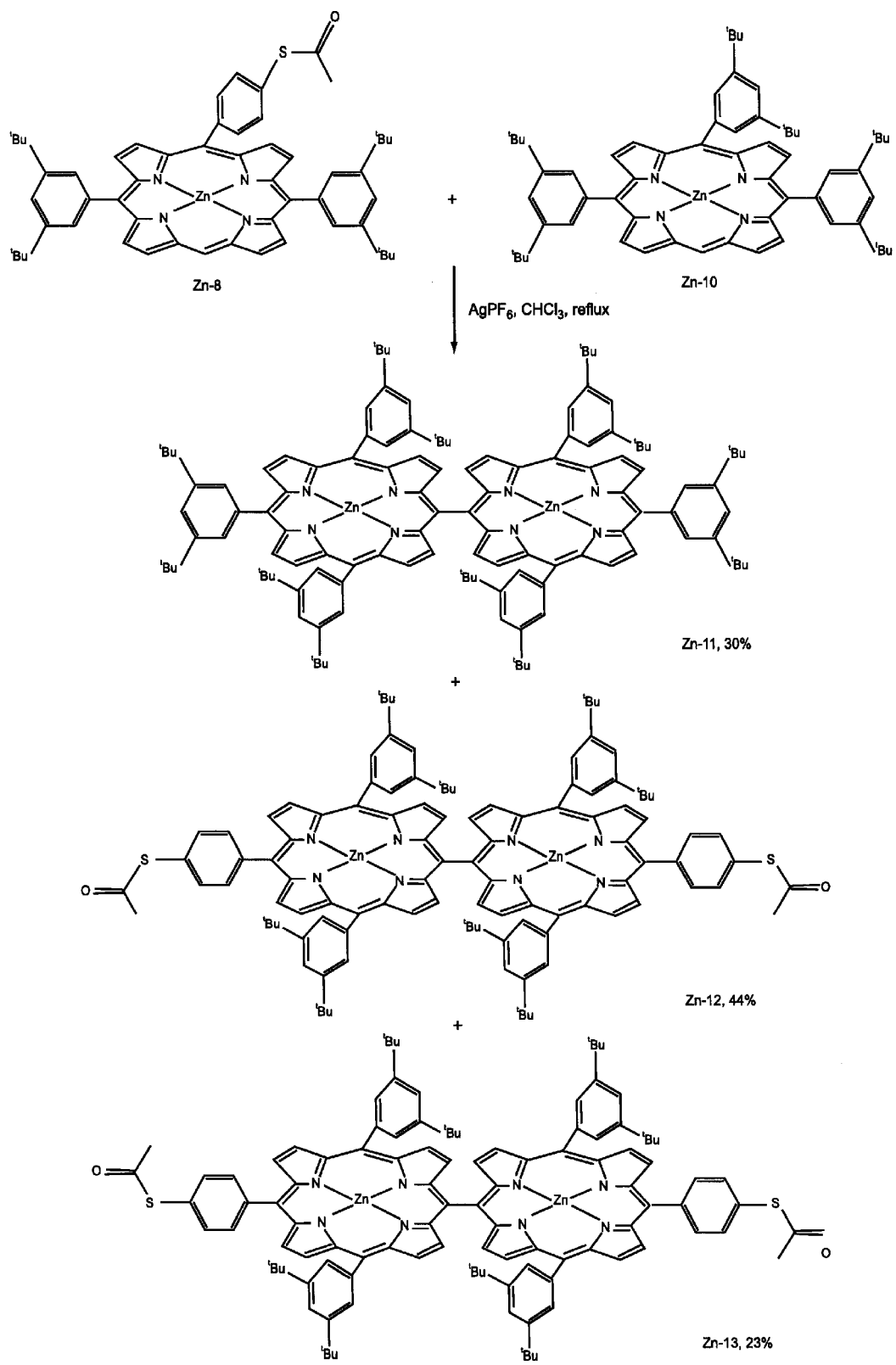
FIG. 20 shows synthesis scheme 6 for the synthesis of Zn-13.

Coupling of Zn-8 and Zn-10 with $AgPF_6$ in refluxing $CHCl_3$ afforded the expected three dimers in almost quantitative yield. Traces of higher oligomers were also present. After remetalation with $Zn(OAc)_2 \cdot 2H_2O$ we obtained porphyrin dimers Zn-11, Zn-12 and Zn-13 in 30%, 44% and 23% yield, respectively (Scheme 6, FIG. 20). All porphyrin dimers are purple solids with good solubility in common solvents. Under these reaction conditions the acetylthio group remained intact.

Conclusion.

Various meso,meso-linked porphyrin dimers and trimers have been synthesized. The electrochemical studies of the dimers in solution revealed a shift of the oxidation potential for the generation of the monocation of the second porphyrin unit after oxidation of the first porphyrin unit. This shift in the oxidation potentials of the individual porphyrin units provides an opportunity to access distinct and different oxidation potentials in a dimeric array where each porphyrin unit is identical. The effect was small in the trimers tested herein.

Experimental

General.

All reactions involving porphyrin formation and transformation were performed with shielding from ambient light. All chemicals obtained commercially were used as received unless noted otherwise. Reagent grade solvents ($CH_2Cl_2$, $CHCl_3$, hexanes, ethyl ether, ethyl acetate) and HPLC grade solvents (acetonitrile, toluene) were used as received from Fisher. THF was distilled from sodium/benzophenone. All reported NMR spectra were obtained at 300 MHz. UV-Vis absorption and fluorescence spectra were recorded in toluene. Flash chromatography was performed on flash silica (Baker, 200–400 mesh) or alumina (Fisher, 80–200 mesh). Mass spectra were obtained via laser desorption (LD-MS) in the absence of an added matrix using a Bruker Proflex II mass spectrometer, fast atom bombardment (FAB-MS) using a JEOL HX100HF mass spectrometer (ion source 40° C., CsKI or polyethylene glycol standards, 10 ppm elemental compositional accuracy for the porphyrins), or electron-impact mass spectrometry (EI-MS). Porphyrin metalation was monitored by fluorescence excitation and emission spectroscopy. Preparative scale size exclusion chromatography (SEC) was performed using BioRad Bio-Beads SX-1 with toluene as eluent. The chromatography was performed with gravity flow. Analytical scale SEC was performed with a Hewlett-Packard 1090 HPLC using a 1000 Å column (5 μL, styrene-divinylbenzene copolymer) with THF as eluent.

General Procedure for Metal Insertion.

A solution of porphyrin in $CHCl_3$ or $CH_2Cl_2$ and a solution/suspension of the metal acetate in methanol were combined and stirred. After the metalation was completed (checked by fluorescence excitation spectroscopy), $H_2O$ was added. The phases were separated and the organic layer was washed three times with 5% $NaHCO_3$ and dried ($Na_2SO_4$). The solvents were removed under reduced pressure. Purification was done by column chromatography over flash silica gel.

1,9-Bis(4-tert-butylbenzoyl)-5-phenyldipyrromethane (1)

To a solution of 5-phenyldipyrromethane (Lee and Lindsey (1994) *Tetrahedron* 50: 11427–11440; Littler et al. (1999) *J. Org. Chem.* 64: 1391–1396) (2.22 g, 10 mmol) in toluene (200 mL) stirred under argon and cooled in a water bath was slowly added a solution of ethyl magnesium bromide (1 M solution in THF, 50 mL, 50 mmol). The resulting brown-orange mixture was stirred for 30 min. Then a solution of 4-tert-butylbenzoyl chloride (4.9 mL, 25.1 mmol) in toluene (25 mL) was added dropwise. The solution became darker and was stirred for 1 h after the addition was completed. Then the reaction was quenched with satd aq $NH_4Cl$ (100 mL). Ethyl acetate (100 mL) was added and the phases were separated. The organic phase was washed with water, 2 M aq NaOH, water and brine and then dried ($Na_2SO_4$). The solvents were removed under reduced pressure and the residue was filtered through a pad of silica and eluted with $CH_2Cl_2$/ethyl acetate 10:1. The solvents were again removed under reduced pressure and the brown residue was purified by column chromatography (1st column: alumina, hexanes —CH$_2$Cl$_2$/hexanes —CH$_2$Cl$_2$— CH$_2$Cl$_2$/MeOH; 2$_{nd}$ column: silica, ethyl ether/hexanes 1:2; 3$^{rd}$ column: silica: CH$_2$Cl$_2$/ethyl acetate 5:1), affording 2.96 g (5.5 mmol, 55%) as a brown solid. mp 133° C.; IR (neat): ν=3438, 3251, 2963, 2903, 2868, 1611, 1556, 1479; $^1$H NMR (300.5 MHz, CDCl$_3$): δ=1.34 (s, 18H), 5.67 (s, 1H), 6.00 (dd, 2H, $^3$J=3.7 Hz, $^4$J=2.9 Hz), 6.64 (dd, 2H, $^3$J=3.7 Hz, $^4$J=2.2 Hz), 7.30–7.51 (m, 5H), 7.42, 7.73 (AA',BB', 2×4H), 11.04 (br, s, 2H); $^{13}$C NMR (75.6 MHz, CDCl$_3$, ATP): δ=31.1 (–), 34.9 (+), 44.9 (–), 111.0 (–), 120.6 (–), 124.9 (–), 127.3 (–), 128.8 (–), 129.2 (–), 129.5 (–), 131.0 (+), 135.6 (+), 140.5 (+), 140.8 (+), 155.0 (+), 184.3 (+); EI obsd 542, 527, 465, 409, 381, 316; Anal. Calcd. for C$_{37}$H$_{38}$N$_2$O$_2$: C, 81.88; H, 7.06; N, 5.16; Found: C, 81.79; H, 7.22; N, 5.21.

5,15-Bis(4-tert-butylphenyl)-10-phenylporphyrin (2)

To a solution of 1 (500 mg, 921 μmol) in a 1:2 mixture of methanol/THF (27 mL) was added NaBH$_4$ (1.74 g, 46 mmol) in several portions. The mixture was stirred for 2.5 h, then quenched with water (40 mL) and extracted with CH$_2$Cl$_2$. The organic phase was dried (K$_2$CO$_3$) and the solvents were removed under reduced pressure. The yellow residue and dipyrromethane (Littler et al. (1999) *J. Org. Chem.* 64: 1391–1396) (135 mg, 923 μmol) were then dissolved in acetonitrile and stirred at room temperature in the dark. Then TFA (852 μL, 11.1 mmol) was added and the solution turned dark immediately. After 20 min DDQ (630 mg, 2.8 mmol) was added because the yield did not increase any further (checked by oxidizing an aliquot with DDQ and quantifying with UV/VIS spectroscopy). After stirring for 1.5 h the mixture was filtered through a pad of alumina and eluted with CH$_2$Cl$_2$. The solvents were removed under reduced pressure and the residue was dissolved in a mixture of CH$_2$Cl$_2$/hexanes 1:1. Purification by column chromatography (silica, CH$_2$Cl$_2$/hexanes 1:1 —CH$_2$Cl$_2$) afforded 211 mg (324 μmol, 35%) of a purple solid. IR (neat): ν=3312, 3030, 2957, 2864, 1596, 1560, 1500; $^1$H NMR (300.5 MHz, CDCl$_3$): δ=2.99 (s, 2H), 1.62 (s, 18H), 7.70–7.82 (m, 3H), 7.78, 8.18 (AA',BB', 2×4H), 8.14–8.24 (m, 2H), 8.85 (d, 2H, $^3$J=5.1 Hz), 8.95 (d, 2H, $^3$J=5.1 Hz), 9.06 (d, 2H, $^3$J=4.4 Hz), 9.33 (d, 2H, $^3$J=4.4 Hz), 10.20 (s, 1H); LD-MS obsd 649.9; FAB-MS obsd 650.3416, calcd exact mass 650.3409 (C$_{46}$H$_{42}$N$_4$); λ$_{abs}$ (toluene) 415, 509, 543, 586, 641 nm.

Zinc(II)-5,15-bis(4-tert-butylphenyl)-10-phenylporphyrin (Zn-2)

A suspension of 2 (112 mg, 172 μmol) in CHCl$_3$ (50 mL) and a solution of Zn(OAc)$_2$·2H$_2$O (3.78 g, 172 mmol) in methanol (10 mL) were combined and refluxed 2 h. The solvents were removed under reduced pressure to afford 123 mg (172 μmol, 100%) of a bright purple solid. IR (neat): ν=3081, 3022, 2956, 1498; $^1$H NMR (300.5 MHz, CDCl$_3$): δ=1.63 (s, 18H), 7.71–7.83 (m, 3H), 7.78, 8.17 (AA'BB', 2×4H), 8.20–8.25 (m, 2H), 8.96 (d, 2H, $^3$J=5.1 Hz), 9.04 (d, 2H, $^3$J=5.1 Hz), 9.14 (d, 2H, $^3$J=4.4 Hz), 9.40 (d, 2H, $^3$J=4.4 Hz), 10.25 (s, 1H); LD-MS obsd 714.1; FAB-MS obsd 712.2565, calcd exact mass 712.2544 (C$_{46}$H$_{40}$N$_4$Zn); λ$_{abs}$ (toluene) 419, 544, 582 nm; λ$_{em}$ (toluene) 592, 639 nm.

Meso-meso-meso porphyrin trimer Zn-3 and meso-meso porphyrin dimer Zn-4

To a suspension of Zn-2 (31.1 mg, 43.5 μmol) in CHCl$_3$ (20 mL) was added a solution of AgPF$_6$ (5.5 mg, 21.8 μmol) in acetonitrile (3 mL). The mixture was refluxed for 8 h. Then more AgPF$_6$ (5.5 mg, 21.8 μmol) was added because the reaction stopped (monitored by analytical SEC). After an additional 15 h the reaction was quenched with water (30 mL). The phases were separated and the organic phase was washed with water and dried (Na$_2$SO$_4$). The solvents were removed under reduced pressure. The brown-purple solid was dissolved again in CHCl$_3$ (30 mL). A solution of Zn(OAc)$_2$·2H$_2$O (290 mg, 1.3 mmol) in methanol (7 mL) was added and the mixture was stirred for 3 h in the dark. Then the reaction was quenched with water and the phases were separated. The organic phase was washed three times with 5% aq NaHCO$_3$ and dried (Na$_2$SO$_4$). The solvents were removed under reduced pressure and the residue was dissolved in a minimum amount of toluene. Purification by preparative SEC with toluene afforded 2.8 mg of the meso,meso,meso-trimer (1.4 μmol, 9% yield) as a brown solid and 27.6 mg of the meso,meso-dimer (19.3 μmol, 89% yield) as a brown-purple solid. Zn-3: IR (neat): ν=2959, 2922, 2854, 1542, 1458; $^1$H NMR (300.5 MHz, CDCl$_3$): δ=1.54 (s, 18H), 1.56 (s, 36H), 7.59, 8.15 (AA'BB', 2×4H), 7.70, 8.18 (AA'BB', 2×8H), 7.78–7.85 (m, 6H), 8.15–8.22 (m, 4H), 8.23 (d, 4H, $^3$J=4.4 Hz), 8.30–8.36 (m, 4H), 8.76 (d, 4H, $^3$J=4.4 Hz), 8.77 (d, 4H, $^3$J=4.4 Hz), 9.03 (d, 4H, $^3$J=4.4 Hz), 9.07 (d, 4H, $^3$J=4.4 Hz); LD-MS obsd 2056.8 [M$^+$], 2000.7 [M$^+$-$^t$Bu]; FAB-MS obsd 2062.68, calcd exact mass 2062.70 (C$_{132}$H$_{112}$N$_{12}$Zn$_3$); λ$_{abs}$ (toluene) 419, 477, 567 nm; λ$_{em}$ (toluene) 641, 664 nm; Zn-4: IR (neat): =2958, 2868, 1558, 1488; $^1$H NMR (300.5 MHz, CDCl$_3$): δ=1.52 (s, 36H), 7.67, 8.15 (AA'BB', 2×8H), 7.74–7.86 (m, 6H), 8.18–8.20 (m, 4H), 8.31 (d, 4H, $^3$J=3.7 Hz), 8.71 (d, 4H, $^3$J=4.4 Hz), 9.01 (d, 4H, $^3$J=4.4 Hz), 9.04 (d, 4H, $^3$J=4.4 Hz); LD-MS obsd 1423.7; FAB-MS obsd 1422.48, calcd exact mass 1422.49 (C$_{92}$H$_{78}$N$_8$Zn$_2$); λ$_{abs}$ (toluene) 421, 459, 561 nm; λ$_{em}$ (toluene) 634, 659 nm.

5-[4-Methylthiophenyl]dipyrromethane (5)

Pyrrole (50.0 mL, 720 mmol) and 4-methylthiobenzaldehyde (3.83 mL, 28.8 mmol) were added to a 250 mL flask and degassed with a stream of argon. Then TFA (0.22 mL) was added and the mixture was stirred under argon at room temperature for 5 min and quenched with 0.1 M NaOH. Ethyl acetate was then added and the phases were separated. The organic phase was washed with water and dried (Na$_2$SO$_4$). Then the solvent was removed under vacuum to afford an orange oil. Bulb-to-bulb distillation (200° C., 0.01 mmHg) gave a yellow oil. The oil was dissolved in EtOH and addition of a small amount of water afforded white crystals (5.00 g, 64.7%). mp 94–95° C.; $^1$H NMR δ 2.51 (s, 3H), 5.43 (s, 1H), 5.95 (s, 2H), 6.21 (m, 2H), 6.69 (m, 2H), 7.17, 7.25 (AA'BB', 2×2H), 7.87 (br, s, 2H); $^{13}$C NMR δ 16.6, 44.1, 108.0, 109.2, 118.1, 127.6, 129.6, 133.1, 137.7, 139.8; EI-MS obsd 268.1033 (M$^+$), calcd exact mass 268.1034; Anal. Calcd. for C$_{16}$H$_{16}$N$_2$S: C, 71.60; H, 6.01; N, 10.44; S, 11.95; Found: C, 71.60; H, 5.99; N, 10.31; S, 11.81.

5-[4-(S-Acetylthio)phenyl]dipyrromethane (6)

Pyrrole (34.0 mL, 489 mmol) and 4-(S-acetylthio) benzaldehyde ((Gryko et al. (1999) *J. Org. Chem.* 64: 8634–8647) (3.50 g, 19.4 mmol) were added to a 100 mL flask and degassed with a stream of argon. Then TFA (0.15 mL, 1.94 mmol) was added and the mixture was stirred under argon at room temperature for 5 min and quenched with DIEA (0.330 mL, 1.94 mmol). All volatile materials were evaporated under high-vacuum. The crude mixture was filtered through a pad of silica to afford a yellow oil, which was dissolved in EtOH and allowed to stand at −20° C. for 3 days. Yellowish crystals were isolated by filtration. The filtrate was concentrated, a small amount of water was added and the mixture was allowed to stand at −20° C. for a few days, affording a second crop of crystals (3.56 g, 62.0%). mp 100–101° C.; $^1$H NMR δ 2.44 (s, 3H), 5.40 (s, 1H), 5.90 (s, 2H), 6.18 (m, 2H), 6.62 (m, 2H), 7.20, 7.34 (AA'BB', 2×2H), 7.97 (br, s, 2H); $^{13}$C NMR δ 31.0, 44.3, 108.2, 108.9, 118.3, 126.8, 130.1, 132.8, 135.3, 144.7, 195.7; EI-MS obsd 296.0996 (M$^+$), calcd exact mass 296.0983; Anal. calcd. for $C_{17}H_{16}N_2OS$: C, 68.89; H, 5.44; N, 9.45; S, 10.82; Found: C, 68.69; H, 5.56; N, 9.39; S, 10.91.

1,9-Bis(3,5-di-tert-butylbenzoyl)dipyrromethane (7)

To a solution of dipyrromethane (Littler et al. (1999) *J. Org. Chem.* 64: 1391–1396) (421 mg, 2.9 mmol) in toluene (60 mL) stirred under argon and cooled in a water bath was slowly added a solution of ethyl magnesium bromide (1 M solution in THF, 14.4 mL, 14.4 mmol). The resulting brown-orange mixture was stirred for 30 min at ambient temperature. 3,5-Di-tert-butylbenzoic acid was refluxed in thionyl chloride in the presence of 1 vol % DMF. A colorless liquid, bp 167° C. (water suction pump) was obtained in 89% yield. A solution of 3,5-di-tert-butylbenzoyl chloride (1.82 g, 7.2 mmol) in toluene (8 mL) was added dropwise to the brown-orange mixture. The solution became darker and was stirred for 2 h after the addition was completed. Then the reaction was quenched with satd aq NH$_4$Cl (30 mL). Ethyl acetate (60 mL) was added and the phases were separated. The organic phase was washed with water, 2 M aq NaOH, water and brine and then dried (Na$_2$SO$_4$). The solvents were removed under reduced pressure and the residue was filtered through a pad of silica and eluted with CH$_2$Cl$_2$/ethyl acetate 6:1–5:3. The solvents were again removed under reduced pressure and the residue was dissolved in a small amount of ethyl acetate. Hexanes was added until turbidity occurred. The mixture was cooled overnight at −20° C. and filtered, affording 442 mg (0.8 mmol, 27%) of a white powder. mp 220° C.; IR (neat): ν=3263, 2963, 1607, 1582, 1485; $^1$H NMR (300.5 MHz, CDCl$_3$): δ=1.32 (s, 36H), 4.27 (s, 2H), 6.17–6.13 (m, 2H), 6.71–6.77 (m, 2H), 7.57 (s, 2H), 7.72 (s, 4H), 11.47 (br, s, 2H); $^{13}$C NMR (75.6 MHz, CDCl$_3$, ATP): δ=26.8 (+), 31.3 (−), 34.9 (+), 110.0 (−), 121.1 (−), 123.6 (−), 125.6 (−), 131.2 (+), 137.5 (+), 138.0 (+), 150.5 (+), 185.6 (−); Anal. Calcd. for $C_{39}H_{50}N_2O_2$: C, 80.93; H, 8.71; N, 4.84; Found: C, 80.69; H, 8.72; N, 4.85.

10,20-Bis(3,5-di-tert-butylphenyl)-5-[4-(S-acetylthio)phenyl]porphyrin (8)

To a solution of 7 (397 mg, 686 μmol) in a 1:2 mixture of methanol/THF (21 mL) under argon was added NaBH$_4$ (1.30 g, 34 mmol) in several portions. The mixture was stirred for 2.5 h, then quenched with water (40 mL) and extracted with CH$_2$Cl$_2$. The organic phase was dried (K$_2$CO$_3$) and the solvents were removed under reduced pressure. The yellow foam obtained and 5-[4-(S-acetylthio) phenyl]dipyrromethane 6 (204 mg, 686 μmol) were dissolved in acetonitrile and stirred at room temperature. Then TFA (640 μL, 8.3 mmol) was added and the solution immediately turned dark blue. After 25 min DDQ (467 mg, 2.1 mmol) was added because the yield did not increase any further (checked by oxidizing an aliquot with DDQ and quantifying with UV/VIS spectroscopy). After 1.5 h the mixture was filtered through a pad of alumina and eluted with CH$_2$Cl$_2$. The solvents were removed under reduced pressure and the residue was purified by column chromatography on silica (1$^{st}$ column: CH$_2$Cl$_2$/hexanes 1:4–1:1, 2$^{nd}$ column: CH$_2$Cl$_2$/hexanes 1:2). Two fractions of brown-purple solids were obtained, yielding 14 mg of the disulfide 9 (9 μmol, 3% yield) and 57 mg of 8 (68 μmol, 10% yield). 9: IR (neat): ν=3316, 2961, 2924, 2854, 1592, 1466; $^1$H NMR (300.5 MHz, CDCl$_3$): δ=−2.94 (s, 4H), 1.52 (s, 72H), 7.79 (t, 4H, $^4$J=1.5 Hz), 8.10, 8.30 (AA'BB', 2×4H), 8.10 (d, 8H, $^4$J=1.5 Hz), 8.94 (d, 4H, $^3$J=5.1 Hz), 8.96 (d, 4H, $^3$J=5.1 Hz), 9.07 (d, 4H, $^3$J=5.1 Hz), 9.34 (d, 4H, $^3$J=4.4 Hz), 10.22 (s, 2H); LD-MS obsd 1589.4 [M$^+$], 793.4 [M$^+$/2]; FAB-MS obsd 1586.87, calcd exact mass 1586.86 ($C_{108}H_{114}N_8S_2$); $λ_{abs}$ (toluene) 417, 511, 544, 586, 642 nm. 8: IR (neat): ν=3307, 2958, 2861, 1708, 1590, 1467; $^1$H NMR (300.5 MHz, CDCl$_3$): δ=−2.95 (s, 2H), 1.55 (s, 36H), 2.60 (s, 3H), 7.81, 8.28 (AA'BB', 2×2H), 7.82 (t, 2H, $^4$J=1.5 Hz), 8.12 (d, 4H, $^4$J=1.5 Hz), 8.88 (d, 2H, $^3$J=5.1 Hz), 8.97 (d, 2H, $^3$J=5.1 Hz), 9.08 (d, 2H, $^3$J=5.1 Hz), 9.35 (d, 2H, $^3$J=4.4 Hz), 10.2 (s, 1H); LD-MS obsd 837.2 [M$^+$], 852.2 [M$^+$+15], 809.2 [M$^+$-CO]795.1 [M$^+$-COCH$_3$]; FAB-MS obsd 836.4503, calcd exact mass 836.4488 ($C_{56}H_{60}N_4OS$); $λ_{abs}$ (toluene) 416, 510, 544, 585, 641 nm.

Zinc(II)-10,20-Bis(3,5-di-tert-butylphenyl)-5-[4-(S-acetylthio)phenyl]porphyrin (Zn-8)

A solution of 6 (56 mg, 172 μmol) in CHCl$_3$ (20 mL) and a solution of Zn(OAc)$_2$·2H$_2$O (734 mg, 3.3 mmol) in methanol (5 mL) were combined and stirred 6.5 h. Purification by column chromatography (silica, CH$_2$Cl$_2$/hexanes 1:1) afforded 54 mg (60.0 μmol, 90%) of a purple solid. IR (neat): ν=3066, 2956, 1703, 1675, 1590, 1469; $^1$H NMR (300.5 MHz, CDCl$_3$): δ=1.55 (s, 36H), 2.59 (s, 3H), 7.79, 8.28 (AA'BB', 2×2H), 7.82 (t, 2H, $^4$J=2.2 Hz), 8.12 (d, 4H, $^4$J=2.2 Hz), 8.99 (d, 2H, $^3$J=4.4 Hz), 9.06 (d, 2H, $^3$J=4.4 Hz), 9.17 (d, 2H, $^3$J=4.4 Hz), 9.43 (d, 2H, $^3$J=4.4 Hz), 10.29 (s, 1H); LD-MS obsd 900.1, 915.2 [M$^+$+15], 872.0 [M$^+$-CO], 857.9 [M$^+$-COCH$_3$]; FAB-MS obsd 898.3617, calcd exact mass 898.3623 ($C_{56}H_{58}N_4OSZn$); $λ_{abs}$ (toluene) 420, 545, 583 nm; $λ_{em}$ (toluene) 591, 640 nm.

Zinc(II)-Disulfide Zn-9

A solution of 9 (14 mg, 8.8 μmol) in CHCl$_3$ (5 mL) and a solution of Zn(OAc)$_2$·2H$_2$O (193 mg, 879 μmol) in methanol (2 mL) were combined and stirred. After 7 h an additional 194 mg (879 μmol) of Zn(OAc)$_2$·H$_2$O was added and stirring was continued for 15.5 h. Purification by column chromatography (silica, CH$_2$Cl$_2$/hexanes 1:2) afforded 9.0 mg (5.2 μmol, 60%) of an orange-purple solid. IR (neat): ν=3067, 2959, 2923, 2862, 1592, 1468; $^1$H NMR (300.5 MHz, CDCl$_3$): δ=1.51 (s, 72H), 7.78 (s, 4H), 8.10, 8.30 (AA'BB', 2×4H), 8.10 (s, 8H), 9.05 (s, 8H), 9.16 (d, 4H, $^3$J=4.4 Hz), 9.42 (d, 4H, $^3$J=4.4 Hz), 10.28 (s, 2H); LD-MS obsd 1716.6, 871.2 [M$^+$/2+15], 856.2 [M$^+$/2], 751.9 [M$^+$-S-$^t$Bu-Me]; FAB-MS obsd 1710.71, calcd exact mass 1710.69 ($C_{108}H_{110}N_8S_2Zn_2$); $λ_{abs}$ (toluene) 421, 545, 585 nm; $λ_{em}$ (toluene) 594, 641 nm.

5,10,15-Tris(3,5-di-tert-butylphenyl)porphyrin (10)

To a solution of 7 (578 mg, 1.0 mmol) in a 1:2 mixture of methanol/THF (30 mL) under argon was added NaBH$_4$ (1.89 g, 50 mmol) in several portions. The mixture was stirred for 2 h, then quenched with water (60 mL) and extracted with CH$_2$Cl$_2$. The organic phase was dried (K$_2$CO$_3$) and the solvents were removed under reduced pressure. The resulting orange oil and crude 5-(3,5-di-tert-butylphenyl)dipyrromethane (Imahori et al. (1999) *Bull. Chem. Soc. Jpn*, 72: 485–502) (334 mg, 1.0 mmol) were dissolved in acetonitrile and stirred at room temperature. Then TFA (930 μL, 12.1 mmol) was added and the solution immediately turned dark blue. After 25 min DDQ (680 mg, 3.0 mmol) was added because the yield did not increase any further (checked by oxidizing an aliquot with DDQ and quantifying with UV/VIS spectroscopy). After 75 min the solution was filtered through a pad of alumina and eluted with $CH_2Cl_2$. The solvents were removed under reduced pressure and the residue was purified by column chromatography (silica, $CH_2Cl_2$/hexanes 1:4–1:2), affording 183 mg (209 μmol, 21% yield) a purple solid. IR (neat): ν=3305, 3064, 2958, 1588, 1468; $^1$H NMR (300.5 MHz, $CDCl_3$): δ=−2.91 (s, 2H), 1.51 (s, 18H), 1.55 (s, 36H), 7.79 (t, 1H, $^4J$=1.5 Hz), 7.81 (t, 2H, $^4J$=2.2 Hz), 8.07 (d, 2H, $^4J$=1.5 Hz), 8.12 (d, 2H, $^4J$=2.2 Hz), 8.92 (d, 2H, $^3J$=5.1 Hz), 8.96 (d, 2H, $^3J$=5.1 Hz), 9.07 (d, 2H, $^3J$=4.4 Hz), 9.34 (d, 2H, $^3J$=5.1 Hz), 10.20 (s, 1H); LD-MS obsd 875.7; FAB-MS obsd 874.5935, calcd exact mass 874.5913 ($C_{62}H_{74}N_4$); $\lambda_{abs}$ (toluene) 416, 510, 544, 585, 641 nm.

Zinc(II)-5,10,15-Tris(3,5-di-tert-butylphenyl) porphyrin (Zn-10)

A solution of 10 (177 mg, 202.2 μmol) in $CHCl_3$ (40 mL) and a solution of $Zn(OAc)_2·2H_2O$ (2.22 g, 10.1 mmol) in methanol (10 mL) were combined and stirred 21 h. Purification by column chromatography (silica, $CH_2Cl_2$/hexanes 1:2) afforded 187 mg (199.2 μmol, 99%) of a red-purple solid. IR (neat): ν=3060, 2960, 2872, 1591, 1470; $^1$H NMR (300.5 MHz, $CDCl_3$): δ=1.52 (s, 18H), 1.54 (s, 36H), 7.78 (t, 1H, $^4J$=1.5 Hz), 7.81 (t, 2H, $^4J$=1.5 Hz), 8.08 (d, 2H, $^4J$=1.5 Hz), 8.12 (d, 2H, $^4J$=1.5 Hz), 9.03 (d, 2H, $^3J$=4.4 Hz), 9.06 (d, 2H, $^3J$=4.4 Hz), 9.15 (d, 2H, $^3J$=4.4 Hz), 9.41 (d, 2H, $^3J$=5.1 Hz), 10.27 (s, 1H); LD-MS obsd 937.6, 951.8 [M$^+$+15], 752.1 [M$^+$-3 $^t$Bu-Me]; FAB-MS obsd 936.5057, calcd exact mass 936.5048 ($C_{62}H_{72}N_4Zn$); $\lambda_{abs}$ (toluene) 419, 545 nm; $\lambda_{em}$ (toluene) 591, 639 nm.

Meso-meso porphyrin dimers Zn-11, Zn-12 and Zn-13

To a solution of Zn-8 (15.9 mg, 17.7 μmol) and Zn-10 (16.6 mg, 17.7 μmol) in $CHCl_3$ (20 mL) was added a solution of $AgPF_6$ (8.9 mg, 35.2 μmol) in acetonitrile (3 mL). The mixture was refluxed for 7 h. Then more $AgPF_6$ (15 mg, 59.3 μmol) was added because the reaction stopped (monitored by analytical SEC). After an additional 22 h an additional 22 mg (87.0 μmol) of $AgPF_6$ was added because the reaction stopped again. Refluxing was continued for 19 h and then the reaction was quenched with water (30 mL). The phases were separated and the organic phase was washed with water and dried ($Na_2SO_4$). The solvents were removed under reduced pressure. The dark purple solid was dissolved in $CHCl_3$ (30 mL). A solution of $Zn(OAc)_2·2H_2O$ (390 mg, 1.8 mmol) in methanol (7 mL) was added and the mixture was stirred for 3 h in the dark. Then the reaction was quenched with water (50 mL) and the phases were separated. The organic phase was washed three times with 5% aq $NaHCO_3$ and dried ($Na_2SO_4$). The solvents were removed under reduced pressure and the residue was dissolved in a minimum amount of toluene. Purification by preparative SEC followed by column chromatography (silica, $CH_2Cl_2$/hexanes 1:2–2:3) afforded 9.9 mg of Zn-11 (5.3 μmol, 30% yield) as an orange solid, 14.3 mg of Zn-12 (7.8 μmol, 44% yield) as a red-purple solid and 7.3 mg of Zn-13 (4.1 μmol, 23% yield) as a brown-purple solid. Zn-11: IR (neat): ν=3060, 2956, 2861, 1592, 1465; $^1$H NMR (300.5 MHz, $CDCl_3$): δ=1.43 (s, 72H), 1.57 (s, 36H), 7.68 (t, 4H, $^4J$=2.2 Hz), 7.83 (t, 2H, $^4J$=1.4 Hz), 8.08 (d, 8H, $^4J$=2.2 Hz), 8.15 (d, 4H, $^3J$=4.4 Hz), 8.30 (d, 4H, $^4J$=1.4 Hz), 8.71 (d, 4H, $^3J$=4.4 Hz), 9.04 (d, 4H, $^3J$=4.4 Hz), 9.08 (d, 4H, $^3J$=5.1 Hz); LD-MS obsd 1877.1; FAB-MS obsd 1870.87, calcd exact mass 1870.99 ($C_{124}H_{142}N_8Zn_2$); $\lambda_{abs}$ (toluene) 421, 460, 561 nm; $\lambda_{em}$ (toluene) 625, 660 nm. Zn-12: IR (neat): ν=3069, 2955, 1700, 1588, 1465; $^1$H NMR (300.5 MHz, $CDCl_3$): δ=1.43 (s, 36H), 1.44 (s, 36H), 1.57 (s, 18H), 7.66–7.72 (m, 4H), 7.82 (t, 1H, $^4J$=2.2Hz), 7.85, 8.37 (AA'BB', 2×2H), 8.09 (d, 8H, $^4J$=1.5 Hz), 8.12 (d, 2H, $^3J$=5.1 Hz), 8.17 (d, 2H, $^4J$=2.2 Hz), 8.17 (d, 2H, $^3J$=4.4 Hz), 8.71 (d, 2H, $^3J$=5.1 Hz), 8.72 (d, 2H, $^3J$=5.1 Hz), 9.02–9.07 (m, 6H), 9.08 (d, 2H, $^3J$=4.4 Hz); LD-MS obsd 1423.7; FAB-MS bsd 1832.85, calcd exact mass 1832.85 ($C_{118}H_{128}N_{16}OSZn_2$); $\lambda_{abs}$ (toluene) 420, 460, 561 nm; $\lambda_{em}$ (toluene) 626, 660 nm. Zn-13: IR (neat): ν=2919, 1702, 1561, 1461; $^1$H NMR (300.5 MHz, $CDCl_3$): δ=1.44 (s, 72H), 7.70 (t, 4H, $^4J$=1.5 Hz), 7.85, 8.37 (AA'BB', 2×4H), 8.09 (d, 8H, $^4J$=1.5 Hz), 8.14 (d, 4H, $^3J$=4.4 Hz), 8.72 (d, 4H, $^3J$=5.1 Hz), 9.03 (d, 4H, $^3J$=5.1 Hz), 9.05 (d, 4H, $^3J$=5.1 Hz); LD-MS obsd 1801.1, 1816.3 [M$^+$+15], 1772.9 [M$^+$-CO], 1758.9 [M$^+$-COCH$_3$], 1715.8 [M$^+$-2 COCH$_3$]; FAB-MS obsd 1794.62, calcd exact mass 1794.71 ($C_{112}H_{114}N_8O_2S_2Zn_2$); $\lambda_{abs}$ (toluene) 421, 461, 561 nm; $\lambda_{em}$ (toluene) 626, 659 nm.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An apparatus for storing data, said apparatus comprising:

a fixed electrode electrically coupled to a storage medium comprising a storage molecule comprising a first subunit and a second subunit wherein the first and second subunits are tightly coupled such that oxidation of the first subunit alters the oxidation potential of the second subunit.

2. The apparatus of claim 1, wherein the subunits are selected from the group consisting of a porphyrinic macrocycle, a metallocene, a linear polyene, a cyclic polyene, a heteroatom-substituted linear polyene, a heteroatom-substituted cyclic polyene, a tetrathiafulvalene, a tetraselenafulvalene, a metal coordination complex, a buckyball, a triarylamine, a 1,4-phenylenediamine, a xanthene, a flavin, a phenazine, a phenothiazine, an acridine, a quinoline, a 2,2'-bipyridyl, a 4,4'-bipyridyl, a tetrathiotetracene, and a peri-bridged naphthalene dichalcogenide.

3. The apparatus of claim 2, wherein the subunits are both porphyrinic macrocycles or metallocenes.

4. The apparatus of claim 2, wherein the subunits are both ferrocenes.

5. The apparatus of claim 2, wherein the subunits are both porphyrinic macrocycles.

6. The apparatus of claim 2, wherein a pair of the tightly coupled subunits has the following structure:

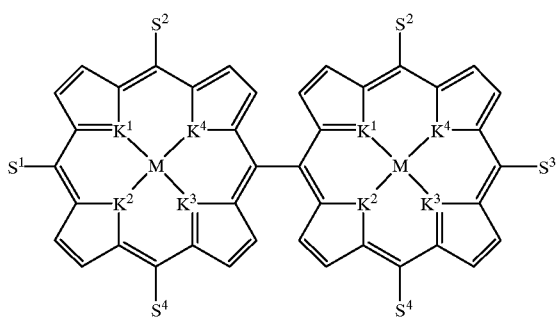

wherein $S^1$, $S^2$, $S^3$, and $S^4$ are substituents independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts, or one or more of $S^1$, $S^2$, $S^3$, and $S^4$ are -L-X where -L-X, when present is optionally present on one or both subunits and L, when present, is a linker;

X is selected from the group consisting of a substrate, a reactive site that can covalently couple to a substrate, and a reactive site that can ionically couple to a substrate;

M is a metal; and $K^1$, $K^2$, $K^3$, and $K^4$ are independently selected from the group consisting of N, O, S, Se, Te, and CH.

7. The apparatus of claim 6, wherein M is selected from the group consisting of Zn, Mg, Cd, Hg, Cu, Ag, Au, Ni, Pd, Pt, Co, Rh, Ir, Mn, B, Al, Pb, Ga, Fe, and Sn.

8. The apparatus of claim 6, wherein M is selected from the group consisting of Zn, Mg, and (H,H).

9. The apparatus of claim 6, wherein $S^1$, $S^2$, and $S^3$ are independently selected from the group consisting of mesityl, $C_6F_5$, 2,4,6-trimethoxyphenyl, phenyl, p-tolyl, p-(tert-butyl) phenyl, 3,5-dimethylphenyl, 3,5-di(tert-butyl)phenyl, 3,5-dimethoxyphenyl, 3,5-dialkoxyphenyl, and n-pentyl.

10. The apparatus of claim 6, wherein X is selected from the group consisting of $SCOR^1$, and $SCON(R^2)(R^3)$, wherein $R^1$, $R^2$, and $R^3$ are independently selected groups.

11. The apparatus of claim 6, wherein X is selected from the group consisting of SCN, SCONH(Et), $SCOCH_3$, and SH.

12. The apparatus of claim 6, wherein L-X is selected from the group consisting 4-(2-(4-mercaptophenyl)ethynyl) phenyl, 4-mercaptomethylphenyl, 4-hydroselcnophenyl, 4-(2-(4-hydroselenophenyl)ethynyl)phenyl, 4-hydrotellurophenyl, 2-(4-mercaptophenyl)ethynyl, 2-(4-hydroselenophenyl)ethynyl, 2-(4-hydrotellurophenyl) ethynyl, and 4-(2-(4-hydrotellurophenyl)ethynyl)phenyl.

13. The apparatus of claim 6, wherein $S^1$ and $S^3$ are both the same; and $K^1$, $K^2$, $H^3$, and $K^4$ are all the same.

14. The apparatus of claim 13, wherein

M is Zn; and $K^1$, $K^2$, $K^3$, and $K^4$ are all N.

15. The apparatus of claim 13, wherein a pair of the tightly coupled subunits has the following structure:

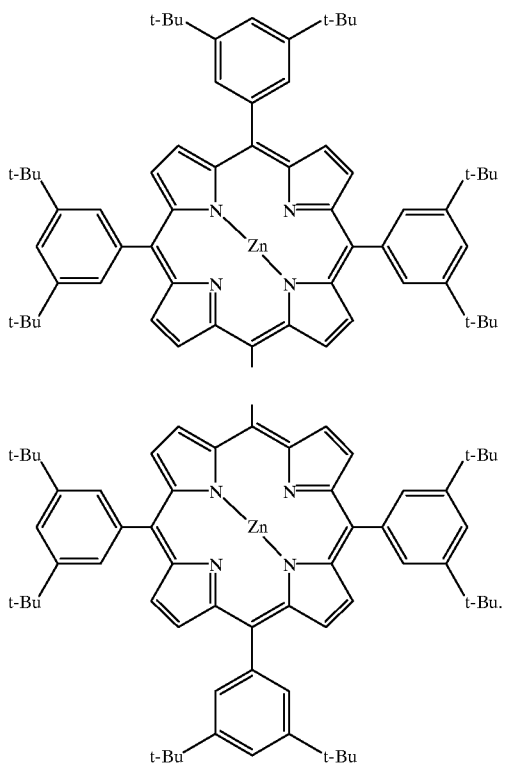

16. The apparatus of claim 13, wherein a pair of the tightly coupled subunits has the following structure:

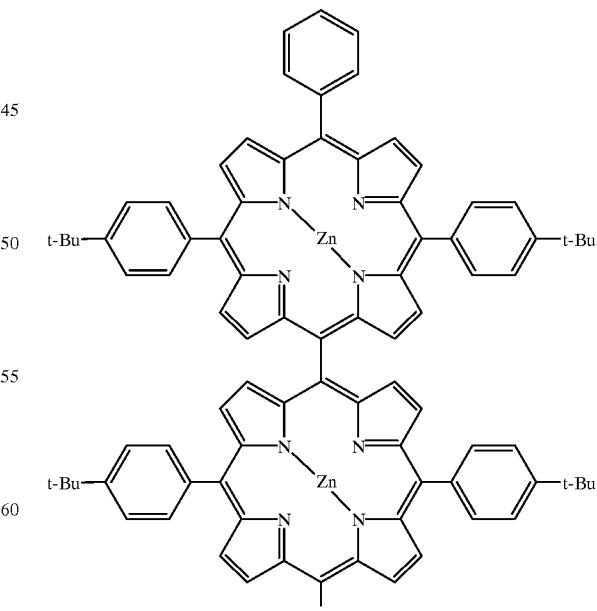

-continued

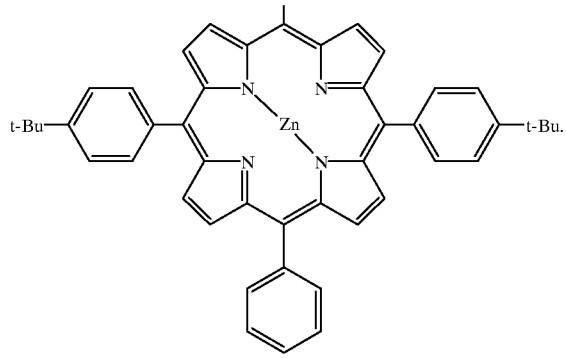

17. The apparatus of claim 13, wherein a pair of the tightly coupled subunits has the following structure:

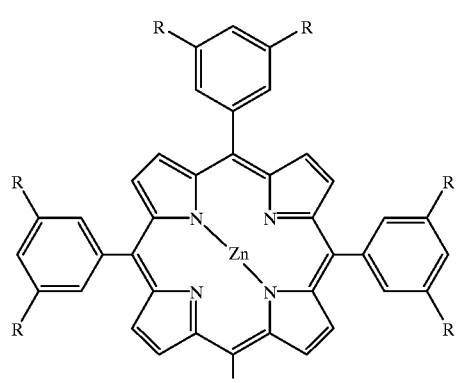

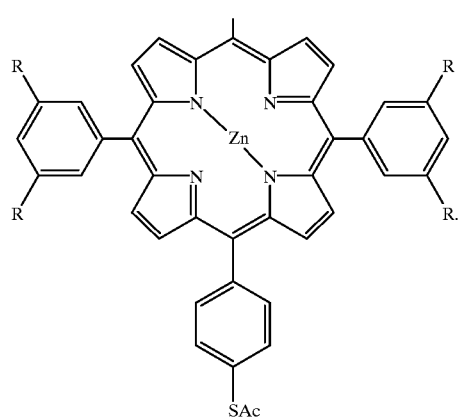

18. The apparatus of claim 13, wherein a pair of the tightly coupled units has the following structure:

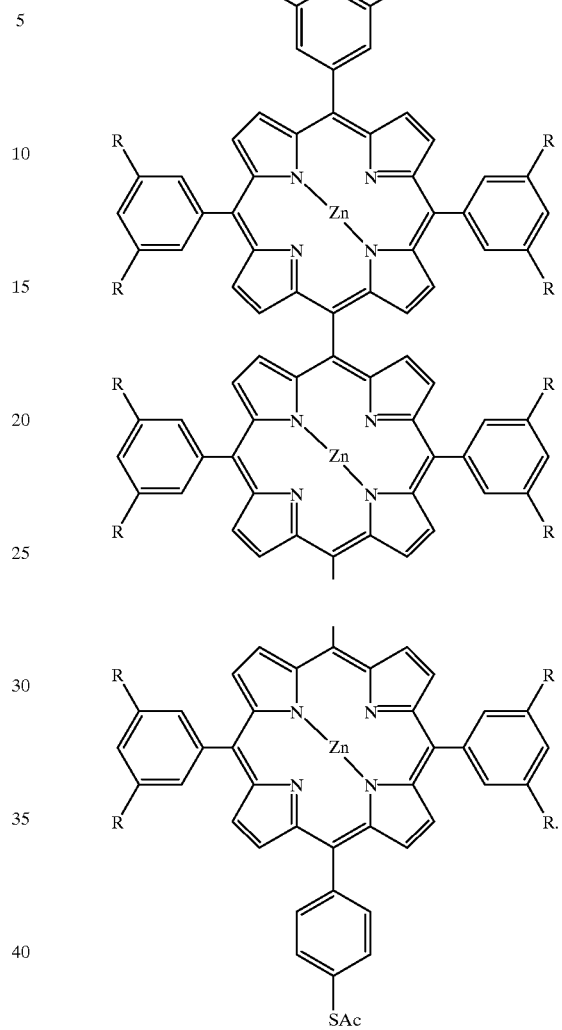

19. The apparatus of claim 1, wherein said storage medium has at least three different and distinguishable non-neutral oxidation states.

20. The apparatus of claim 1, wherein said storage medium has at least eight different and distinguishable oxidation states.

21. The apparatus of claim 1, wherein said storage molecule is covalently linked to said electrode.

22. The apparatus of claim 1, wherein said storage molecule is electrically coupled to said electrode through a linker.

23. The apparatus of claim 1, wherein said storage molecule is covalently linked to said electrode through a linker.

24. The apparatus of claim 23, wherein said linker is a thiol linker.

25. The apparatus of claim 1, wherein said storage medium is juxtaposed in the proximity of said electrode such that electrons can pass from said storage medium to said electrode.

26. The apparatus of claim 1, wherein said storage medium is juxtaposed to a dielectric material imbedded with counterions.

27. The apparatus of claim 1, wherein said storage medium and said electrode are fully encapsulated in an integrated circuit.

28. The apparatus of claim 1, wherein said storage medium is electronically coupled to a second fixed electrode that is a reference electrode.

29. The apparatus of claim 1, wherein said storage medium is present on a single plane in said device.

30. The apparatus of claim 1, wherein said storage medium is present at a multiplicity of storage locations.

31. The apparatus of claim 30, wherein said storage locations are present on a single plane in said device.

32. The apparatus of claim 30, wherein said apparatus comprises multiple planes and said storage locations are present on multiple planes of said device.

33. The apparatus of claim 30, wherein said storage locations range from about 1024 to about 4096 different locations.

34. The apparatus of claim 33, wherein each location is addressed by a single electrode.

35. The apparatus of claim 33, wherein each location is addressed by two electrodes.

36. The apparatus of claim 1, wherein said electrode is connected to a voltage source.

37. The apparatus of claim 36, wherein said voltage source is the output of integrated circuit.

38. The apparatus of claim 1, wherein said electrode is connected to a device to read the oxidation state of said storage medium.

39. The apparatus of claim 38, wherein said device is selected from the group consisting of a voltammetric device, an amperometric device, and a potentiometric device.

40. The apparatus of claim 39, wherein said device is an impedance spectrometer or a sinusoidal voltammeter.

41. The apparatus of claim 38, wherein said device provides a Fourier transform of the output signal from said electrode.

42. The apparatus of claim 38, wherein said device refreshes the oxidation state of said storage medium after reading said oxidation state.

43. The apparatus of claim 1, wherein the second subunit can be oxidized by a voltage difference no greater than about 2 volts.

44. An information storage medium, said storage medium comprising one or more storage molecules such that said storage medium has at least two different and distinguishable non-neutral oxidation states, wherein the storage molecules comprise a first subunit and a second subunit wherein the first and second subunits are tightly coupled such that oxidation of the first subunit alters the oxidation potential of the second subunit, wherein said subunits are selected from the group consisting of a porphyrinic macrocycle and a metallocene and said molecule has at least two different non-zero oxidation states and said oxidation states are within a redox potential range of less than about 2 volts.

45. The molecule of claim 44, wherein the subunits are both ferrocenes.

46. The molecule of claim 44, wherein the subunits are both porphyrinic macrocycles.

47. The molecule of claim 44, wherein said storage molecule comprises a pair of the tightly coupled subunits has the following subunits has the following structure:

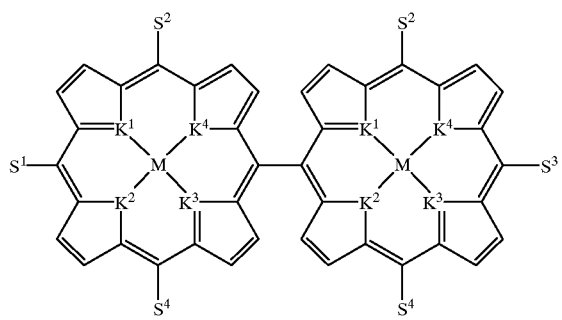

wherein $S^1$, $S^2$, $S^3$, and $S^4$ are substituents independently selected from the group consisting of aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl wherein said substituents provide a redox potential range of less than about 2 volts, or one or more of $S^1$, $S^2$, $S^3$, and $S^4$ are -L-X where -L-X, when present is optionally present on one or both subunits and L, when present, is a linker;

X is selected from the group consisting of a substrate, a reactive site that can covalently couple to a substrate, and a reactive site that can ionically couple to a substrate;

M is a metal; and $K^1$, $K^2$, $K^3$, and $K^4$ are independently selected from the group consisting of N, O, S, Se, Te, and CH.

48. The molecule of claim 47, wherein M is selected from the group consisting of Zn, Mg, Cd, Hg, Cu, Ag, Au, Ni, Pd, Pt, Co, Rh, Ir, Mn, B, Al, Pb, Ga, Fe, and Sn.

49. The molecule of claim 47, wherein M is selected from the group consisting of Zn, Mg, and (H,H).

50. The molecule of claim 47, wherein $S^1$, $S^2$, and $S^3$ are independently selected from the group consisting of mesityl, $C_6F_5$, 2,4,6-trimethoxyphenyl, phenyl, p-tolyl, p-(tert-butyl) phenyl, 3,5-dimethylphenyl, 3,5-di(tert-butyl)phenyl, 3,5-dimethoxyphenyl, 3,5-dialkoxyphenyl, and n-penty.

51. The molecule of claim 47, wherein X is selected from the group consisting of SCN, SCONH(Et), SCOCH$_3$, and SH.

52. The molecule of claim 47, wherein L-X is selected from the group consisting of 4-(2-(4-mercaptophenyl) ethynyl)phenyl, 4-mercaptomethylphenyl, 4-hydroselenophenyl, 4-(2-(4-hydroselenophenyl)ethynyl) phenyl, 4-hydrotellurophenyl, 2-(4-mercaptophenyl) ethynyl, 2-(4-hydroselenophenyl)ethynyl, 2-(4-hydrotellurophenyl)ethynyl, and 4-(2-(4-hydrotellurophenyl)ethynyl)phenyl.

53. The molecule of claim 47, wherein $S^1$ and $S^3$ are both the same; and $K^1$, $K^1$, $K^3$, and $K^4$ are all the same.

54. The molecule of claim 53, wherein

M is Zn; and $K^1$, $H^2$, $K^3$, and $K^4$ are all N.

55. The molecule of claim 53, wherein a pair of the tightly coupled subunits has the following structure:

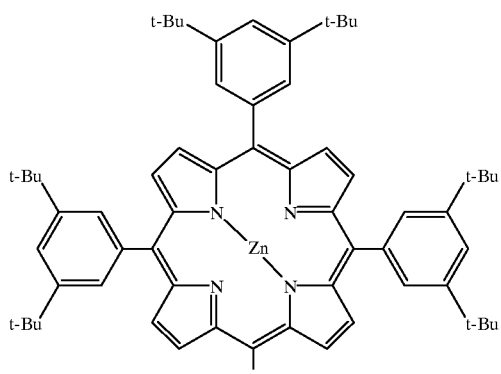
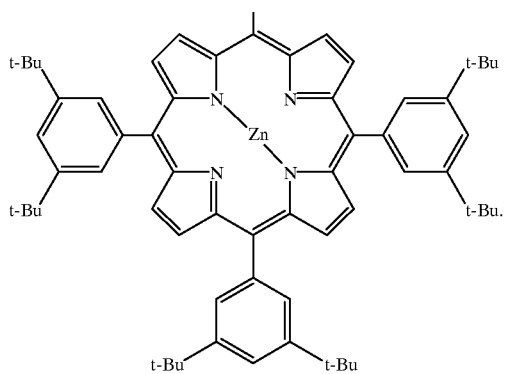
56. The molecule of claim 53, wherein a pair of the tightly coupled subunits has the following structure:
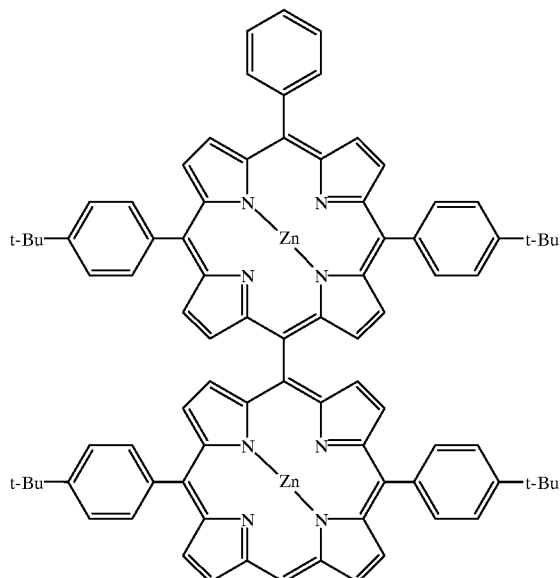
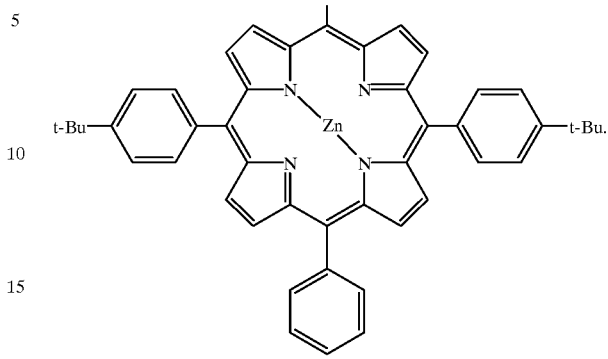
57. The molecule of claim 53, wherein a pair of the tightly coupled subunits has the following structure:
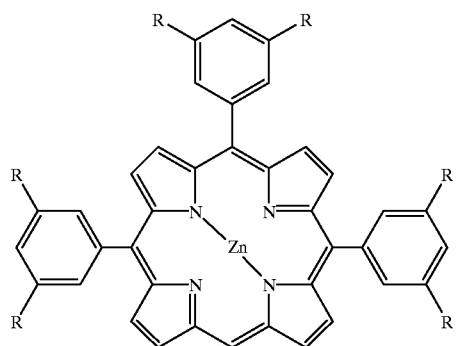
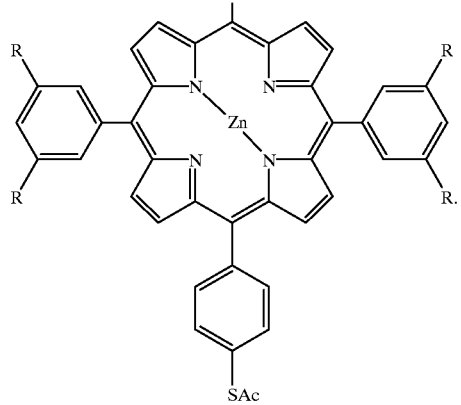
58. The molecule of claim 53, wherein a pair of the tightly coupled subunits has the following structure:

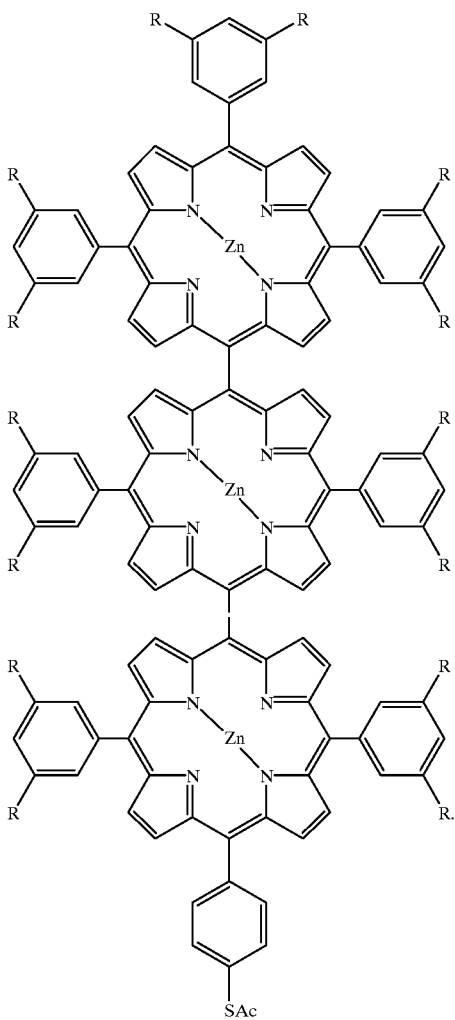

59. The molecule of claim 47, wherein said storage medium has at least three different and distinguishable non-neutral oxidation states.

60. The molecule of claim 47, wherein said storage medium has at least eight different and distinguishable oxidation states.

61. A method of storing data, said method comprising:
   i) providing an apparatus according to claim 1; and
   ii) applying a voltage to said electrode at sufficient current to set an oxidation state of said storage medium.

62. The method of claim 61, wherein said voltage ranges up to about 2 volts.

63. The method of claim 61, wherein said voltage is the output of an integrated circuit.

64. The method of claim 61, wherein said voltage is the output of a logic gate.

65. The method of claim 61, further comprising detecting the oxidation sate of said storage medium and thereby reading out the data stored therein.

66. The method of claim 65, wherein said detecting the oxidation state of the storage medium further comprises refreshing the oxidation state of the storage medium.

67. The method of claim 65, wherein said detecting comprises analyzing a readout signal in the time domain.

68. The method of claim 65, wherein said detecting comprises analyzing a readout signal in the frequency domain.

69. The method of claim 68, wherein said detecting comprises performing a Fourier transform on said readout signal.

70. The method of claim 65, wherein said detecting utilizes a voltammetric method.

71. In a computer system, a memory device, said memory device comprising the apparatus of claim 1.

72. A computer system comprising a central processing unit, a display, a selector device, and a memory device, said memory device comprising the apparatus of claim 1.

* * * * *